United States Patent
Wraith

(10) Patent No.: US 10,730,919 B2
(45) Date of Patent: *Aug. 4, 2020

(54) PEPTIDES

(71) Applicant: APITOPE INTERNATIONAL NV, Diepenbeek (BE)

(72) Inventor: David Wraith, Bristol (GB)

(73) Assignee: APITOPE INTERNATIONAL NV, Diepenbeek (BE)

(*) Notice: Subject to any disclaimer, the term of this patent is extended or adjusted under 35 U.S.C. 154(b) by 0 days.

This patent is subject to a terminal disclaimer.

(21) Appl. No.: 15/903,379

(22) Filed: Feb. 23, 2018

(65) Prior Publication Data

US 2018/0327463 A1 Nov. 15, 2018

Related U.S. Application Data

(63) Continuation of application No. 14/910,372, filed as application No. PCT/IB2014/063739 on Aug. 6, 2014, now Pat. No. 9,938,329.

(30) Foreign Application Priority Data

Aug. 6, 2013 (GB) .................... 1314052.0

(51) Int. Cl.
| | |
|---|---|
| C07K 14/47 | (2006.01) |
| A61K 39/00 | (2006.01) |
| C07K 14/72 | (2006.01) |
| C07K 7/08 | (2006.01) |
| A61K 38/00 | (2006.01) |

(52) U.S. Cl.
CPC .......... C07K 14/47 (2013.01); A61K 39/0005 (2013.01); C07K 7/08 (2013.01); C07K 14/723 (2013.01); A61K 38/00 (2013.01)

(58) Field of Classification Search
CPC .... A61K 38/00; A61K 39/0005; C07K 14/47; C07K 14/723; C07K 7/08
See application file for complete search history.

(56) References Cited

U.S. PATENT DOCUMENTS

| 9,938,329 B2 * | 4/2018 | Wraith .............. A61K 39/0005 |
| 2008/0305098 A1 | 12/2008 | Fenning et al. |

FOREIGN PATENT DOCUMENTS

| EA | 201070681 A1 | 10/2010 |
| EP | 0433509 B1 | 11/1996 |
| FR | 2842812 A1 | 1/2004 |
| JP | 2006188507 | 7/2006 |
| RU | 2486201 C2 | 6/2013 |
| WO | WO-02/16410 A2 | 2/2002 |
| WO | WO-03/64464 A1 | 8/2003 |
| WO | WO-2007/057778 A2 | 5/2007 |
| WO | WO-2008/063776 A2 | 5/2008 |
| WO | WO-2009/071886 A1 | 6/2009 |
| WO | WO-2010/133834 A2 | 11/2010 |

OTHER PUBLICATIONS

Flynn et al. Graves' hyperthyroidism and thyroiditis in HLA-DRB1*0301 (DR3) transgenic mice after immunization with thyrotropin receptor DNA. Clinical and Experimental Immunology, 2004. vol. 135, pp. 35-40. (Year: 2004).*
Inaba et al., The Role of Glutamic or Aspartic Acid in Position Four of the Epitope Binding Motif and Thyrotropin Receptor-Extracellular Domain Epitope Selection in Graves' Disease, J. Clin. Endocrinol. Metab. 95:2909-2916 (2010).
Kellermann et al., TSH Receptor Sequences Recognized by CD4+T Cells in Graves' Disease Patients and Healthy Controls, Journal of Autoimmunity. 8:685-698 (1995).
Martin et al., Detection of Major T Cell Epitopes on Human Thyroid Stimulating Hormone Receptor by Overriding Immune Heterogeneity in Patients with Graves' Disease, J. Clin. Endocrinol. Metab. 82:2361-3366 (1997).
Akdis et al J., Role of interleukin 10 in specific immunotherapy, Clin. Invest., 102:98-106 (1998).
Anderton et al., Hierarchy in the ability of T cell epitopes to induce peripheral tolerance to antigens from myelin, Eur. J. Immunol., 28:1251-61 (1998).
Anderton et al., Mechanisms of central and peripheral T-cell tolerance: lessons from experimental models of multiple sclerosis, Immunological Reviews, 169:123-37(1999).
Australian Patent Application No. 2014304108, Examination Report No. 1, dated Dec. 11, 2017.
Burkhart et al., Peptide-induced T cell regulation of experimental autoimmune encephalomyelitis: a role for IL-10, Int. Immunol., 11:1625-1634(1999).
Creighton Proteins Structures and Molecular Principles, WET Freeman and Co, New York NY (1983)).
De Groot et al., "Evalution of T cell stimulation by thyrotropin-receptor epitopes in Graves' disease", J. Endocrinol. Invest., 32(1):52-6 (2009).
Endo et al., Rabbit antibodies against two different extracellular domains of human thyrotropin receptor possess thyroid stimulating activities, Biochem. Biophys. Res. Commun., 179(3):1548-53 (1991).
Fugger et al., Expression of HLA-DR4 and human CD4 transgenes in mice determines the variable region beta-chain T-cell repertoire and mediates an HLA-DR-restricted immune response, PNAS, 91:6151-5(1994).

(Continued)

Primary Examiner — Marcela M Cordero Garcia
(74) Attorney, Agent, or Firm — Marshall, Gerstein & Borun LLP

(57) ABSTRACT

The present invention provides a peptide at least partially derivable from human Thyroid Stimulating Hormone Receptor (TSHR) which peptide is capable of binding to an MHC molecule in vitro and being presented to a T cell without further antigen processing. The present invention also relates to the use of such peptides for the prevention or suppression of activating autoantibody formation in Graves' Disease.

21 Claims, 19 Drawing Sheets

Specification includes a Sequence Listing.

(56) References Cited

OTHER PUBLICATIONS

Inaba et al., Immune Response of Mice Transgenic of rHuman Histocompatibility Leukocyte Antigen-DR to HumanThyrotropin Receptor-Extracellular Domain, Thyroid, 19(11):1271-80 (2009).
Inaba et al., Thyrotropin receptor epitopes and their relation to histocompatibility leukocyte antigen-DR molecules in Graves' disease, J. Clin. Endocrinol. Metab., 91(6):2286-94 (2006).
International Search Report and Written Opinion of the International Search Authority, European Patent Office, dated Jul. 9, 2015.
Jacobson et al., The HLA gene complex in thyroid autoimmunity: From epidemiology to etiology, J. Autoimmun. 30(1-2):58-62 (2008).
Liu et al., Int. Immunol., 7:1255-63 (1995).
Metzler et al., Inhibition of experimental autoimmune encephalomyelitis by inhalation but not oral administration of the encephalitogenic peptide: influence of MHC binding affinity, Int. Immunol., 5:1159-65 (1993).
Muller et al., Successful immunotherapy with T-cell epitope peptides of bee venom phospholipase A2 induces specific T-cell anergy in patients allergic to bee venom, J. Allergy Clin. Immunol., 101:747-54 (1998).
Roberge et al., A strategy for a convergent synthesis of N-linked glycopeptides on a solid support. Science, 269:202-4 (1995).
Russian Patent Application No. 2016107873, Official Action and Search Report, dated Jan. 16, 2018.
Summers et al., Phenotypic characterization of five dendritic cell subsets in human tonsils, Am. J. Pathol., 159:285-95 (2001).
Tandon et al., T Cell responses to synthetic TSH receptor pepties in Graves' disease, Clin. Exp. Immunol., 89(3):468-73 (1992).

\* cited by examiner

Fig. 11
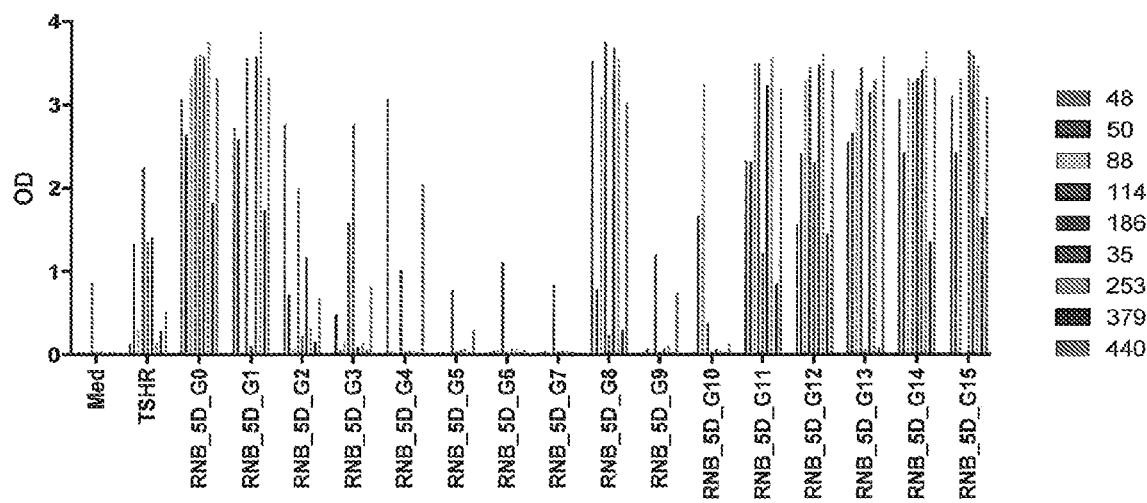
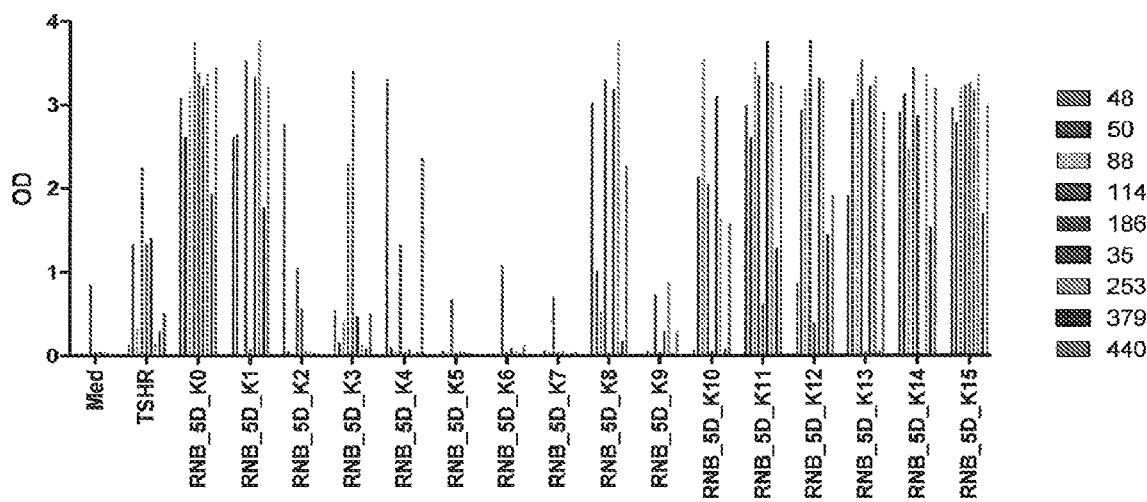

Fig. 14
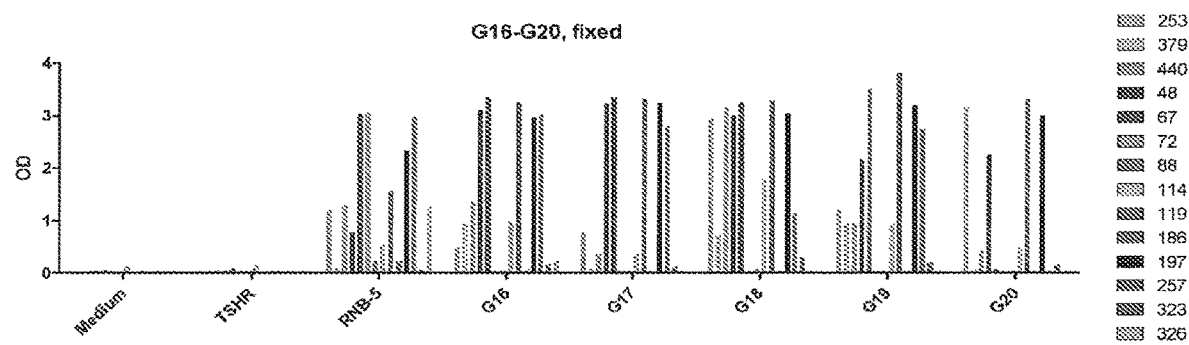
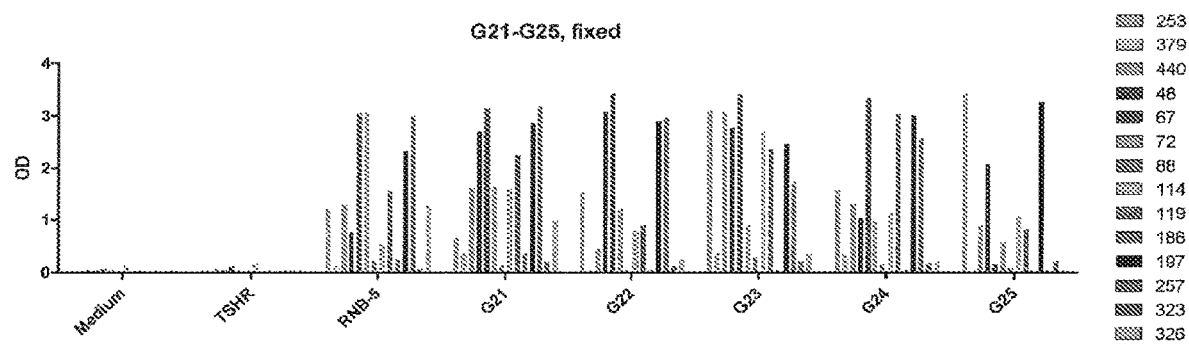
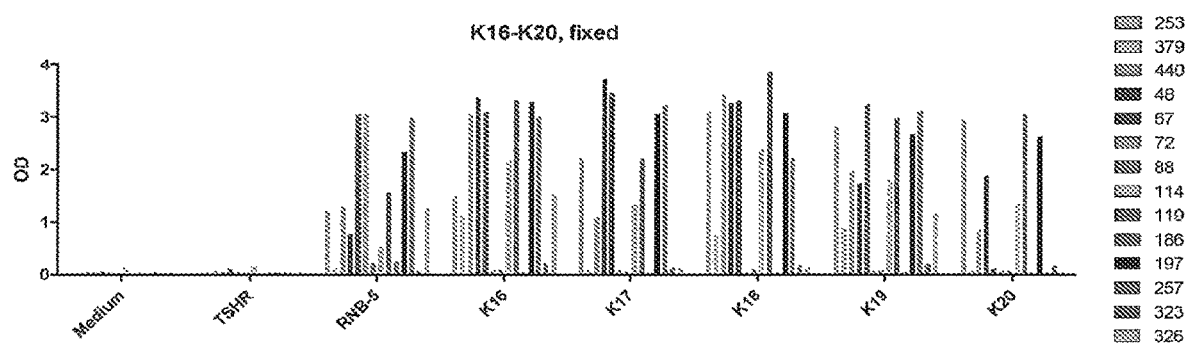

Fig. 15
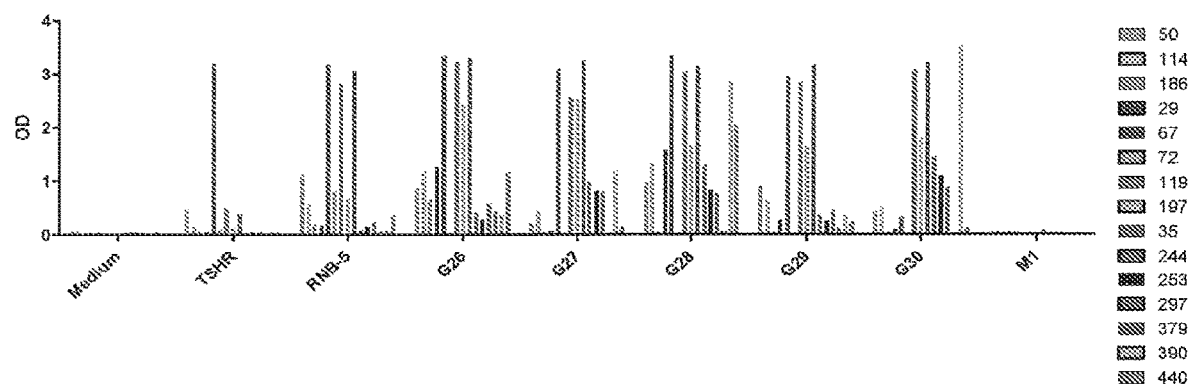
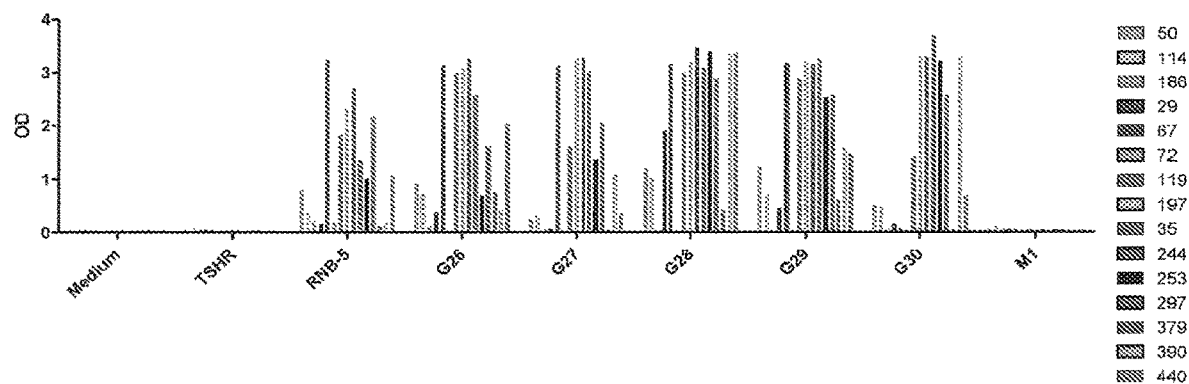

PEPTIDES

FIELD OF THE INVENTION

The present invention relates to peptides, at least part of which is derived from Thyroid Stimulating Hormone Receptor (TSHR). These peptides may be useful in the prevention and/or treatment of Graves Disease (GD).

BACKGROUND TO THE INVENTION

Graves' Disease is characterised by an overactive thyroid gland, which results in the production of an excessive amount of thyroid hormone and enlargement of the thyroid gland (goitre). The resulting state of hyperthyroidism may cause a wide range of neuropsychological and physical symptoms. GD is the most common cause of hyperthyroidism (60-90% of all cases) and usually presents itself during midlife, but also appears in children, adolescents, and the elderly. It affects up to 2% of the female population, and is between five and ten times as common in females as in males. Pediatric GD affects about 6,000 children in the US and 6,000 in the EU. GD is also the most common cause of severe hyperthyroidism, which is accompanied by more clinical signs and symptoms and laboratory abnormalities as compared with milder forms of hyperthyroidism.

There is a strong hereditary component linked to GD. There are no recent population studies on GD, however, a few quasi population studies on hyperthyroidism do exist and all estimates for incidence and prevalence of GD are thus approximate. The incidence of hyperthyroidism varies from 26:100,000 to 93:100,000 and the overall prevalence is estimated to be at 1.3%, with 42% of cases being overt and 62% subclinical.

About 30-50% of people with GD will also suffer from Graves' opthalmopathy (GO), a protrusion of one or both of the eyes. Many cases of GO are mild and self-limiting, however 20% of cases have significant/moderate to severe disease, with at least half of these require steroids and 3-5% of GO patients have painful, sight-threatening disease with dysthyroid optic neuropathy (DON). The budging of the eyes may cause severe dryness of the cornea as the eye lids are unable to close at night. Increased pressure in the optic nerve can lead to visual field defects and vision loss. GO may also be associated with pretibial myxedemia.

The symptoms and signs of GD virtually all result from the direct and indirect effects of hyperthyroidism, with main exceptions being GO, goitre, and pretibial myxedema. Symptoms of hyperthyroidism may include insomnia, hand tremor, hyperactivity, hair loss, excessive sweating, heat intolerance and weight loss despite increased appetite. Further signs are most commonly a diffusely enlarged (usually symmetric) non-tender thyroid, lid lag, excessive lacrimation due to Graves' opthalmopathy, arrhythmias of the heart and hypertension. Thyrotoxic patients may experience behavioural and personality changes, such as psychosis, agitation, and depression. In milder hyperthyroidism, patients may experience less overt manifestations, for example anxiety, restlessness, irritability and emotional lability.

There is currently no cure available for GD and present treatments are therefore directed towards targeting the presenting symptoms. There are three treatment modalities for GD, oral antithyroid drugs (ATDs), radioactive iodine (RAI) and thyroidectomy. The latter two approaches result in lifetime supplementation of thyroid hormones. Therapy with radioiodine is the most common treatment in the United States, whilst ATDs are the first line treatment in Europe, Japan and most of the rest of the world.

ATD therapy is associated with some rare side-effects and has a remission rate of 50-60%. There is growing recognition the RAI can precipitate or worsen active GO and the number of patients treated with ATDs is the United States is increasing.

Due to the varying success of each treatment option, patients are often subjected to more than one approach if the first attempted treatment does not prove entirely successful. The risk of relapse or subsequent hypothyroidism is substantial and the general efficacy of available treatments for GD is less than desired. There is thus a need for alternative therapies for GD that are effective at treating GD and at alleviating or reducing the symptoms of the disease.

DESCRIPTION OF THE FIGURES

FIG. 5A, Mice are injected subcutaneously at the back of the neck with 100 μg of peptide on days −8, −6 and −4 (high dose schedule). On day 0, mice are injected subcutaneously at the base of the tail with RNB-5/CFA. FIG. 5B, Mice are injected subcutaneously at the back of the neck with 0.1 µg, 1 µg and 10 µg peptide on days −15, −13 and −11, followed by 3 injections of 100 µg peptide on days −8, −6 and −4 (dose escalation schedule). On day 0, mice are injected subcutaneously at the base of the tail with TSHR/CFA or peptide/CFA. For both schedules, mice are sacrificed 10 days after immunization to measure the proliferation of LN cells and splenocytes upon TSHR restimulation.

FIG. 6A-6E: Ex vivo tolerance induction by RNB-5 apitopes. Mice are pretreated with RNB-5 apitopes according to the high dose schedule (FIGS. 6A-6B) or the dose escalation schedule (FIGS. 6C-6F). Data represent mean±SEM of SI values for the PBS-treated mice (black lines) and peptide-treated mice (red lines). FIGS. 6A, 6 B, 6C, 6E and 6F represent experiments performed in DR3 mice, FIG. 6D represents an experiment performed in DR4 mice. 2-way ANOVA was used to measure overall treatment effects on T cell proliferation and p-values are written in the graphs. Bonferroni post-hoc testing was used and significant differences are indicated in the graphs (* p<0.05;  p<0.01; * p<0.001). SI, stimulation index; LN, lymph nodes.

FIG. 11: Response of TSHR- and RNB-5-specific hybridoma clones, isolated from HLA-DR3 or HLA-DR4 mice immunized with TSHR/CFA, to RNB-5D modified peptides. Hybridoma clones (represented in different colours) were cultured with fresh APCs and 25 µg/mL antigen for 48 hours prior to determination of IL-2 production. Replacement of amino acids in the central region of the RNB-5D-GKK or RNB-5D-KKK hampers recognition by hybridoma clones, indicating that those amino acids are important in the epitope region.

FIG. 14: Response of TSHR- and RNB-5-specific hybridoma clones, isolated from HLA-DR3 or HLA-DR4 mice immunized with TSHR/CFA, to RNB-5D modified peptides. Hybridoma clones (represented in different colours) were cultured with fixed APCs and 25 µg/mL antigen for 48 hours prior to determination of IL-2 production.

FIG. 15: Response of TSHR- and RNB-5-specific hybridoma clones, isolated from HLA-DR3 or HLA-DR4 mice immunized with TSHR/CFA, to RNB-5D modified peptides. Hybridoma clones (represented in different colours) were cultured with fresh and fixed APCs and 25 µg/mL antigen for 48 hours prior to determination of IL-2 production.

SUMMARY OF ASPECTS OF THE INVENTION

Figure 1:
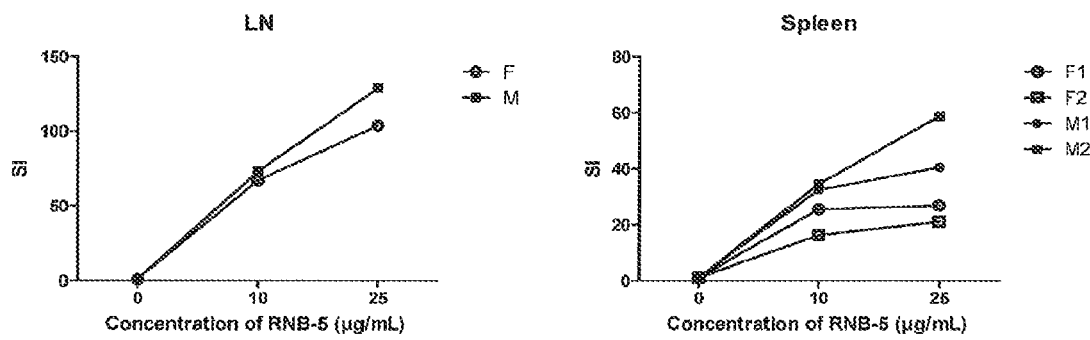
FIG. 1: Immunogenicity of RNB-5 in DR3 mice. Mice (N=2 male; N=2 female) were primed with RNB-5 and after 10 days, LN cells (pooled per gender) and splenocytes were cultured with different concentrations of peptide and cell proliferation was measured. Stimulation indexes (SI) represent the ratio of thymidine incorporation of peptide-stimulated culture to that of non-stimulated culture. F, female; M, male; LN, lymph nodes.

The present inventors have identified a number of peptides derived from TSHR which are useful in the prevention and/or treatment of GD.

In a first aspect, the present invention provides a peptide which is capable of binding to an MHC molecule in vitro and being presented to a T cell without antigen processing, and which comprises all or a portion of the following Thyroid Stimulating Hormone Receptor (TSHR) peptides:

```
RINT35:
                                        (SEQ ID No 1)
ISRIYVS1DVTLQQLESHSFYNLSKVTHI

RNB4:
                                        (SEQ ID No 2)
LRTIPSHAFSNLPNISRIYVSIDVTLQQL

RNB9:
                                        (SEQ ID No 3)
TGLKMFPDLTKVYSTDIFFILEITDNPYM

RNB_12:
                                       (SEQ ID No 64)
LTLKLYNNGFTSVQGYAFNGTKLDAVYL
```

The peptide may be selected from the following TSHR peptides and derivatives thereof:

```
RNB_5D-GKK:
                                       (SEQ ID No 12)
KKGIYVSIDVTLQQLESHGKK

RNB_5D-KKK:
                                      (SEQ ID No. 21)
KKKIYVSIDVTLQQLESHKKK

RNB_5E-GKK:
                                       (SEQ ID No 13)
KKGYVSIDVTLQQLESHSGKK

RNB_5A:
                                        (SEQ ID No 6)
ISRIYVSIDVTLQQL

RNB_5B:
                                        (SEQ ID No 7)
SRIYVSIDVTLQQLE

RNB_5C:
                                        (SEQ ID No 8)
RIYVSIDVTLQQLES

RNB_5D:
                                        (SEQ ID No 9)
IYVSIDVTLQQLESH

RNB_5E:
                                       (SEQ ID No 10)
YVSIDVTLQQLESHS

RNB_5F:
                                       (SEQ ID No 11)
VSIDVTLQQLESHSF

RNB_5F-GKK:
                                       (SEQ ID No 14)
KKGVSIDVTLQQLESHSFGKK

RNB_4J-GKK:
                                       (SEQ ID No 16)
KKGSNLPNISRIYVSIDVGKK

RNB_4J:
                                       (SEQ ID No 15)
SNLPNISRIYVSIDV

RNB_4K:
                                      (SEQ ID No. 62)
NLPNISRIYVSIDVT

RNB_4K-GKK:
                                      (SEQ ID No. 63)
KKGNLPNISRIYVSIDVTGKK

RNB_9A:
                                       (SEQ ID No 17)
TGLKMFPDLTKVYST

RNB_9B:
                                       (SEQ ID No 18)
GLKMFPDLTKVYSTD

RNB_9C:
                                       (SEQ ID No 19)
LKMFPDLTKVYSTDI

RNB_9D:
                                       (SEQ ID No 20)
KMFPDLTKVYSTDIF

RNB_12A:
                                      (SEQ ID No. 65)
LTLKLYNNGFTSVQG

RNB_12B:
                                      (SEQ ID No. 66)
TLKLYNNGFTSVQGY

RNB_12B-KKK:
                                      (SEQ ID No. 67)
KKK TLKLYNNGFTSVQGYKKK
```

The peptide may comprise the RNB 5A, 5B, 5C, 5D, 5E, 5F, 4J, 4K, 9A, 9B, 9C, 9D, 12A or 12B sequence, or a variant thereof in which one or more amino acids has been replaced by another amino acid, such as K, which has been modified at one or both ends, for example by the introduction of "GKK" or "KKK" sequences.

The peptide may comprise the RNB-5D sequence, or a variant thereof in which one or more amino acids has been replaced by another amino acid, such as K, which has been modified at one or both ends, for example by the introduction of "GKK" or "KKK" sequences.

The present invention also provides a peptide which comprises the sequence:

KK-(G/K)-aa1-(RNB-5D peptide)-aa2-aa3-Z-(G/K)-KK wherein aa1 is no amino acid, I, K or T;

RNB-5D peptide is YVSIDVTLQQLE (SEQ ID NO: 4), or a variant thereof in which one or more amino acids has been replaced by K, aa2 is no amino acid, S or K;

aa3 is no amino acid, H or K which is capable of binding to an MHC molecule in vitro and being presented to a T cell without antigen processing.

In this embodiment, the RNB-5D peptide may be YVSID-VTLQQLE (SEQ ID NO: 4), or a variant thereof in which one, two or three amino acids is/are replaced by K.

The peptide may be selected from the following group, which are all identified as being apitopes (Table 1): KKGI-YVSIDVTLQQLESHGKK (SEQ ID No 12), KKG-KYVSIDVTLQQLESHGKK (SEQ ID No 22), KKGIK-VSIDVTLQQLESHGKK (SEQ ID No 23), KKGIYKSIDVTLQQLESHGKK (SEQ ID No 24), KKGI-YVSIDVKLQQLESHGKK (SEQ ID No 25), KKGI-YVSIDVTLQKLESHGKK (SEQ ID No 26), KKGI-YVSIDVTLQQKESHGKK (SEQ ID No 27), KKGIYVSIDVTLQQLKSHGKK (SEQ ID No 28), KKGI-YVSIDVTLQQLEKHGKK (SEQ ID No 29), KKGI-YVSIDVTLQQLESKGKK (SEQ ID No 30), KKGYVSID-VTLQQLEGKK (SEQ ID No 31), KKGYVSIDVKLQQLEGKK (SEQ ID No 32), KKGYVSIDVTLQKLEGKK (SEQ ID No 33), KKGYVSIDVTLQQEGKK (SEQ ID No 34), KKGYVSIDVKLQKKEGKK (SEQ ID No 35), KKGI-YVSIDVTLQQLEGKK (SEQ ID No 36), KKGIYVSID-VKLQQLEGKK (SEQ ID No 37), KKGIYVSID-VTLQKLEGKK (SEQ ID No 38), KKGIYVSIDVTLQQKEGKK (SEQ ID No 39), KKGI-YVSIDVKLQKKEGKK (SEQ ID No 40), KKGTYVSID-VTLQQLEGKK (SEQ ID No 41), KKGTYVSID-VKLQQLEGKK (SEQ ID No 42), KKGTYVSIDVTLQKLEGKK (SEQ ID No 43), KKG-TYVSIDVTLQQKEGKK (SEQ ID No 44), KKGTYVSID-VKLQKKEGKK (SEQ ID No 45), KKKIYVSID-VTLQQLESHKKK (SEQ ID No 21), KKKKYVSIDVTLQQLESHKKK (SEQ ID No 46), KKKIKVSIDVTLQQLESHKKK (SEQ ID No 47), KKKI-YKSIDVTLQQLESHKKK (SEQ ID No 48), KKKI-YVKIDVTLQQLESHKKK (SEQ ID No 49), KKKI-YVSIDVKLQQLESHKKK (SEQ ID No 50), KKKIYVSIDVTLKQLESHKKK (SEQ ID No 51), KKKI-YVSIDVTLQKLESHKKK (SEQ ID No 52), KKKI-YVSIDVTLQQKESHKKK (SEQ ID No 53), KKKI-YVSIDVTLQQLKSHKKK (SEQ ID No 54), KKKIYVSIDVTLQQLEKHKKK (SEQ ID No 55), KKKI-YVSIDVTLQQLESKKKK (SEQ ID No 56), KKKYVSID-VTLQQLEKKK (SEQ ID No 57), KKKYVSID-VKLQQLEKKK (SEQ ID No 58), KKKYVSIDVTLQKLEKKK (SEQ ID No 59), KKKYVSIDVTLQQKEKKK (SEQ ID No 60), KKKYVSIDVKLQKKEKKK (SEQ ID No. 61).

The peptide may be selected from the following group, which are all identified as apitopes and have improved solubility: KKGKYVSIDVTLQQLESHGKK (SEQ ID No. 22), KKGIYKSIDVTLQQLESHGKK (SEQ ID No. 24), KKGYVSIDVTLQQLEGKK (SEQ ID No. 31), KKGYVSIDVKLQQLEGKK (SEQ ID No. 32), KKGYVSIDVTLQKLEGKK (SEQ ID No. 33), KKGYVSIDVTLQQEGKK (SEQ ID No. 34), KKGYVSIDVKLQKKEGKK (SEQ ID No. 35), KKGI-YVSIDVKLQKKEGKK (SEQ ID No. 40), KKGTYVSID-VKLQQLEGKK (SEQ ID No. 42), KKGTYVSIDVKLQK-KEGKK (SEQ ID No. 45), KKKKYVSIDVTLQQLESHKKK (SEQ ID No. 46), KKKIYKSIDVTLQQLESHKKK (SEQ ID No. 48), KKKI-YVKIDVTLQQLESHKKK (SEQ ID No. 49), KKKYVSIDVTLQQLEKKK (SEQ ID No. 57), KKKYVSIDVKLQQLEKKK (SEQ ID No. 58), KKKYVSIDVTLQQKEKKK (SEQ ID No. 60), KKKYVSIDVKLQKKEKKK (SEQ ID No. 61).

The peptide may be selected from the following group, which are all identified as apitopes and have the best solubility: KKGIYKSIDVTLQQLESHGKK (SEQ ID No. 24), KKGYVSIDVKLQQLEGKK (SEQ ID No 32), KKGYVSIDVTLQKLEGKK (SEQ ID No. 33), KKGYVSIDVTLQQKEGKK (SEQ ID No. 34), KKGYVSIDVKLQKKEGKK (SEQ ID No. 35), KKG-TYVSIDVKLQQLEGKK (SEQ Id No. 42), KKGTYVSID-VKLQKKEGKK (SEQ ID No. 45), KKKKYVSID-VTLQQLESHKKK (SEQ ID No. 46), KKKIYKSIDVTLQQLESHKKK (SEQ ID No. 48), KKKYVSIDVTLQQLEKKK (SEQ ID No. 57), KKKYVSIDVTLQQKEKKK (SEQ ID No. 60).

The following peptides are of particular interest: KKGYVSIDVTLQKLEGKK (SEQ ID No. 32), KKGYVSIDVKLQKKEGKK (SEQ ID No. 34), KKK-KYVSIDVTLQQLESHKKK (SEQ ID No. 46), KKKIYK-SIDVTLQQLESHKKK (SEQ ID No. 48), KKKYVSID-VTLQQLEKKK (SEQ ID No. 57), KKKYVSIDVTLQQKEKKK (SEQ ID No. 60).

In a second aspect, the present invention provides a composition comprising a plurality of peptides, including one or more peptide(s) according to the first aspect of the invention.

In a third aspect, the present invention provides a peptide according to the first aspect of the invention, or a composition according to the second aspect of the invention, for use in supressing or preventing the production of TSHR autoantibodies in vivo.

In a fourth aspect, the present invention provides a peptide according to the first aspect of the invention, or a composition according to the second aspect of the invention, for use in treating and/or preventing Graves' Disease in a subject.

In a fifth aspect, the present invention provides the use of a peptide according to the first aspect of the invention, or a composition according to the second aspect of the invention, in the manufacture of a medicament to suppress or prevent the production of TSHR autoantibodies in vivo.

In a sixth aspect, the present invention provides use of a peptide according to the first aspect of the invention, or a composition according to the second aspect of the invention, in the manufacture of a medicament to treat and/or prevent Graves' Disease.

In a seventh aspect, the present invention provides a method for suppressing or preventing the production of TSHR autoantibodies in a subject, which comprises the step of administration of a peptide according to the first aspect of the invention, or a composition according to the second aspect of the invention, to the subject.

In an eighth aspect, the present invention provides a method for treating Graves' Disease in a subject which comprises the step of administration of a peptide according to the first aspect of the invention, or a composition according to the second aspect of the invention, to the subject.

The subject may be HLA-DR3 or HLA-DR4.

DETAILED DESCRIPTION

Peptides

In a first aspect, the present invention relates to a peptide. The term "peptide" is used in the normal sense to mean a series of residues, typically L-amino acids, connected one to the other, typically by peptide bonds between the a-amino and carboxyl groups of adjacent amino acids. The term includes modified peptides and synthetic peptide analogues.

The peptide of the present invention may be made using chemical methods (Peptide Chemistry, A practical Textbook. Mikos Bodansky, Springer-Verlag, Berlin). For example, peptides can be synthesized by solid phase techniques (Roberge J Y et al (1995) Science 269: 202-204), cleaved from the resin, and purified by preparative high performance liquid chromatography (e.g., Creighton (1983) Proteins Structures And Molecular Principles, WH Freeman and Co, New York N.Y.). Automated synthesis may be achieved, for example, using the ABI 43 1 A Peptide Synthesizer (Perkin Elmer) in accordance with the instructions provided by the manufacturer.

The peptide may alternatively be made by recombinant means, or by cleavage from a longer polypeptide. For example, the peptide may be obtained by cleavage from the thyrotropin receptor protein, which may be followed by modification of one or both ends. The composition of a peptide may be confirmed by amino acid analysis or sequencing (e.g., the Edman degradation procedure).

For practical purposes, there are various other characteristics which the peptide may show. For example, it is important that the peptide is sufficiently stable in vivo to be therapeutically useful. The half-life of the peptide in vivo may be at least 10 minutes, 30 minutes, 4 hours, or 24 hours.

The peptide may also demonstrate good bioavailability in vivo. The peptide may maintain a conformation in vivo which enables it to bind to an MHC molecule at the cell surface without due hindrance.

Apitopes

In an adaptive immune response, T lymphocytes are capable of recognising internal epitopes of a protein antigen. Antigen presenting cells (APC) take up protein antigens and degrade them into short peptide fragments. A peptide may bind to a major histocompatibility complex (MHC) class I or II molecule inside the cell and be carried to the cell surface. When presented at the cell surface in conjunction with an MHC molecule, the peptide may be recognised by a T cell (via the T cell receptor (TCR)), in which case the peptide is a T cell epitope.

An epitope is thus a peptide derivable from an antigen which is capable of binding to the peptide-binding groove of an MHC class I or II molecule and being recognised by a T cell.

The minimal epitope is the shortest fragment derivable from an epitope, which is capable of binding to the peptide-binding grove of an MHC class I or II molecule and being recognised by a T cell. For a given immunogenic region, it is typically possible to generate a "nested set" of overlapping peptides which act as epitopes, all of which contain the minimal epitope but differ in their flanking regions.

By the same token, it is possible to identify the minimal epitope for a particular MHC molecule: T cell combination by measuring the response to truncated peptides. For example, if a response is obtained to the peptide comprising residues 1-15 in the overlapping library, sets which are truncated at both ends (ie. 1-14, 1-13, 1-12 etc. and 2-15, 3-15, 4-15 etc.) can be used to identify the minimal epitope.

The present inventors have previously determined that there is a link between the capacity of a peptide to bind to an MHC class I or II molecule and be presented to a T cell without further processing, and the peptide's capacity to induce tolerance in vivo (WO 02/16410). If a peptide is too long to bind the peptide binding groove of an MHC molecule without further processing (e g trimming), or binds in an inappropriate conformation then it will not be tolerogenic in vivo. If, on the other hand, the peptide is of an appropriate size and conformation to bind directly to the MHC peptide binding groove and be presented to a T cell, then this peptide can be predicted to be useful for tolerance induction.

It is thus possible to investigate the tolerogenic capacity of a peptide by investigating whether it can bind to an MHC class I or II molecule and be presented to a T cell without further antigen processing in vitro.

The peptides of the present invention are apitopes (Antigen Processing-Independent epiTOPES) in that they are capable of binding to an MHC molecule and stimulating a response from TSHR specific T cells without further antigen processing. Such apitopes can be predicted to cause tolerance to TSHR, following the rule-based method described in WO 02/16410.

A peptide of the present invention may be any length that is capable of binding to an MHC class I or II molecule without any further processing. Typically, the peptide of the present invention is capable of binding MHC class II.

Peptides that bind to MHC class I molecules are typically 7 to 13, more usually 8 to 10 amino acids in length. The binding of the peptide is stabilised at its two ends by contacts between atoms in the main chain of the peptide and invariant sites in the peptide-binding groove of all MHC class I molecules. There are invariant sites at both ends of the groove which bind the amino and carboxy termini of the peptide. Variations in peptide length are accommodated by a kinking in the peptide backbone, often at proline or glycine residues that allow flexibility.

Peptides which bind to MHC class II molecules are typically between 8 and 20 amino acids in length, more usually between 10 and 17 amino acids in length, and can be longer (for example up to 40 amino acids). These peptides lie in an extended conformation along the MHC II peptide-binding groove which (unlike the MHC class I peptide-binding groove) is open at both ends. The peptide is held in place mainly by main-chain atom contacts with conserved residues that line the peptide-binding groove.

The peptide of the present invention may comprise between 8 and 30 amino acids, for example 8 to 25 amino acids, 8 to 20 amino acids, 8 to 15 amino acids or 8 to 12 amino acids.

Portion

The peptide of the present invention may comprise all or a portion of the TSHR-derived peptides shown as SEQ ID NOs 1-3.

The term "portion" refers to a peptide that is derived from SEQ ID NOs 1-3 and contains at least a minimal epitope of the peptide.

Such a peptide may comprise one or more mutations, typically amino acid substitutions within the TSHR-derived sequence. The amino acid may be substituted for an amino acid such as glycine, lysine or glutamic acid. The peptide may comprise up to three, up to two or one amino acid substitution from the TSHR-derived sequence.

Such a peptide may comprise amino acids at one or both ends which are not derivable from the TSHR sequence. For example, the peptide may have one or more glycine and/or lysine and/or glutamic acid residues at one or both ends. For example, the additional amino acids may comprise a glycine or lysine spacer, followed by the amino acid pairs KK, KE, EK or EE at one or both ends.

For example, the peptide may have the following formula: KKG-TSHR-derived portion-GKK.

The peptide, including the non-TSHR derived amino acids, must be an apitope, i.e. capable of binding to an MHC molecule in vitro and presented to a T cell without antigen processing.

Thyroid Stimulating Hormone Receptor (TSHR)

GD is an autoimmune disease caused by auto-reactive T and B lymphocytes targeting the primary auto-antigen, the Thyroid Stimulating Hormone Receptor (TSHR).

TSHR is a G-protein coupled receptor on thyroid follicular cells in the thyroid gland that stimulates the production of thyroxine (T4) and triiodothyronine (T3) via a cAMP signal cascade upon binding of its ligand, the thyroid-stimulating hormone (TSH). Upon internalization, degradation and presentation of the TSHR by APCs, T cells become activated and interact with auto-reactive B cells, which in turn produce stimulating agonistic auto-antibodies directed against TSHR. The thyroid-stimulating immunoglobulins bind to the same receptor pocket as the TSH, activating the TSHR mediated signal transduction and leading to the production of excess thyroid hormone from the thyroid gland and thyroid growth.

TSHR, also known as thyrotropin receptor, is primarily expressed on thyroid epithelial cells.

The TSHR holoreceptor has 764 residues and comprises an N-terminal extracellular domain, to which TSH binds, a serpentine (or transmembrane domain) and a C-terminal intracellular domain TSHR comprises a large extracellular domain (418 amino acids) with highly conserved Cys residues, which facilitate the formation of an extracellular domain tertiary structure that may be important in both ligand binding and inactive receptor conformation. The extracellular domain comprises over half the total protein length and is sufficient for high-affinity ligand binding. After being transported to the cell surface the receptor molecule is subjected to intra-molecular cleavage, leading to the removal of a 50 amino acid sequence between residues 316 and 366. As a result the receptor comprises two subunits, the a subunit comprising the extracellular ligand-binding domain and the β subunit comprising the transmembrane domain and the short C-terminal sequence, bound together with disulphide bonds. In subsequent steps, the a subunit is shed, leading to an excess of ligand-binding domain deprived β subunits on the cell membrane.

Following the binding of circulating TSH to TSHR, a G-protein signaling cascade activates adenylyl cyclase and intercellular levels of cAMP rise. cAMP activates all functional aspects of the thyroid cell, including iodine pumping, thyroglobulin synthesis, iodination, endocytosis and proteolysis, thyroid peroxidase activity and hormone release.

The amino acid sequence of mature TSHR is given below (SEQ ID NO: 5).

```
  1 mrpadllqlv llldlprdlg gmgcssppce chqeedfrvt ckdiqripsl ppstqtlkli
 61 ethlrtipsh afsnlpnisr iyvsidvtlq qleshsfynl skvthieirn trnltyidpd
121 alkelpllkf lgifntglkm fpdltkvyst diffileitd npymtsipvn atqglcnetl
181 tlklynngft svqgyafngt kldavylnkn kyltvidkda tggvysgpsl ldvsqtsvta
241 lpskglehlk eliarntwtl kklplslsfl hltradlsyp shccafknqk kirgileslm
301 cnessmqslr qrksvnalns plhqeyeenl gdsivgykek skfqdthnna hyyvffeeqe
361 deiigfgqel knpqeetlqa fdshydytic gdsedmvctp ksdefnpced imgykflriv
421 vwfvsllall gnvfvllill tshyklnvpr flmcnlafad fcmgmyllli asvdlythse
481 yynhaidwqt gpgcntagff tvfaselsvy tltvitlerw yaitfamrld rkirlrhaca
541 imvggwvccf llallplvgi ssyakvsicl pmdtetplal ayivfvltln ivafvivccc
601 yvkiyitvrn pqynpgdkdt kiakrmavli ftdficmapi sfyalsailn kplitvsnsk
661 illvlfypln scanpflyai ftkafqrdvf illskfgick rqaqayrgqr vppknstdiq
721 vqkvthdmrq glhnmedvye lienshltpk kqgqiseeym qtvl
```

The peptide of the invention is at least partially derivable from TSHR. The peptide or portion thereof may be derivable from a region of 64-92, 78-106, 107-135, 136-164 or 201-229 of TSHR. The peptide or portion thereof may be derivable from a fragment of the antigen which arises by natural processing of the antigen by an antigen presenting cell.

Region 64-92 of TSHR (RNB_4) has the following sequence:

(SEQ ID No 2)
LRTIPSHAFSNLPNISRIYVSIDVTLQQL

The peptide may comprise the minimal epitope from the following peptide:

TSHR 73-87 (RNB_4J):
(SEQ ID No 15)
SNLPNISRIYVSIDV

TSHR 73-87 (RNB_4J-GKK):
(SEQ ID No 16)
KKGSNLPNISRIYVSIDVGKK

The peptide may comprise the minimal epitope from the following peptide:

TSHR 74-88 (RNB_4K):
(SEQ ID No. 62)
NLPNISRIYVSIDVT

TSHR 74-88 (RNB_4K-GKK):
(SEQ ID No. 63)
KKGNLPNISRIYVSIDVTGKK

Region 78-106 of TSHR (RNB_5) has the following sequence:

```
                                    (SEQ ID No 1)
ISRIYVSIDVTLQQLESHSFYNLSKVTHI
```

The peptide may comprise the minimal epitope from the following peptides: TSHR 78-92 (RNB_5A), 79-93 (RNB_5B), 80-94 (RNB_5C), 81-95 (RNB_5D), 82-96 (RNB_5E) and 83-97 (RNB_5F).

The sequences of TSHR 78-92, 79-93, 80-94, 81-95, 82-96 and 83-97 are:

```
TSHR 78-92 (RNB_5A):
                                    (SEQ ID No 6)
ISRIYVSIDVTLQQL

TSHR 79-93 (RNB_5B):
                                    (SEQ ID No 7)
SRIYVSIDVTLQQLE

TSHR 80-94 (RNB_5C):
                                    (SEQ ID No 8)
RIYVSIDVTLQQLES

TSHR 81-95 (RNB_5D):
                                    (SEQ ID No 9)
IYVSIDVTLQQLESH

TSHR 82-96 (RNB_5E):
                                   (SEQ ID No 10)
YVSIDVTLQQLESHS

TSHR 83-97 (RNB_5F):
                                   (SEQ ID No 11)
VSIDVTLQQLESHSF

TSHR 81-95 (RNB_5D-GKK):
                                   (SEQ ID No 12)
KKGIYVSIDVTLQQLESHGKK

TSHR 81-95 (RNB_5D-KKK):
                                  (SEQ ID No. 21)
KKKIYVSIDVTLQQLESHKKK

TSHR 82-96 (RNB_5E-GKK):
                                   (SEQ ID No 13)
KKGYVSIDVTLQQLESHSGKK

TSHR 83-97 (RNB_5F-GKK):
                                   (SEQ ID No 14)
KKGVSIDVTLQQLESHSFGKK
```

Region 136-164 (RNB_9) of TSHR has the following sequence:

```
                                    (SEQ ID No 3)
TGLKMFPDLTKVYSTDIFFILEITDNPYM
```

The peptide may comprise the minimal epitope from the following peptides: TSHR 136-150 (RNB_9A), 137-151 (RNB_9B), 138-152 (RNB_9C) and 139-153 (RNB_9D).

The sequences of TSHR 136-150, 137-151, 138-152 and 139-153 are:

```
TSHR 136-150 (RNB_9A):
                                   (SEQ ID No 17)
TGLKMFPDLTKVYST

TSHR 137-151 (RNB_9B):
                                   (SEQ ID No 18)
GLKMFDLTKVYSTD
```

-continued

```
TSHR 138-152 (RNB_9C):
                                   (SEQ ID No 19)
LKMFPDLTKVYSTDI

TSHR 139-153 (RNB_9D):
                                   (SEQ ID No 20)
KMFPDLTKVYSTDIF
```

Region 180-207 of TSHR (RNB_12) has the following sequence:

```
                                   (SEQ ID No 64)
LTLKLYNNGFTSVQGYAFNGTKLDAVYL
```

The peptide may comprise the minimal epitope from one the peptides shown in the following table:

| | | | SEQ ID No. |
|---|---|---|---|
| RNB-12 | A | LTLKLYNNGFTSVQG | 65 |
| | B | TLKLYNNGFTSVQGY | 66 |
| | C | LKLYNNGFTSVQGYA | 68 |
| | D | KLYNNGFTSVQGYAF | 69 |
| | E | LYNNGFTSVQGYAFN | 70 |
| | F | YNNGFTSVQGYAFNG | 71 |
| | G | NNGFTSVQGYAFNGT | 72 |
| | H | NGFTSVQGYAFNGTK | 73 |
| | I | GFTSVQGYAFNGTKL | 74 |
| | J | FTSVQGYAFNGTKLD | 75 |
| | K | TSVQGYAFNGTKLDA | 76 |
| | L | SVQGYAFNGTKLDAV | 77 |
| | M | VQGYAFNGTKLDAVY | 78 |

The peptide may comprise the minimal epitope from one the following peptides:

```
                                  (SEQ ID No. 65)
TSHR 180-194 (RNB_12A): LTLKLYNNGFTSVQG (SEQ ID No. 66)
TSHR 180-194 (RNB_12B): TLKLYNNGFTSVQGY (SEQ ID No. 67)
TSHR 180-194 (RNB_12B-KKK): KKKTLKLYNNGFTSVQGYKKK.
```

The present invention also provides a peptide which comprises the sequence:

KK-(G/K)-aa1-(RNB-5D peptide)-aa2-aa3-Z-(G/K)-KK wherein aa1 is no amino acid, I, K or T;

RNB-5D peptide is YVSIDVTLQQLE (SEQ ID NO: 4), or a variant thereof in which one or more amino acids has been replaced by K, aa2 is no amino acid, S or K;

aa3 is no amino acid, H or K which is capable of binding to an MHC molecule in vitro and being presented to a T cell without antigen processing.

In this embodiment, the RNB-5D peptide may be YVSIDVTLQQLE (SEQ ID NO: 4), or a variant thereof in which one, two or three amino acids is/are replaced by K.

The peptide may be selected from the following group, which are all identified as being apitopes (Table 1): KKGI- YVSIDVTLQQLESHGKK (SEQ ID No 12), KKG-KYVSIDVTLQQLESHGKK (SEQ ID No 22), KKGIK-VSIDVTLQQLESHGKK (SEQ ID No 23), KKGIYKSIDVTLQQLESHGKK (SEQ ID No 24), KKGI-YVSIDVKLQQLESHGKK (SEQ ID No 25), KKGI-YVSIDVTLQKLESHGKK (SEQ ID No 26), KKGI-YVSIDVTLQQKESHGKK (SEQ ID No 27), KKGIYVSIDVTLQQLKSHGKK (SEQ ID No 28), KKGI-YVSIDVTLQQLEKHGKK (SEQ ID No 29), KKGI-YVSIDVTLQQLESKGKK (SEQ ID No 30), KKGYVSID-VTLQQLEGKK (SEQ ID No 31), KKGYVSIDVKLQQLEGKK (SEQ ID No 32), KKGYVSIDVTLQKLEGKK (SEQ ID No 33), KKGYVSIDVTLQQKEGKK (SEQ ID No 34), KKGYVSIDVKLQKKEGKK (SEQ ID No 35), KKGI-YVSIDVTLQQLEGKK (SEQ ID No 36), KKGIYVSID-VKLQQLEGKK (SEQ ID No 37), KKGIYVSID-VTLQKLEGKK (SEQ ID No 38), KKGIYVSIDVTLQQKEGKK (SEQ ID No 39), KKGI-YVSIDVKLQKKEGKK (SEQ ID No 40), KKGTYVSID-VTLQQLEGKK (SEQ ID No 41), KKGTYVSID-VKLQQLEGKK (SEQ ID No 42), KKGTYVSIDVTLQKLEGKK (SEQ ID No 43), KKG-TYVSIDVTLQQKEGKK (SEQ ID No 44), KKGTYVSID-VKLQKKEGKK (SEQ ID No 45), KKKIYVSID-VTLQQLESHKKK (SEQ ID No 21), KKKKYVSIDVTLQQLESHKKK (SEQ ID No 46), KKKIKVSIDVTLQQLESHKKK (SEQ ID No 47), KKKI-YKSIDVTLQQLESHKKK (SEQ ID No 48), KKKI-YVKIDVTLQQLESHKKK (SEQ ID No 49), KKKI-YVSIDVKLQQLESHKKK (SEQ ID No 50), KKKIYVSIDVTLKQLESHKKK (SEQ ID No 51), KKKI-YVSIDVTLQKLESHKKK (SEQ ID No 52), KKKI-YVSIDVTLQQKESHKKK (SEQ ID No 53), KKKI-YVSIDVTLQQLKSHKKK (SEQ ID No 54), KKKIYVSIDVTLQQLEKHKKK (SEQ ID No 55), KKKI-YVSIDVTLQQLESKKKK (SEQ ID No 56), KKKYVSID-VTLQQLEKKK (SEQ ID No 57), KKKYVSID-VKLQQLEKKK (SEQ ID No 58), KKKYVSIDVTLQKLEKKK (SEQ ID No 59), KKKYVSIDVTLQQKEKKK (SEQ ID No 60), KKKYVSIDVKLQKKEKKK (SEQ ID No. 61).

The peptide may be selected from the following group, which are all identified as apitopes and have improved solubility: KKGKYVSIDVTLQQLESHGKK (SEQ ID No. 22), KKGIYKSIDVTLQQLESHGKK (SEQ ID No. 24), KKGYVSIDVTLQQLEGKK (SEQ ID No. 31), KKGYVSIDVKLQQLEGKK (SEQ ID No. 32), KKGYVSIDVTLQKLEGKK (SEQ ID No. 33), KKGYVSIDVTLQQKEGKK (SEQ ID No. 34), KKGYVSIDVKLQKKEGKK (SEQ ID No. 35), KKGI-YVSIDVKLQKKEGKK (SEQ ID No. 40), KKGTYVSID-VKLQQLEGKK (SEQ ID No. 42), KKGTYVSIDVKLQK-KEGKK (SEQ ID No. 45), KKKKYVSIDVTLQQLESHKKK (SEQ ID No. 46), KKKIYKSIDVTLQQLESHKKK (SEQ ID No. 48), KKKI-YVKIDVTLQQLESHKKK (SEQ ID No. 49), KKKYVSIDVTLQQLEKKK (SEQ ID No. 57), KKKYVSIDVKLQQLEKKK (SEQ ID No. 58), KKKYVSIDVTLQQKEKKK (SEQ ID No. 60), KKKYVSIDVKLQKKEKKK (SEQ ID No. 61).

The peptide may be selected from the following group, which are all identified as apitopes and have the best solubility: KKGIYKSIDVTLQQLESHGKK (SEQ ID No. 24), KKGYVSIDVKLQQLEGKK (SEQ ID No 32), KKGYVSIDVTLQKLEGKK (SEQ ID No. 33), KKGYVSIDVTLQQKEGKK (SEQ ID No. 34), KKGYVSIDVKLQKKEGKK (SEQ ID No. 35), KKG-TYVSIDVKLQQLEGKK (SEQ Id No. 42), KKGTYVSID-VKLQKKEGKK (SEQ ID No. 45), KKKKYVSID-VTLQQLESHKKK (SEQ ID No. 46), KKKIYKSIDVTLQQLESHKKK (SEQ ID No. 48), KKKYVSIDVTLQQLEKKK (SEQ ID No. 57), KKKYVSIDVTLQQKEKKK (SEQ ID No. 60). The following peptides are of particular interest: KKGYVSID-VTLQKLEGKK (SEQ ID No. 32), KKGYVSIDVKLQK-KEGKK (SEQ ID No. 34), KKKKYVSIDVTLQQLESHKKK (SEQ ID No. 46), KKKIYKSIDVTLQQLESHKKK (SEQ ID No. 48), KKKYVSIDVTLQQLEKKK (SEQ ID No. 57), KKKYVSIDVTLQQKEKKK (SEQ ID No. 60).

Tolerance

T cell epitopes play a central role in the adaptive immune response to any antigen, whether self or foreign. The central role played by T cell epitopes in hypersensitivity diseases (which include allergy, autoimmune diseases and transplant rejection) has been demonstrated through the use of experimental models. It is possible to induce inflammatory or allergic diseases by injection of synthetic peptides (based on the structure of T cell epitopes) in combination with adjuvant.

By contrast, it has been shown to be possible to induce immunogenic tolerance towards particular antigens by administration of peptide epitopes in soluble form. Administration of soluble peptide antigens has been demonstrated as an effective means of inhibiting disease in experimental autoimmune encephalomyelitis (EAE—a model for multiple sclerosis (MS)) (Metzler and Wraith (1993) Int. Immunol. 5:1159-1165; Liu and Wraith (1995) Int. Immunol. 7:1255-1263; Anderton and Wraith (1998) Eur. J. Immunol. 28:1251-1261); and experimental models of arthritis, diabetes, and uveoretinitis (reviewed in Anderton and Wraith (1998) as above). This has also been demonstrated as a means of treating an ongoing disease in EAE (Anderton and Wraith (1998) as above).

Tolerance is the failure to respond to an antigen. Tolerance to self antigens is an essential feature of the immune system, when this is lost, autoimmune disease can result. The adaptive immune system must maintain the capacity to respond to an enormous variety of infectious agents while avoiding autoimmune attack of the self antigens contained within its own tissues.

This is controlled to a large extent by the sensitivity of immature T lymphocytes to apoptotic cell death in the thymus (central tolerance). However, not all self antigens are detected in the thymus, so death of self-reactive thymocytes remains incomplete. There are thus also mechanisms by which tolerance may be acquired by mature self-reactive T lymphocytes in the peripheral tissues (peripheral tolerance). A review of the mechanisms of central and peripheral tolerance is given in Anderton et al (1999) (*Immunological Reviews* 169:123-137).

GD is currently believed to be caused by TSHR stimulating autoantibodies that bind to and activate the TSHR, thereby stimulating thyroid hormone synthesis and secretion, and thyroid growth. The peptides of the present invention are capable of inducing tolerance to TSHR, such that when administered to a subject, they may reinstate tolerance to the TSHR self-protein and curtail the pathogenic immune response.

Tolerance may result from or be characterised by the induction of anergy in at least a portion of CD4+ T cells. In order to activate a T cell, a peptide must associate with a "professional" APC capable of delivering two signals to T cells. The first signal (signal 1) is delivered by the MHC-peptide complex on the cell surface of the APC and is received by the T cell via the TCR. The second signal (signal 2) is delivered by costimulatory molecules on the surface of the APC, such as CD80 and CD86, and received by CD28 on the surface of the T cell. It is thought that when a T cell receives signal 1 in the absence of signal 2, it is not activated and, in fact, becomes anergic. Anergic T cells are refractory to subsequent antigenic challenge, and may be capable of suppressing other immune responses. Anergic T cells are thought to be involved in mediating T cell tolerance.

Peptides which require processing before they can be presented in conjunction with MHC molecules do not induce tolerance because they have to be handled by mature antigen presenting cells. Mature antigen presenting cells (such as macrophages, B cells and dendritic cells) are capable of antigen processing, but also of delivering both signals 1 and 2 to a T cell, leading to T cell activation. Apitopes, on the other hand, will be able to bind class II MHC on immature APC. Thus they will be presented to T cells without co-stimulation, leading to T cell anergy and tolerance.

Of course, apitopes are also capable of binding to MHC molecules at the cell surface of mature APC. However, the immune system contains a greater abundance of immature than mature APC (it has been suggested that less than 10% of dendritic cells are activated, Summers et al. (2001) Am. J. Pathol. 159: 285-295). The default position to an apitope will therefore be anergy/tolerance, rather than activation.

It has been shown that, when tolerance is induced by peptide inhalation, the capacity of antigen-specific CD4+ T cells to proliferate is reduced. Also, the production of IL-2, IFN-γ and IL-4 production by these cells is down-regulated, but production of IL-10 is increased. Neutralisation of IL-10 in mice in a state of peptide-induced tolerance has been shown to restore completely susceptibility to disease. It has been proposed that a population of regulatory cells persist in the tolerant state which produce IL-10 and mediate immune regulation (Burkhart et al (1999) Int. Immunol. 11:1625-1634).

The induction of tolerance to TSHR can be monitored in vivo by looking for a reduction in the level of:
 i) TSHR autoantibodies;
 ii) CD4+ T cells specific for TSHR; and/or
 iii) B cells capable of secreting TSHR autoantibodies
by techniques known in the art.

The induction of tolerance can therefore also be monitored by various techniques including:
 (a) the induction of anergy in CD4+ T cells (which can be detected by subsequent challenge with antigen in vitro);
 (b) changes in the CD4+ T cell population, including
  (i) reduction in proliferation;
  (ii) down-regulation in the production of IL-2, IFN-γ and IL-4; and
  (iii) increase in the production of IL-10.

As used herein, the term "tolerogenic" means capable of inducing tolerance.

Composition

The present invention also relates to a composition, such as a pharmaceutical composition comprising one or more peptide(s) according to the first or second aspect of the invention.

The peptide may comprise a plurality of peptides, for example two, three, four, five or six peptides.

The composition of the present invention may be for prophylactic or therapeutic use.

When administered for prophylactic use, the composition may reduce or prevent the generation of an immune response to TSHR. The level of immune response is less than would be obtained if the patient had not been treated the composition. The term "reduce" indicates that a partial reduction in immune response is observed, such as a 50%, 70%, 80% or 90% reduction in the response that would have been observed if the patient had not been treated with the composition (or in the response observed in an untreated patient over the same time-period). The term "prevent" indicates that no appreciable immune response to TSHR is observed.

When administered for therapeutic use, the composition may suppress an already on-going immune response to TSHR. The term "suppress" indicates a reduction in the level of an on-going immune response, compared to the level before peptide treatment, or the levels which would have been observed at the same time point had the treatment not been given.

Treatment with the composition of the present invention may cause a reduction in level of any or all of the following:
 i) TSHR autoantibodies
 ii) CD4+ T cells specific for TSHR
 iii) B cells secreting TSHR autoantibodies.

Detection of all of the factors can be carried out by techniques known in the art, such as ELISA, flow cytometry etc.

Treatment with the composition of the present invention may also or alternatively cause anergy in CD4+ T cells specific for TSHR. Anergy can be detected by, for example, subsequent challenge with TSHR in vitro.

Where there are two or more apitopes, the pharmaceutical composition may be in the form of a kit, in which some or each of the apitopes are provided separately for simultaneous, separate or sequential administration.

Alternatively (or in addition) if the pharmaceutical composition (or any part thereof) is to be administered in multiple doses, each dose may be packaged separately.

Also, in the pharmaceutical compositions of the present invention, the or each apitope may be admixed with any suitable binder(s), lubricant(s), suspending agent(s), coating agent(s), or solubilising agent(s).

Formulation

The composition may by prepared as an injectable, either as liquid solution or suspension; solid form suitable for solution in, or suspension in, liquid prior to injection may also be prepared. The preparation may also be emulsified, or the peptides encapsulated in liposomes. The active ingredients may be mixed with excipients which are pharmaceutically acceptable and compatible with the active ingredient. Suitable excipients are, for example, water, saline (for example, phosphate-buffered saline), dextrose, glycerol, ethanol, or the like and combinations thereof.

In addition, if desired, the composition may contain minor amounts of auxiliary substances such as wetting or emulsifying agents and/or pH buffering agents. Buffering salts include phosphate, citrate, acetate, hydrochloric acid and/or sodium hydroxide may be used for pH adjustment. For stabilisation, disaccharides may be used such as sucrose or trehalose.

If the composition comprises a plurality of peptides, the relative ratio of the peptides may be approximately equal. Alternatively the relative ratios of each peptide may be altered, for example, to focus the tolerogenic response on a particular sub-set of autoreactive T-cells or if it is found that one peptide works better than the others in particular HLA types.

After formulation, the composition may be incorporated into a sterile container which is then sealed and stored at a low temperature, for example 4° C., or it may be freeze-dried.

Conveniently the composition is prepared as a lyophilized (freeze dried) powder. Lyophilisation permits long-term storage in a stabilised form. Lyophilisation procedures are well known in the art, see for example http://www.device-link.com/ivdt/archive/97/01/006.html. Bulking agents are commonly used prior to freeze-drying, such as mannitol, dextran or glycine.

The composition may be administered in a convenient manner such as by the oral, intravenous (where water soluble), intramuscular, subcutaneous, sublingual, intranasal, intradermal or suppository routes or implanting (e.g. using slow release molecules).

The composition may advantageously be administered via intranasal, subcutaneous or intradermal routes.

The peptide and composition of the invention may be used to treat a human subject. The subject may have GD. The subject may have TSHR autoantibodies.

The subject may be an HLA-haplotype which is associated with a predisposition to develop inhibitory THSR autoantibodies. The subject may express HLA-DR3 or HLA-DR4. Methods for determining the HLA haplotype of an individual are known in the art.

Typically, a physician will determine the actual dosage which will be most suitable for an individual subject and it will vary with the age, weight and response of the particular patient.

In a preferred embodiment a "dose escalation" protocol may be followed, where a plurality of doses is given to the patient in ascending concentrations. Such an approach has been used, for example, for phospholipase A2 peptides in immunotherapeutic applications against bee venom allergy (Müller et al (1998) J. Allergy Clin Immunol. 101:747-754 and Akdis et al (1998) J. Clin. Invest. 102:98-106).

Kits

Conveniently, if the composition comprises a plurality of peptides, they may be administered together, in the form of a mixed composition or cocktail. However, there may be circumstances in which it is preferable to provide the peptides separately in the form of a kit, for simultaneous, separate, sequential or combined administration.

The kit may also comprise mixing and/or administration means (for example a vapouriser for intranasal administration; or a syringe and needle for subcutaneous/intradermal dosing). The kit may also comprise instructions for use.

The pharmaceutical composition or kit of the invention may be used to treat and/or prevent a disease.

In particular, the composition/kit may be used to treat and/or prevent GD.

EXAMPLES

Example 1—Selection of HLA-DR3 TSHR Peptides

To identify important epitope regions in the TSHR, the ECD of the TSHR (AA20-418) was divided in 28 overlapping peptides of 28-30 amino acids (28-30-mers) overlapping by 15 amino acids, as shown below.

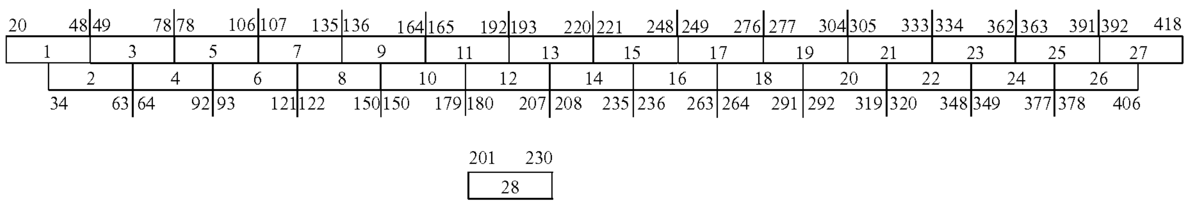

| Name | Length (AA) | Sequence | SEQ ID NO |
|---|---|---|---|
| RNB-1 | 29 | GGMGCSSPPCECHQEEDFRVTCKDIQRIP | 79 |
| RNB-2 | 30 | EEDFRVTCKDIQRIPSLPPSTQTLKLIETH | 80 |
| RNB-3 | 30 | SLPPSTQTLKLIETHLRTIPSHAFSNLPNI | 81 |
| RNB-4 | 29 | LRTIPSHAFSNLPNISRIYVSIDVTLQQL | 2 |
| RNB-5 | 29 | ISRIYVSIDVTLQQLESHSFYNLSKVTHI | 1 |
| RNB-6 | 29 | ESHSFYNLSKVTHIEIRNTRNLTYIDPDA | 82 |
| RNB-7 | 29 | EIRNTRNLTYIDPDALKELPLLKFLGIFN | 83 |
| RNB-8 | 29 | LKELPLLKFLGIFNTGLKMFPDLTKVYST | 84 |
| RNB-9 | 29 | TGLKMFPDLTKVYSTDIFFILEITDNPYM | 3 |
| RNB-10 | 30 | TDIFFILEITDNPYMTSIPVNAFQGLCNET | 85 |
| RNB-11 | 28 | TSIPVNAFQGLCNETLTLKLYNNGFTSV | 86 |
| RNB-12 | 28 | LTLKLYNNGFTSVQGYAFNGTKLDAVYL | 64 |

| Name | Length (AA) | Sequence | SEQ ID NO |
|---|---|---|---|
| RNB-13 | 28 | QGYAFNGTKLDAVYLNKNKYLTVIDKDA | 87 |
| RNB-14 | 28 | NKNKYLTVIDKDAFGGVYSGPSLLDVSQ | 88 |
| RNB-15 | 28 | FGGVYSGPSLLDVSQTSVTALPSKGLEH | 89 |
| RNB-16 | 28 | TSVTALPSKGLEHLKELIARNTWTLKKL | 90 |
| RNB-17 | 28 | LKELIARNTWTLKKLPLSLSFLHLTRAD | 91 |
| RNB-18 | 28 | PLSLSFLHLTRADLSYPSHCCAFKNQKK | 92 |
| RNB-19 | 28 | LSYPSHCCAFKNQKKIRGILESLMCNES | 83 |
| RNB-20 | 28 | IRGILESLMCNESSMQSLRQRKSVNALN | 94 |
| RNB-21 | 29 | SMQSLRQRKSVNALNSPLHQEYEENLGDS | 95 |
| RNB-22 | 29 | SPLHQEYEENLGDSIVGYKEKSKFQDTHN | 96 |
| RNB-23 | 29 | IVGYKEKSKFQDTHNNAHYYVFFEEQEDE | 97 |
| RNB-24 | 29 | NAHYYVFFEEQEDEIIGFGQELKNPQEET | 98 |
| RNB-25 | 29 | IIGFGQELKNPQEETLQAFDSHYDYTICG | 99 |
| RNB-26 | 29 | LQAFDSHYDYTICGDSEDMVCTPKSDEFN | 100 |
| RNB-27 | 27 | DSEDMVCTPKSDEFNPCEDIMGYKFLR | 101 |
| RNB-28 | 29 | KLDAVYLNKNKYLTVIDKDAFGGVYSGPS | 102 |

The immunogenicity of all peptides was then evaluated by immunizing HLA-DRB1*0301 transgenic mice (DR3 mice) with 200 µg of a pool of 3 peptides emulsified in CFA. After 10 days, LN cells and splenocytes were isolated and stimulated in vitro with 10-25 µg/mL of the corresponding individual peptides. Based on the stimulation indexes (SI; 3H-thymidine incorporation (counts per minute) of peptide-stimulated cells divided by that of non-stimulated cells), peptides RNB-5 and RNB-9 were found to be highly immunogenic (SI>10).

FIG. 1 shows that LN and splenocytes, isolated from RNB-5 immunized mice, strongly respond to RNB-5 stimulation in vitro.

All examples described here will focus on peptide RNB-5.

Example 2—Identification of Apitopes within RNB-5

To determine the exact epitope position within RNB-5, a panel of 15-mer overlapping peptides spanning RNB-5 was synthesized using standard F-moc chemistry. Each peptide was displaced by 1 amino acid, as shown below:

| Name | Sequence | SEQ ID NO |
|---|---|---|
| RNB_5A | ISRIYVSIDVTLQQL | 6 |
| RNB_5B | SRIYVSIDVTLQQLE | 7 |
| RNB_5C | RIYVSIDVTLQQLES | 8 |
| RNB_5D | IYVSIDVTLQQLESH | 9 |
| RNB_5E | YVSIDVTLQQLESHS | 10 |
| RNB_5F | VSIDVTLQQLESHSF | 11 |
| RNB_5G | SIDVTLQQLESHSFY | 103 |
| RNB_5H | IDVTLQQLESHSFYN | 104 |
| RNB_5I | DVTLQQLESHSFYNL | 105 |
| RNB_5J | VTLQQLESHSFYNLS | 106 |
| RNB_5K | TLQQLESHSFYNLSK | 107 |
| RNB_5L | LQQLESHSFYNLSKV | 108 |
| RNB_5M | QQLESHSFYNLSKVT | 109 |
| RNB_5N | QLESHSFYNLSKVTH | 110 |
| RNB_5O | LESHSFYNLSKVTHI | 111 |

| Name | Modified sequence | SEQ ID NO |
|---|---|---|
| RNB_5D-GKK = RNB_5D_G0 | KKGIYVSIDVTLQQLESHGKK | 12 |

-continued

| Name | Modified sequence | SEQ ID NO |
|---|---|---|
| RNB_5E-GKK | KKGYVSIDVTLQQLESHSGKK | 13 |
| RNB_5F-GIKK | KKGVSIDVTLQQLESHSFGKK | 14 |
| RNB_5D_KKK = RNB_5D_K0 | KKKIYVSIDVTLQQLESHKKK | 21 |
| RNB_5D_G1 | KKGKYVSIDVTLQQLESHGKK | 22 |
| RNB_5D_G2 | KKGIKVSIDVTLQQLESHGKK | 23 |
| RNB_5D_G3 | KKGIYKSIDVTLQQLESHGKK | 24 |
| RNB_5D_G4 | KKGIYVKIDVTLQQLESHGKK | 112 |
| RNB_5D_G5 | KKGIYVSKDVTLQQLESHGKK | 113 |
| RNB_5D_G6 | KKGIYVSIKVTLQQLESHGKK | 114 |
| RNB_5D_G7 | KKGIYVSIDKTLQQLESHGKK | 115 |
| RNB_5D_G8 | KKGIYVSIDVKLQQLESHGKK | 25 |
| RNB_5D_G9 | KKGIYVSIDVTKQQLESHGKK | 116 |
| RNB_5D_G10 | KKGIYVSIDVTLKQLESHGKK | 117 |
| RNB_5D_G11 | KKGIYVSIDVTLQKLESHGKK | 26 |
| RNB_5D_G12 | KKGIYVSIDVTLQQKESHGKK | 27 |
| RNB_5D_G13 | KKGIYVSIDVTLQQLKSHGKK | 28 |
| RNB_5D_G14 | KKGIYVSIDVTLQQLEKHGKK | 29 |
| RNB_5D_G15 | KKGIYVSIDVTLQQLESKGKK | 30 |
| RNB_5D_G16 | KKGYVSIDVTLQQLEGKK | 31 |
| RNB_5D_G17 | KKGYVSIDVKLQQLEGKK | 32 |
| RNB_5D_G18 | KKGYVSIDVTLQKLEGKK | 33 |
| RNB_5D_G19 | KKGYVSIDVTLQQKEGKK | 34 |
| RNB_5D_G20 | KKGYVSIDVKLQKKEGKK | 35 |
| RNB_5D_G21 | KKGIYVSIDVTLQQLEGKK | 36 |
| RNB_5D_G22 | KKGIYVSIDVKLQQLEGKK | 37 |
| RNB_5D_G23 | KKGIYVSIDVTLQKLEGKK | 38 |
| RNB_5D_G24 | KKGIYVSIDVTLQQKEGKK | 39 |
| RNB_5D_G25 | KKGIYVSIDVKLQKKEGKK | 40 |
| RNB_5D_G26 | KKGTYVSIDVTLQQLEGKK | 41 |
| RNB_5D_G27 | KKGTYVSIDVKLQQLEGKK | 42 |
| RNB_5D_G28 | KKGTYVSIDVTLQKLEGKK | 43 |
| RNB_5D_G29 | KKGTYVSIDVTLQQKEGKK | 44 |
| RNB_5D_G30 | KKGTYVSIDVKLQKKEGKK | 45 |
| RNB_5D_K1 | KKKKYVSIDVTLQQLESHKKK | 46 |
| RNB_5D_K2 | KKKIKVSIDVTLQQLESHKKK | 47 |
| RNB_5D_K3 | KKKIYKSIDVTLQQLESHKKK | 48 |
| RNB_5D_K4 | KKKIYVKIDVTLQQLESHKKK | 49 |
| RNB_5D_K5 | KKKIYVSKDVTLQQLESHKKK | 118 |

-continued

| Name | Modified sequence | SEQ ID NO |
|---|---|---|
| RNB_5D_K6 | KKKIYVSIKVTLQQLESHKKK | 119 |
| RNB_5D_K7 | KKKIYVSIDKTLQQLESHKKK | 120 |
| RNB_5D_K8 | KKKIYVSIDVKLQQLESHKKK | 50 |
| RNB_5D_K9 | KKKIYVSIDVTKQQLESHKKK | 121 |
| RNB_5D_K10 | KKKIYVSIDVTLKQLESHKKK | 51 |
| RNB_5D_K11 | KKKIYVSIDVTLQKLESHKKK | 52 |
| RNB_5D_K12 | KKKIYVSIDVTLQQKESHKKK | 53 |
| RNB_5D_K13 | KKKIYVSIDVTLQQLKSHKKK | 54 |
| RNB_5D_K14 | KKKIYVSIDVTLQQLEKHKKK | 55 |
| RNB_5D_K15 | KKKIYVSIDVTLQQLESKKKK | 56 |
| RNB_5D_K16 | KKKYVSIDVTLQQLEKKK | 57 |
| RNB_5D_K17 | KKKYVSIDVKLQQLEKKK | 58 |
| RNB_5D_K18 | KKKYVSIDVTLQKLEKKK | 59 |
| RNB_5D_K19 | KKKYVSIDVTLQQKEKKK | 60 |
| RNB_5D_K20 | KKKYVSIDVKLQKKEKKK | 61 |

Figure 2:
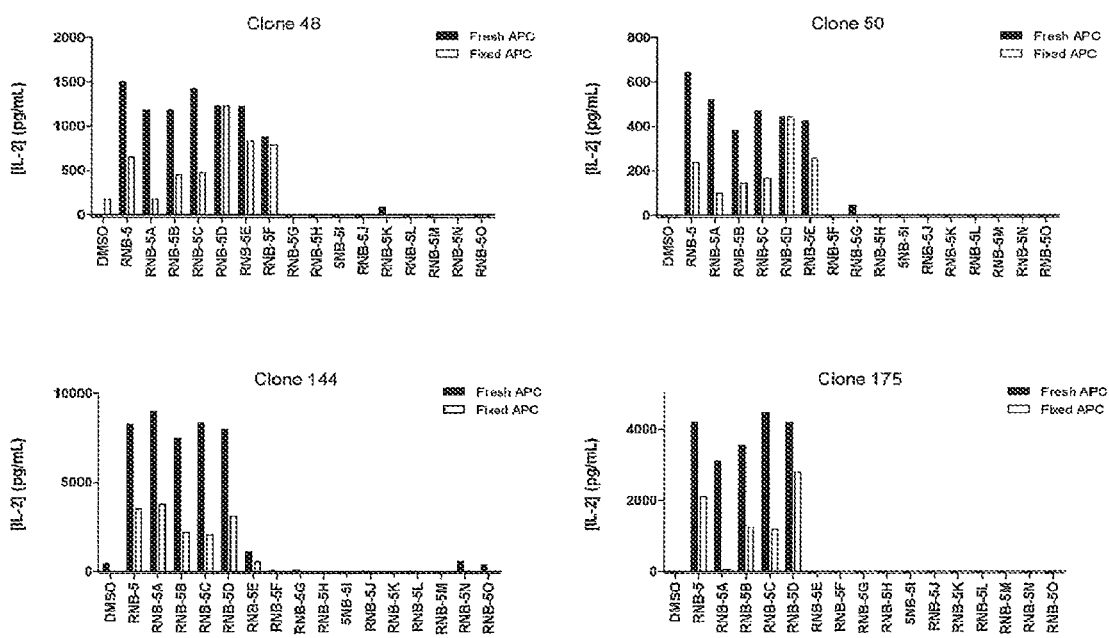
FIG. 2: Identification of apitopes within RNB-5. DR3 mice were immunized with RNB-5/CFA and hybridomas were generated. $5 \times 10^4$ TSHR-specific hybridoma cells were cultured with $5 \times 10^4$ fresh (black bars) or fixed (white bars) VAVY cells and 25 μg/mL antigen (RNB-5 or RNB-5 nested peptide). Representative clones are shown. After 48 h, antigen-induced IL-2 production was measured. The graph represents the mean of a duplicate measurement and results are representative of 2 independent experiments. APC, antigen presenting cell.

First, the peptides were analysed using hybridomas generated from DR3 mice. Hybridomas specific for TSHR and RNB-5 were shown to react to RNB-5 A-F presented by both fresh and fixed VAVY cells. Antigen-induced IL-2 production of representative clones is shown in FIG. 2.

To determine the ability of these 15-mer peptides to bind to HLA-DR molecule, 2 software tools were used: NetMHCII (http://www.cbs.dtu.dk/services/NetMHCII) and Immune Epitope DataBase (http://tools.immuneepitope.org/analyze/html/mhc_II_binding.html). Using both methods, nested peptides RNB-5A up to RNB-5F were identified as strong binders to both HLA-DRB1*0301 and HLA-DRB1*0401 molecules.

Figure 3:
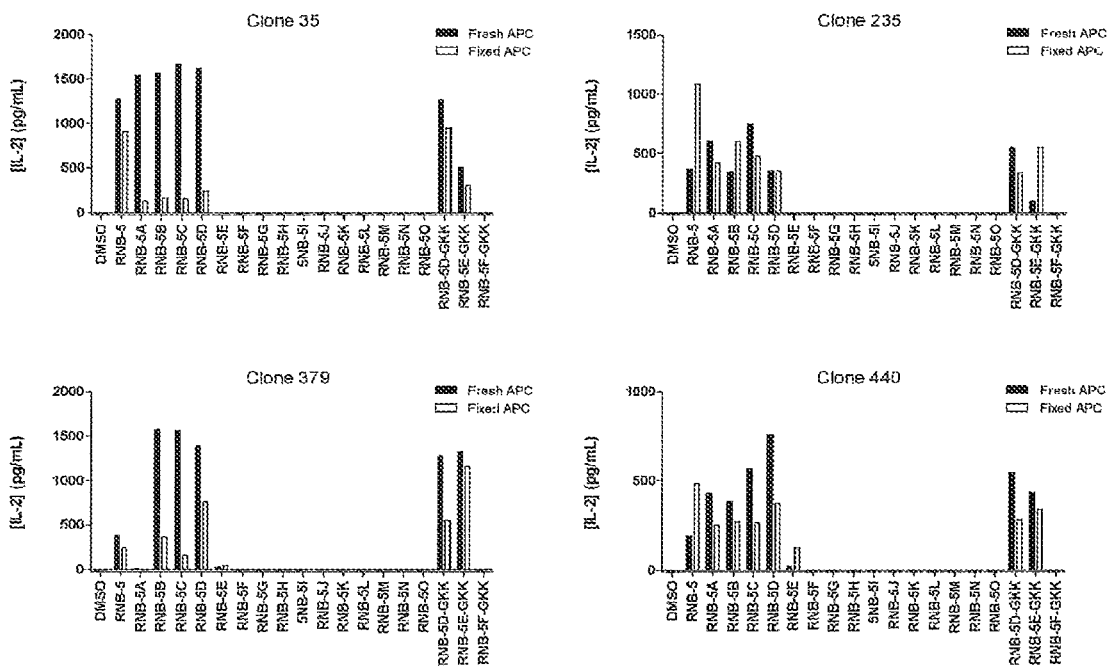
FIG. 3: Identification of apitopes within RNB-5. DR4 mice were immunized with TSHR/CFA and hybridomas were generated. $5 \times 10^4$ TSHR-specific hybridoma cells were cultured with $5 \times 10^4$ fresh (black bars) or fixed (white bars) BM14 cells and 25 μg/mL antigen (TSHR, RNB-5 or RNB-5 nested peptide). Representative clones are shown. After 48 h, antigen-induced IL-2 production was measured. The graph represents the mean of a duplicate measurement. APC, antigen presenting cell.

Although GD in humans is strongly associated with the HLA-DRB1*0301 haplotype, the HLA-DRB1*0401 haplotype often occurs in GD patients as well. Since RNB-5A to 5F peptides were predicted to bind to HLA-DRB1*0401 molecules, RNB-5 was tested for its ability to generate an immune response in DR4 mice in vivo. LN cells and splenocytes isolated from RNB-5/CFA-immunized DR4 mice showed strong immune responses when stimulated with RNB-5 nested peptides. In addition, the RNB-5 specific hybridomas, generated in DR3 mice, respond to the RNB-5 nested peptides when presented by BM14-cells (HLA-DRB1*0401). Therefore, new hybridomas were generated by immunizing DR4 mice with TSHR/CFA. Hybridomas specific for both TSHR protein and RNB-5 peptide were selected to identify apitopes within RNB-5. Peptides RNB-5A to 5F were identified as apitopes again (FIG. 3). The RNB-5 DEF nested peptides were modified by adding amino acids 'GKK' on both the C- and N-terminus. TSHR- and RNB-5 specific hybridomas also react to these modified peptides when presented by both fresh and fixed APCs. Taken together, these data emphasize that this region is interesting for GD patients with either HLA-DRB 1*0301 or HLA-DRB 1*0401 haplotype.

Figure 4A:
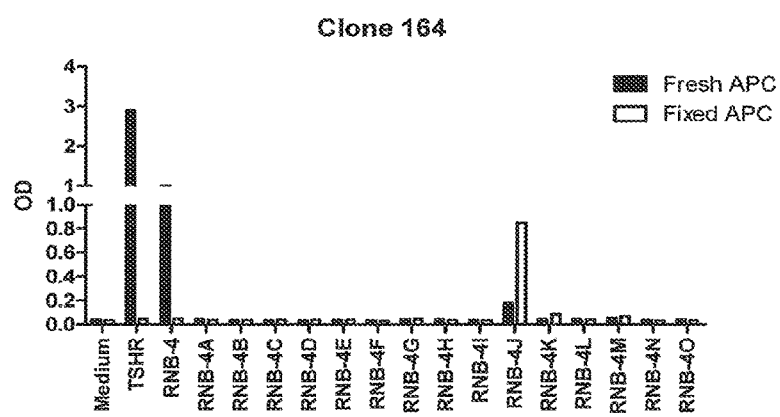
FIG. 4A: Identification of apitopes within RNB-4. DR4 mice were immunized with TSHR-CFA and hybridomas were generated. $5 \times 10^4$ TSHR-specific hybridoma cells were cultured with $5 \times 10^4$ fresh (black bars) or fixed (white bars) BM14 cells and 25 μg/mL antigen (TSHR, RNB-4 or RNB-4 nested peptide). A representative clone is shown. After 48 h, antigen-induced IL-2 production was measured and shown as OD values. The graph represents the mean of a duplicate measurement and results are representative of 3 independent measurements. APC, antigen presenting cell.
Figure 4B:
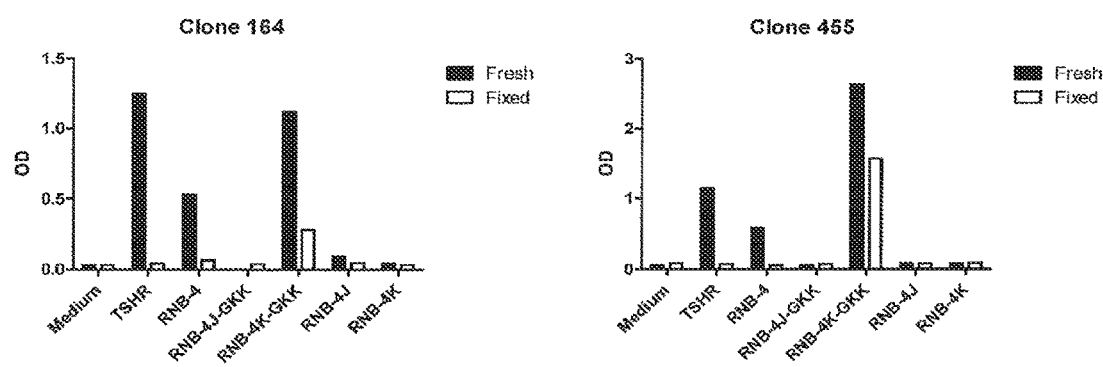
FIG. 4B: Identification of apitopes within RNB-4. DR4 mice were immunized with TSHR/CFA and hybridomas were generated. $5 \times 10^4$ TSHR-specific hybridoma cells were cultured with $5 \times 10^4$ fresh (black bars) or fixed (white bars) BM14 cells and antigen (25 μg/mL TSHR of RNB-4; 100 μg/mL RNB-4 nested peptides). After 48 h, antigen-induced IL-2 production was measured and shown as OD values.

Part of the TSHR-specific hybridomas generated by immunizing DR4 mice with TSHR/CFA were shown to bind to RNB-4 instead of RNB-5, indicating the presence of other immunogenic regions within the TSHR. RNB-4 specific hybridomas were selected to identify apitopes within RNB-4. Peptide RNB-4J was identified as an apitope (FIG. 4). The RNB-4 nested peptide sequences are shown in the table below.

| Name | Sequence | SEQ ID NO |
|---|---|---|
| RNB_4A | LRTIPSHAFSNLPNI | 122 |
| RNB_4B | RTIPSHAFSNLPNIS | 123 |
| RNB_4C | TIPSHAFSNLPNISR | 124 |
| RNB_4D | IPSHAFSNLPNISRI | 125 |
| RNB_4E | PSHAFSNLPNISRIY | 126 |
| RNB_4F | SHAFSNLPNISRIYV | 127 |
| RNB_4G | HAFSNLPNISRIYVS | 128 |
| RNB_4H | AFSNLPNISRIYVSI | 129 |
| RNB_4I | FSNLPNISRIYVSID | 130 |
| RNB_4J | SNLPNISRIYVSIDV | 15 |
| RNB_4K | NLPNISRIYVSIDVT | 62 |
| RNB_4L | LPNISRIYVSIDVTL | 131 |
| RNB_4M | PNISRIYVSIDVTLQ | 132 |
| RNB_4N | NISRIYVSIDVTLQQ | 133 |

| Name | Modified sequence | SEQ ID NO |
|---|---|---|
| RNB_4J-GKK | KKGSNLPNISRIYVSIDVGKK | 16 |
| RNB_4K-GKK | KKGNLPNISRIYVSIDVTGKK | 63 |

Figure 20:
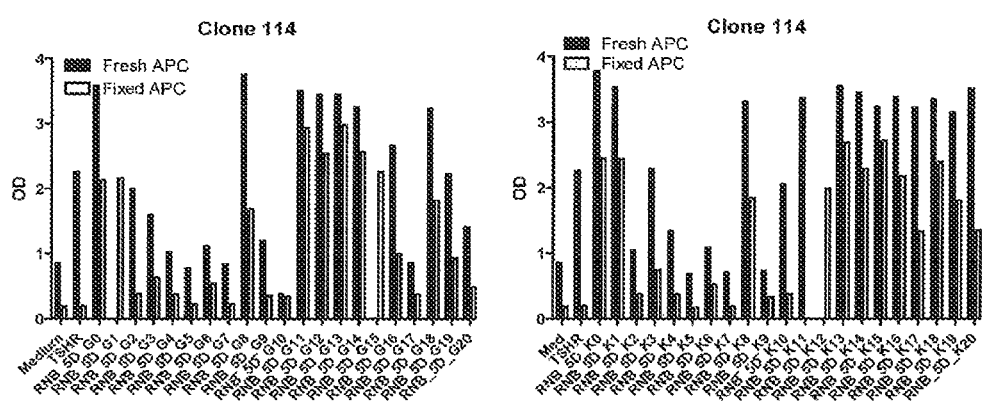
FIG. 20: Graph illustrating the apitope status of RNB5D modified peptides. An example of the response of a TSHR- and RNB-5-specific hybridoma clone, isolated from HLA-DR3 and HLA-DR4 mice immunized with TSHR/CFA, to RNB-5D modified peptides. The hybridoma clone was cultured with fresh (black bars) and fixed (white bars) APCs and 25 µg/ml antigen for 48 hours prior to determination of IL-2 production.

The apitope status of RNB-5D modified peptides was also investigated (FIG. 20).

In addition to the RNB-4 and RNB-5 apitopes, the in silico prediction software tools also identified peptides RNB-9A to 9D as strong binders to HLA-DRB1*0301 molecules. The peptide sequences are shown in the table below.

| Name | Sequence | SEQ ID NO |
|---|---|---|
| RNB_9A | TGLKMFPDLTKVYST | 17 |
| RNB_9B | GLKMFPDLTKVYSTD | 18 |
| RNB_9C | LKMFPDLTKVYSTDI | 19 |
| RNB_9D | KMFPDLTKVYSTDIF | 20 |

The response of TSHR- and RNB-5-specific hybridoma clones, isolated from HLA-DR3 or HLA-DR4 mice immunized with TSHR/CFA, to RNB-5D modified peptides was tested. The results are shown in FIGS. 11 to 15.

Example 3—Ex Vivo Tolerance Assay

To assess the ability of the RNB-5 apitopes to induce tolerance, the ability of these apitopes to inhibit the immune response was first investigated in healthy HLA-DRB1*0301 or HLA-DRB1*0401 mice ex vivo. Mice were pretreated with different RNB-5 apitopes according to the high-dose or the dose-escalation schedule, as described in the method section. The studies showed that pre-treatment with RNB-5 apitopes significantly reduce TSHR-induced T cell proliferation, both in DR3 and DR4 mice (FIG. 6A-D). RNB-5 DEF nested peptides were modified by adding amino acids 'GKK' on both the C- and N-terminus. Pre-treatment with these modified apitopes also significantly reduced TSHR-induced T cell proliferation (FIG. 6E-F).

Peptides RNB-9A to 9D were predicted to bind strongly to HLA-DRB1*0301 molecules and their ability to induce specific immune tolerance was also investigated. DR3 mice were pretreated with RNB-9A to 9D according to the dose-escalation schedule. RNB-9B and 9C pre-treatment caused a significant reduction in TSHR-induced T cell proliferation in both LN and splenocyte cells (FIG. 7).

Peptide RNB 4K-GKK was also shown to significantly reduce TSHR-induced T cell proliferation in DR4 mice (FIG. 16).

The RNB-5D modified peptides also significantly reduced TSHR-induced T cell proliferation. Representative experiments with RNB5D-K1, RNB5D-K3 and RNB5D-K16 are shown in FIG. 19.

Example 4—Animal Model for GD

To investigate the ability of RNB-5 apitopes to reduce GD-like symptoms in mice, two different animal models for GD were developed.

First, C57/Bl6 mice were immunized with TSHR/CFA to induce anti-TSHR antibody production. To investigate whether a boost immunization would further increase the anti-TSHR antibody levels, one group of mice received a second immunization 4 weeks later with TSHR/IFA. Anti-TSHR antibody levels in sera of mice immunized once reach a plateau level 2 weeks after immunization. A second immunization causes a strong increase in anti-TSHR antibody levels (FIG. 8).

Second, Balb/c mice were injected with LacZ-Ad or TSHR-Ad viral particles to induce hyperthyroidism, cause by the action of anti-TSHR antibodies on the thyroid. T4 hormone levels and total IgG anti-TSHR antibody titers were measured in the sera of all mice before, 4 weeks after and 10 weeks after the first injection with adenoviral vectors (FIG. 9). Immunizing mice with $10^{10}$ TSHR-Ad viral particles induced hyperthyroidism in 3/7 mice and 1/7 mice when measured 4 weeks and 10 weeks after the first immunization, respectively. This indicates that T4 levels in 2 mice were normalized during the experiment Immunizing mice with $10^{11}$ TSHR-Ad viral particles induced hyperthyroidism in 1/6 mice, both at 4 weeks and 10 weeks after the first immunization. Here, one mouse being hyperthyroid at 4 weeks had normal T4 levels at 10 weeks, while T4 levels of another mouse strongly increased between 4 and 10 weeks. Anti-TSHR antibody levels were measured as total IgG values, without determining their stimulating or blocking effect on the TSHR (FIG. 10). Immunizing mice with TSHR-Ad viral particles clearly induced anti-TSHR antibody production. Mice immunized with $10^{10}$ or $10^{11}$ TSHR-Ad viral particles produced significantly more antibodies than LacZ-Ad immunized mice. Anti-TSHR antibody levels did not differ between the $10^{10}$-TSHR-Ad and $10^{11}$-TSHR-Ad immunized mice. No correlation was found between total IgG anti-TSHR antibody levels and T4 levels.

These animal models are used to investigate whether RNB-5 apitopes can reduce the GD-like symptoms in vivo.

Example 5—Identification of Apitopes in the RNB12 Region

The RNB12 as well as the nested peptides are not immunogenic in mice. Therefore the region was identified by the reactivity of a T cell line generated from Graves' disease patients. FIG. 17 shows the results obtained from such a T cell line.

RNB12 and the modified peptide RNB12-KKK were confirmed to be apitopes (FIG. 18).

Materials and Methods

Mice

HLA-DRB1*0301 transgenic mice (DR3 mice) were bred and maintained in the Immunogenetics mouse colony of Mayo Clinic. HLA DR3-tg founder mice were obtained from Gunter Hammerling (German Cancer Research Center, Heidelberg, Germany). Briefly, a 6-kb NdeI fragment of a HLA DRA genomic clone in pUC and a 24-kb ClaIxSalI fragment of cos 4.1 containing the B gene were coinjected into fertilized eggs from (C57BL/6xDBA/2)-F1 donors mated with C57BL/6 males. The transgenic mice were bred on to I-Ab knockout mice. DR3 mice were bred on to C57BL/10 background for 10 generations. These DR3 mice express the HLA-DRB1*0301 molecule but not the mouse MHC-II molecule.

The DR4 mouse strain was originally created by Lars Fugger et al (PNAS 1994; volume 91:6151-6155) in that a HLA-DRA*0101/HLA-DRB1*0101 and mCD3-huCD4c/g constructs were co-microinjected into embryos from (DBA/1xA.CA)F1 matings and viable embryos were transferred into pseudopregnant female (Balb/c x 129)F1 for development to term. The offspring has later been bred into the IA-b knockout C57BL/6 genetic background (ABO mice) lacking mouse MHC class II molecule expression. The only MHC class II molecule expressed in these DR4 mice is therefore the human HLA DR4 molecule.

Animal studies were approved by the 'Ethical Committee for Animal experiments' (ECD) at Hasselt University and performed with the highest standards of care in a pathogen-free facility.

Peptides

Peptides were synthesised by GL Biochem Ltd (Shangai, China) and stored in dimethyl sulfoxide (DMSO; Sigma-Aldrich, Bornem, Belgium) at −80° C.

Investigation of Peptides Binding to HLA-DRB1*0301

NetMHCII 2.2 Server

NetMHCII 2.2 server predicts binding of peptides to HLA-DRB1*0301 using artificial neuron networks. The prediction values are given in nM IC50 values. Strong and weak binding peptides are indicated in the output. High affinity binding peptides have an IC50 value below 50 nM, and weak binding peptides an IC50 values below 500 nM. The result is presented as prediction score which is calculated as follows: 1−log 50000(aff). Website address: http://www.cbs.dtu.dk/services/NetMHCII.

Immune Epitope DataBase (IEDB): Consensus Method

For each peptide, a percentile rank for each of the four methods (ARB, combinatorial library, SMM_align and Sturniolo) was generated by comparing the peptide's score against the scores of five million random 15-mers selected from SWISSPROT database. A small numbered percentile rank indicates high affinity. The median percentile rank of the four methods was then used to generate the rank for consensus method. Website address: http://tools.immuneepitope.org/analyze/html/mhc_II_binding.html.

Determination of Immunogenicity of the Long Peptides

Priming

DR3 mice were injected subcutaneously at the base of the tail with 100 μg of antigen in PBS (Lonza, Verviers, Belgium) emulsified with Complete Freund Adjuvant ((CFA; BD Benelux, Erembodegem, Belgium) containing 4 mg/ml *Mycobacterium tuberculosis* (MTb, BD Benelux)) (100 μl/injection). Depending on the experiment, RNB peptides or full-length TSHR-289 protein were used as antigen. Control animals were injected at the same time with PBS/CFA alone.

Cell Culture

Ten days after immunization, draining lymph nodes (LN) and spleen were harvested. LN cells and splenocytes were isolated and cultured in X-vivo 15 medium (supplemented with glutamine, penicillin and streptomycin; Lonza) in 96-well flat bottom plates. To investigate antigen-induced cell proliferation, $0.5 \times 10^6$ cells/well were cultured (200 μl/well) for 72 hours with different antigen concentrations (0-25 μg/ml) or with 12.5 μg/ml purified protein derivative (PPD; priming control; Statens serum institut, Copenhagen, Denmark).

Proliferation Assay and Cytokine Analysis

After 72 hours, 60 μL of cell supernatant was harvested and frozen. 20 μL/well of tritiated thymidine (PerkinElmer, Zaventem, Belgium) were then added to the cells to obtain a final concentration of 1 μCi/well. The cells were incubated at 37° C., and after 16 h, plates were frozen. Thawed plates were harvested and read with β-counter (Wallac 1450 Microbeta Trilux Liquid Scintillation Counter) to assess the cell proliferation. The thawed supernatant was analysed with the mouse Th1/Th2 10plex FlowCytomix Multiplex (Bender MedSystems, Vienna, Austria) to measure the antigen-induced cytokine production.

Generation of RNB-5 Specific Hybridomas

Priming and T Cell Line Establishment

On day 0, mice were injected subcutaneously at the base of the tail with 100 μg antigen/CFA (RNB-5 for DR3 mice; TSHR for DR4 mice). Control mice were immunized with PBS/CFA. On day 10, the draining LNs and spleens were removed and single-cell suspensions were generated. Some of the cells were used to measure antigen-induced cell proliferation, as described above. The remaining splenocytes and LN cells were mixed and CD4$^+$ T-cells were isolated using a negative purification kit (untouched CD4$^+$ T-cells; Miltenyi, Leiden, The Netherlands). CD4$^+$ T-cells were then cultured together with antigen (25 μg/ml RNB-5 or 0.5 μg/ml TSHR-289 protein) and irradiated splenocytes (3000 rad) from DR3 mice (APC:CD4$^+$ T-cell ratio 1:1; $5 \times 10^6$ cells/ml). Cells were cultured in X-vivo 15 medium to avoid foetal calf serum (FCS)-induced cell activation. On day 4, 20 U/ml of recombinant human IL-2 (R&D, Abingdon, United Kingdom) was added to the cells. On day 7, living cells were harvested by eliminating dead cells using Ficoll density gradient separation (Histopaque 1083, Sigma-Aldrich). Cells were then restimulated as described above, changing the APC: CD4$^+$ T-cell ratio to 2:1. On day 9, living cells were harvested and some of them were used for fusion. The remaining CD4$^+$ T-cells were left in culture and IL-2 was added on day 10. On day 14, living cells were harvested, restimulated with antigen in the presence of APC (ratio of APC:CD4$^+$ T-cells at 3:1), and used for a second fusion on day 16.

Fusion $1 \times 10^7$ BW5147 cells (Health Protection Agency Culture Collections, Salisbury, UK) and $5 \times 10^6$ CD4$^+$ T-cells were mixed in a 50 ml tube and washed in 37° C. serum free medium. After centrifugation, the cell pellet was gently resuspended. 1 ml of 37° C. polyethylene glycol (PEG; 40-50% solution, Sigma-Aldrich) was added over 45 sec, keeping the cells in a small 37° C. water bath. The cells were incubated at 37° C. for 45 sec. Then, 1 ml of 37° C. serum free medium was added over 30 sec while swirling, followed by 2, 3, 4, 10 and 30 ml consecutively. The tube was inverted very slowly and incubated at 37° C. for 4 min. Cells were centrifuged for 5 min at 1300 rpm at room temperature (RT) without brake. The supernatant was removed and 50 ml of RT serum free medium was slowly added to avoid dislodging the cell pellet. The washing step was repeated with complete medium. Finally, cells were resuspended in RT complete medium with 10%-FCS and plated at different cell concentrations in 96-well flat bottom plates (100 μl/well). After 48 h, cells were cultured in 1× hypoxanthine-aminopterin-thymidine (HAT, Sigma-Aldrich) medium and hybridoma cell growth was detected after approximately 6 days. Clones were maintained in HAT medium until they were stable, then weaned via Hypoxanthine-thymidine (HT, Sigma-Aldrich) medium to complete RPMI medium. At a regular base, clones were frozen in freezing medium (90% FCS+10% DMSO).

Assessment of Antigen-Specificity of Clones

Hybridoma cells were cultured with $5 \times 10^4$ VAVY or BM14 cells (human cell line expressing HLA-DRB1*0301 or HLA-DRB1*0401, respectively; International Histocompatibility Working group, Seattle, USA) and antigen (10-25 μg/ml). After 48 h, antigen-induced IL-2 production was measured by enzyme-linked immunosorbent assay (ELISA).

IL-2 ELISA 96-well plates (Immunosorb 96 well, Fisher Scientific, Erembodegem, Belgium) were coated overnight at 4° C. with 50 μl/well purified rat anti-mouse IL-2 capture Ab (BD Biosciences, Oxford, UK), diluted 1:250 in carbonate buffer. After 2 washes with PBS-0.05% Tween, wells were blocked with 10% FCS/PBS for 1 hour at RT. Then, wells were incubated with 50 µl of cell culture supernatant or IL-2 standard (BD Biosciences, Belgium, Erembodegem) for 2 h at RT. Wells were incubated with 50 µl/well of biotin rat anti-mouse IL-2 (BD Biosciences) diluted 1:1000 in 10% FCS/PBS for 1 h at RT, followed by incubation with 50 µl/well extravidin peroxidase (Sigma-Aldrich) diluted 1:1000 in PBS for 30 min at RT. To detect antibody-binding, 50 µl/well of TMB substrate solution (Perbio Science, Erembodegem, Belgium) was added. After 11 min, the color reaction was stopped using 50 µl/well 2M $H_2SO_4$. Optical density (OD) was measured at 450 nm (630 nm ref) (Tecan Benelux, Mechelen, Belgium).

Antigen Processing Independent Presentation System

Antigen-specific clones were tested for their reactivity to the 15-mer peptides (RNB-5A to 50), presented by fixed or not fixed VAVY or BM14 cells (=APCs). $5 \times 10^4$ cells from the individual clones were cultured with 25 µg/ml peptide and $5 \times 10^4$ fixed or fresh APCs. To fixate APCs, cells were incubated with 0.5% paraformaldehyde (Merck, Darmstadt, Germany) (pH7) for 5 min at RT. The fixation reaction was stopped by adding 0.4M glycine (Sigma-Aldrich) and washing the cells in RPMI-10% FCS. Additionally, reactivity towards human TSHR-289 protein (Chesapeake-PERL, Savage, Md., USA) was measured to identify cryptic epitopes. After 48 h, antigen-induced IL-2 production was measured by ELISA.

Assessment of RNB-5 Apitope Solubility

Solubility of the peptides was analysed by Anabiotec (Zwijnaarde, Belgium). In short, peptide samples were dissolved at two different target concentrations (1 mg/ml and 4 mg/ml) by adding PBS pH 7.0±0.1. The peptide solutions were incubated at RT for at least 16 hours. Turbidity was measured at 320 and 360 nm, before and after centrifugation. Peptide concentration was determined by using absorbance at 280 and 205 nm and by HPLC-UV.

Peptides were dissolved at stock concentration of 20 mg/mL in DMSO. Dilution series of target concentrations 4, 2 and 1 mg/mL were prepared in PBS. The peptide solutions were incubated at RT for 16-17 hours to allow any precipitate to form. Turbidity was scored by visual observation and adsorbance was measured at 205 nm, 280 nm and 320 nm using a Nanodrop device. Peptide solutions were centrifugated at 14800 rpm for 10 minutes and visual observation and adsorbance measurements were repeated. Peptide concentration was calculated using the following formula:

$$\text{Concentration}\left(\frac{mg}{mL}\right) = \frac{A_{280}(\text{no units}) \times \text{Molecular Weight}(Da)}{\text{Extinction Coefficient }(\varepsilon_{280})(M_{-1}cm_{-1}) \times l(cm)}$$

Tolerance Induction with RNB-5 Apitope Treatment

Figure 5A:
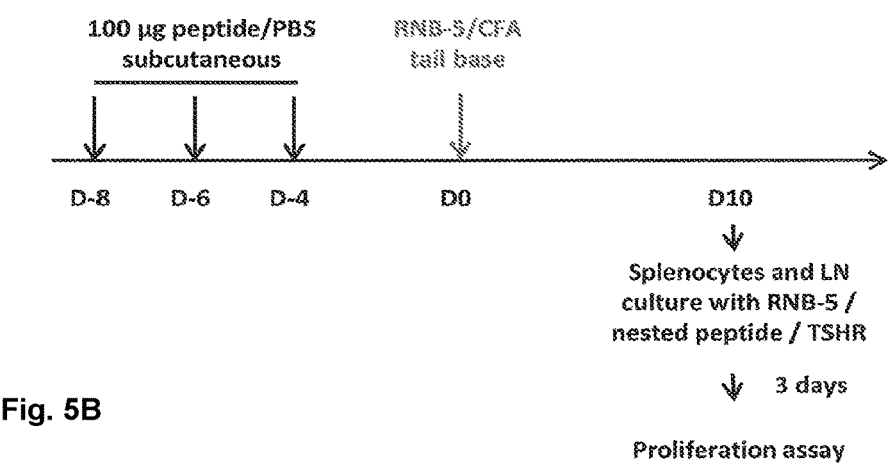
FIG. 5A-5B: Ex vivo tolerisation protocol.
Figure 5B:
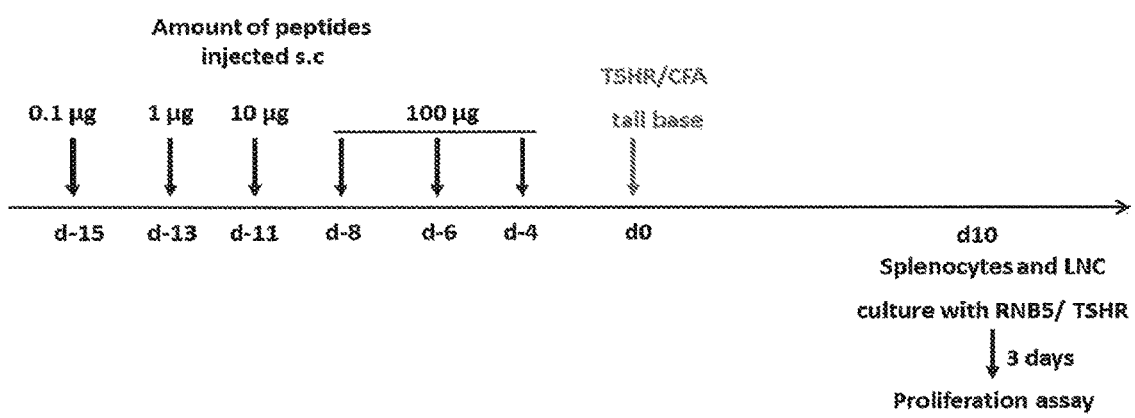
Figure 6:
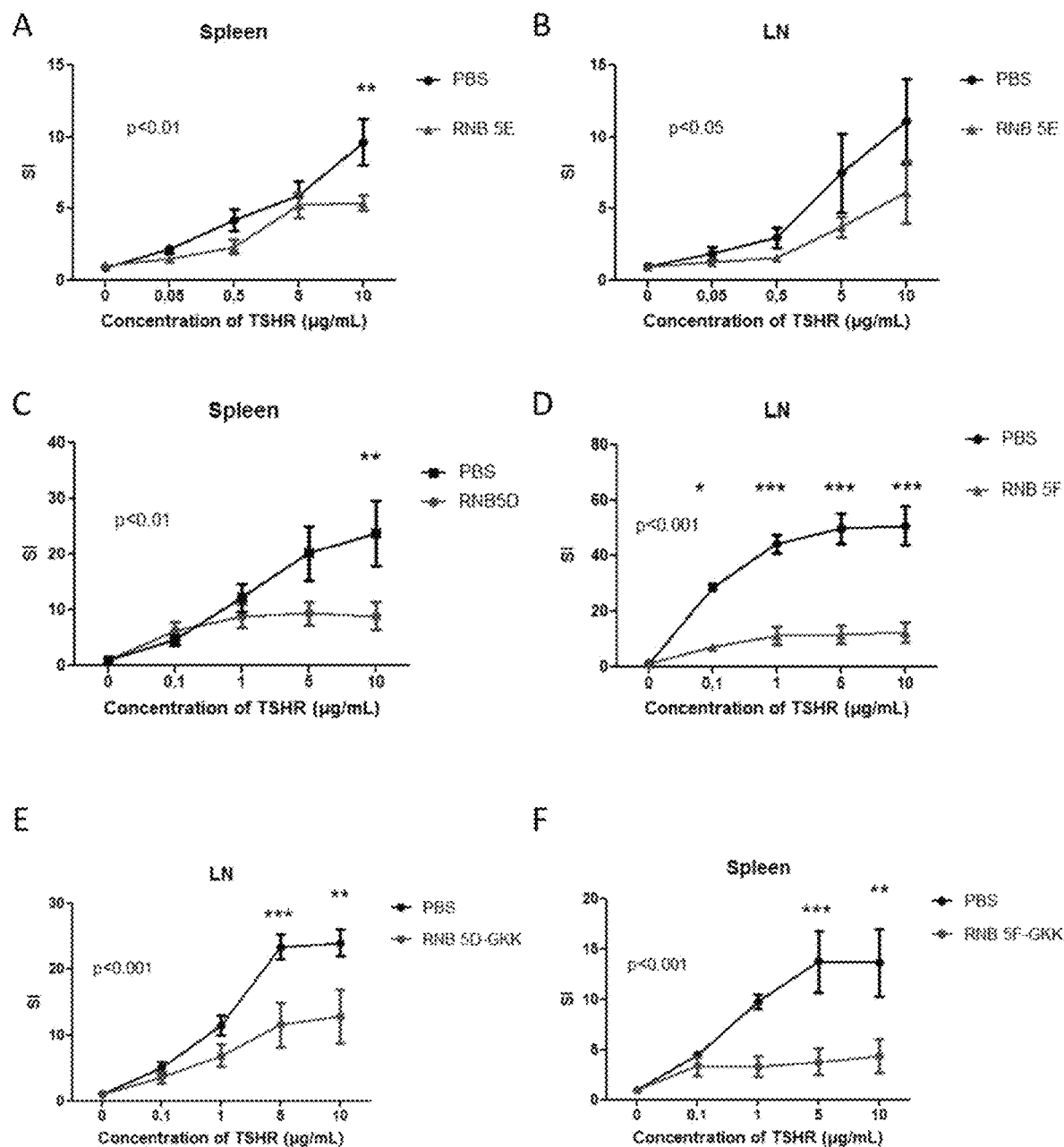
Figure 7:
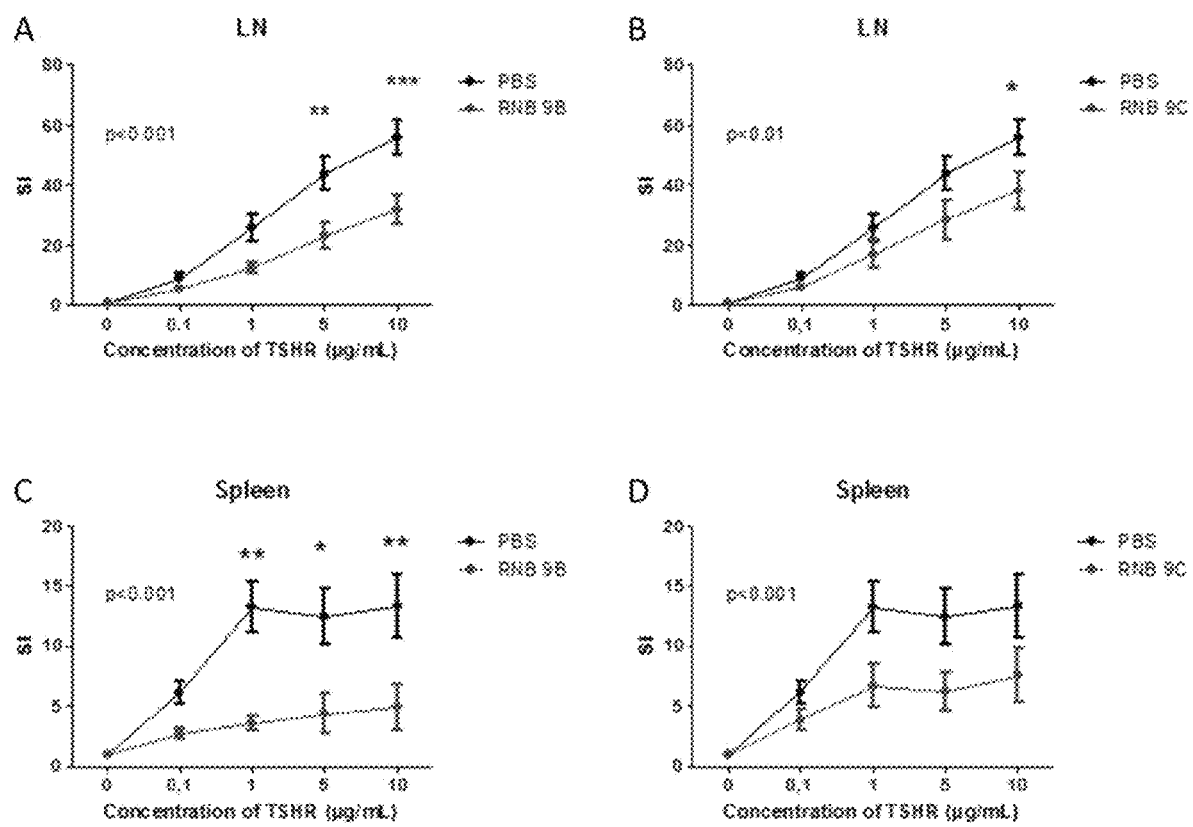
FIGS. 7A-7D: Ex vivo tolerance induction by RNB-9 peptides. DR3 mice are pretreated according the dose escalation schedule with RNB-9B (FIG. 7A, FIG. 7C) or RNB-9C (FIG. 7B, Fig. D). Data represent mean±SEM of SI values for the PBS-treated mice (black lines) and peptide-treated mice (red lines). 2-way ANOVA was used to measure overall treatment effects on T cell proliferation and p-values are written in the graphs. Bonferroni post-hoc testing was used and significant differences are indicated in the graphs (* p<0.05;  p<0.01; * p<0.001). SI, stimulation index; LN, lymph nodes.
Figure 8:
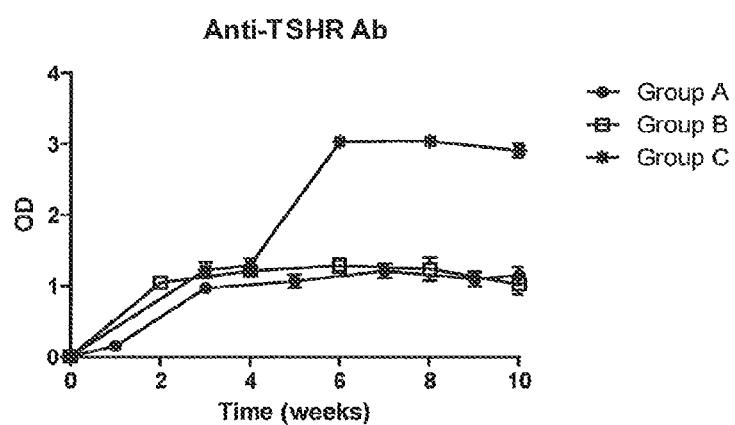
FIG. 8: TSHR antibody levels (total IgG) measured by ELISA. Mice were immunized once (group A+B) or twice (group C) with 50 µg TSHR in adjuvant. OD values are shown per group as mean±SEM.
Figure 9:
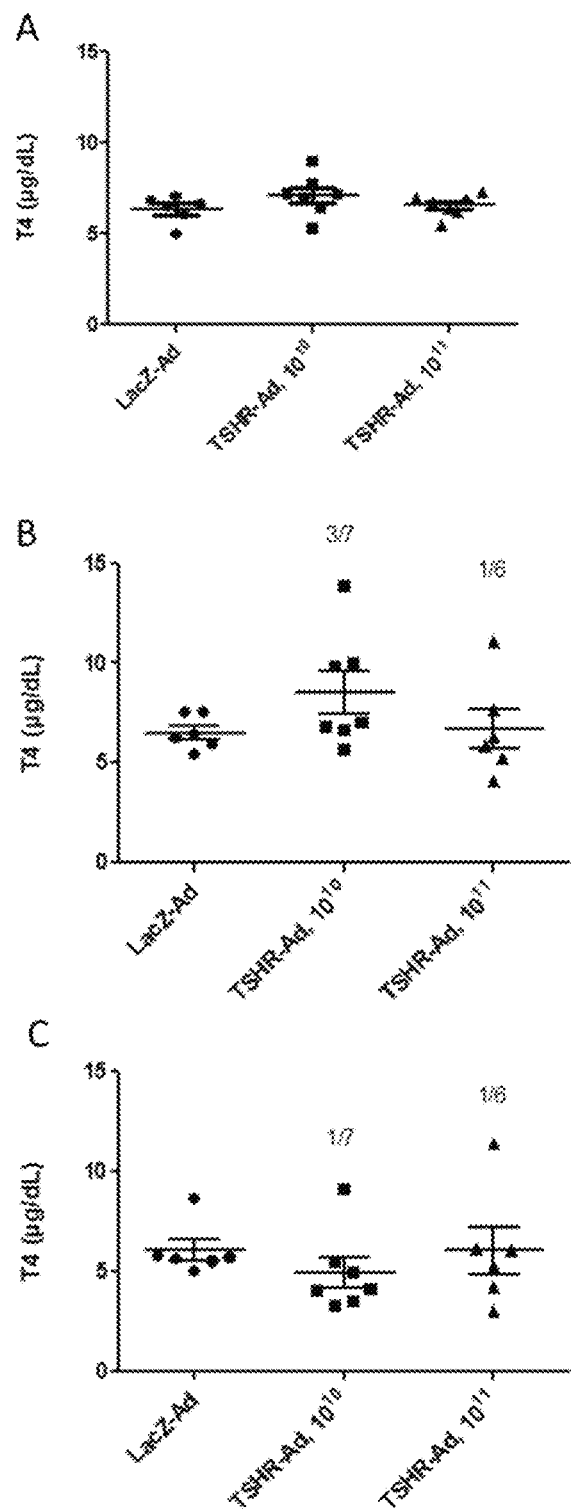
FIG. 9A-9C: Serum T4 levels in LacZ-Ad and Ad-TSHR-Ad immunized mice. Data shown are individual values for mice from different groups before (FIG. 9A), 4 weeks after (FIG. 9B) and 10 weeks after (FIG. 9C) the first immunization. The number of hyperthyroid versus total number for each group is indicated. Mice were considered hyperthyroid when their T4 levels exceeded the mean +2SD for serum T4 values in LacZ-Ad immunized mice. Mean T4 levels was not significantly different between TSHR-Ad and LacZ-Ad injected mice at 4 or 10 weeks. One-way ANOVA, Bonferroni post-hoc testing, p<0.05 was considered significantly different.
Figure 10:
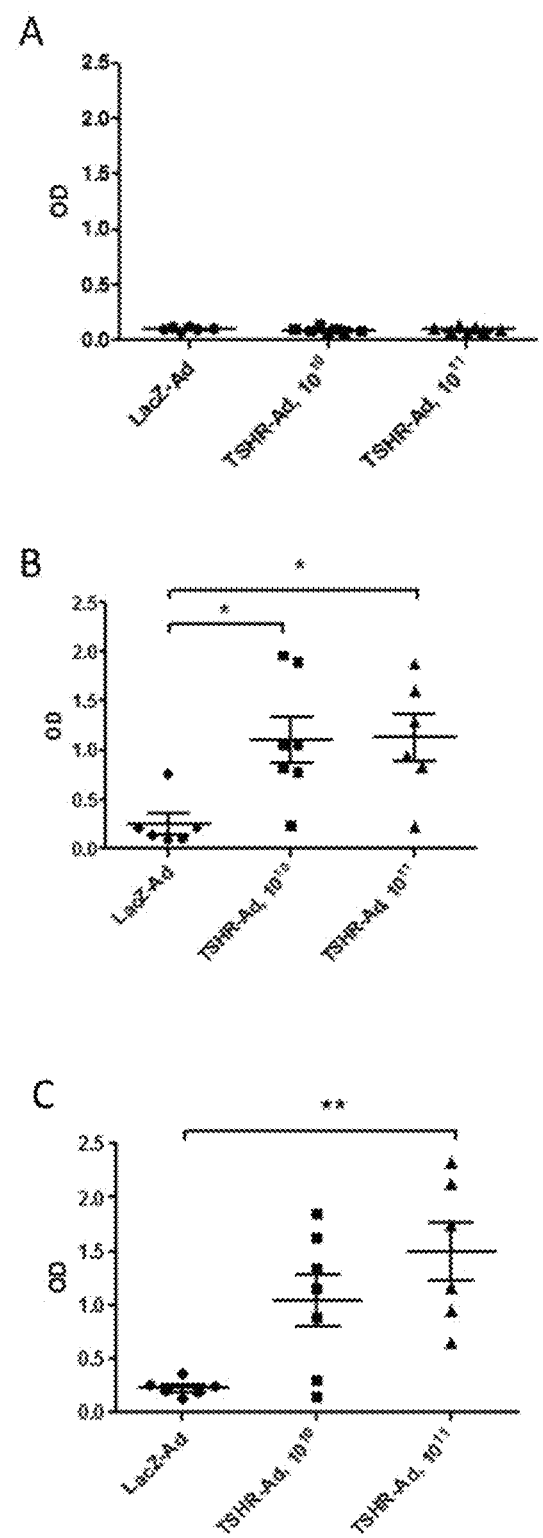
FIG. 10A-10C: Anti-TSHR antibody levels (total IgG, ELISA) in LacZ-Ad and TSHR-Ad immunized mice. Data shown are individual values for mice from different groups before (FIG. 10A), 4 weeks after (FIG. 10B) and 10 weeks after (FIG. 10C) the first immunization. Statistical analysis was performed with one-way ANOVA and Bonferroni post-hoc testing. Significant differences are indicated in the graphs (* p<0.05; ** p<0.01).
Figure 12:
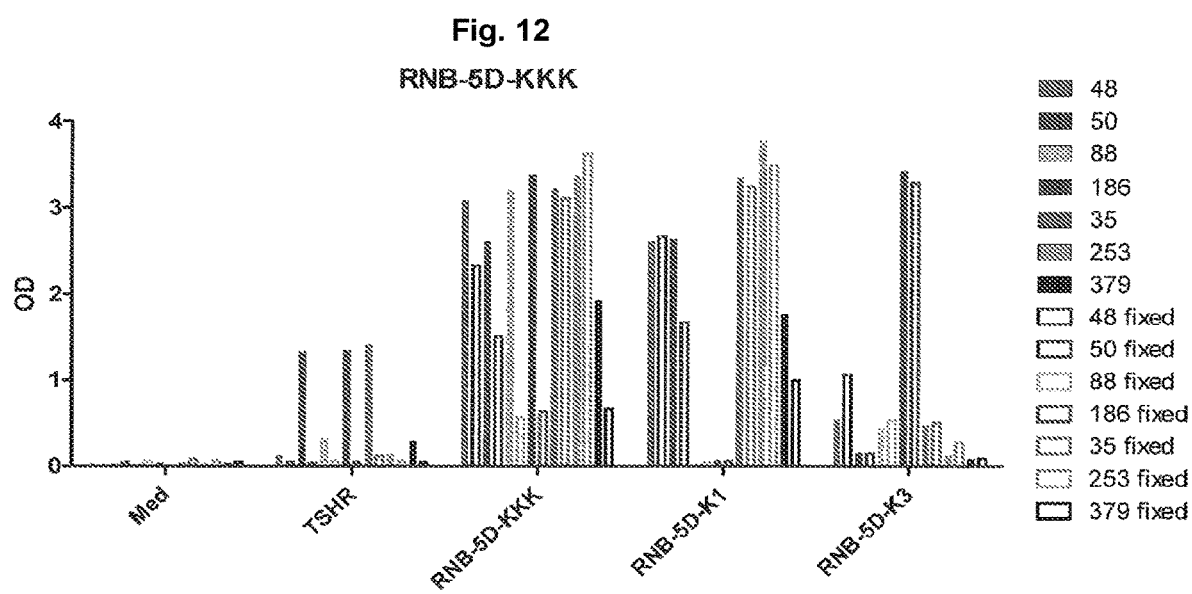
FIG. 12: Response of TSHR- and RNB-5-specific hybridoma clones, isolated from HLA-DR3 or HLA-DR4 mice immunized with TSHR/CFA, to RNB-5D modified peptides. Hybridoma clones (represented in different colours) were cultured with fresh (full bars) or fixed (empty bars) APCs and 25 µg/mL antigen for 48 hours prior to determination of IL-2 production.
Figure 13:
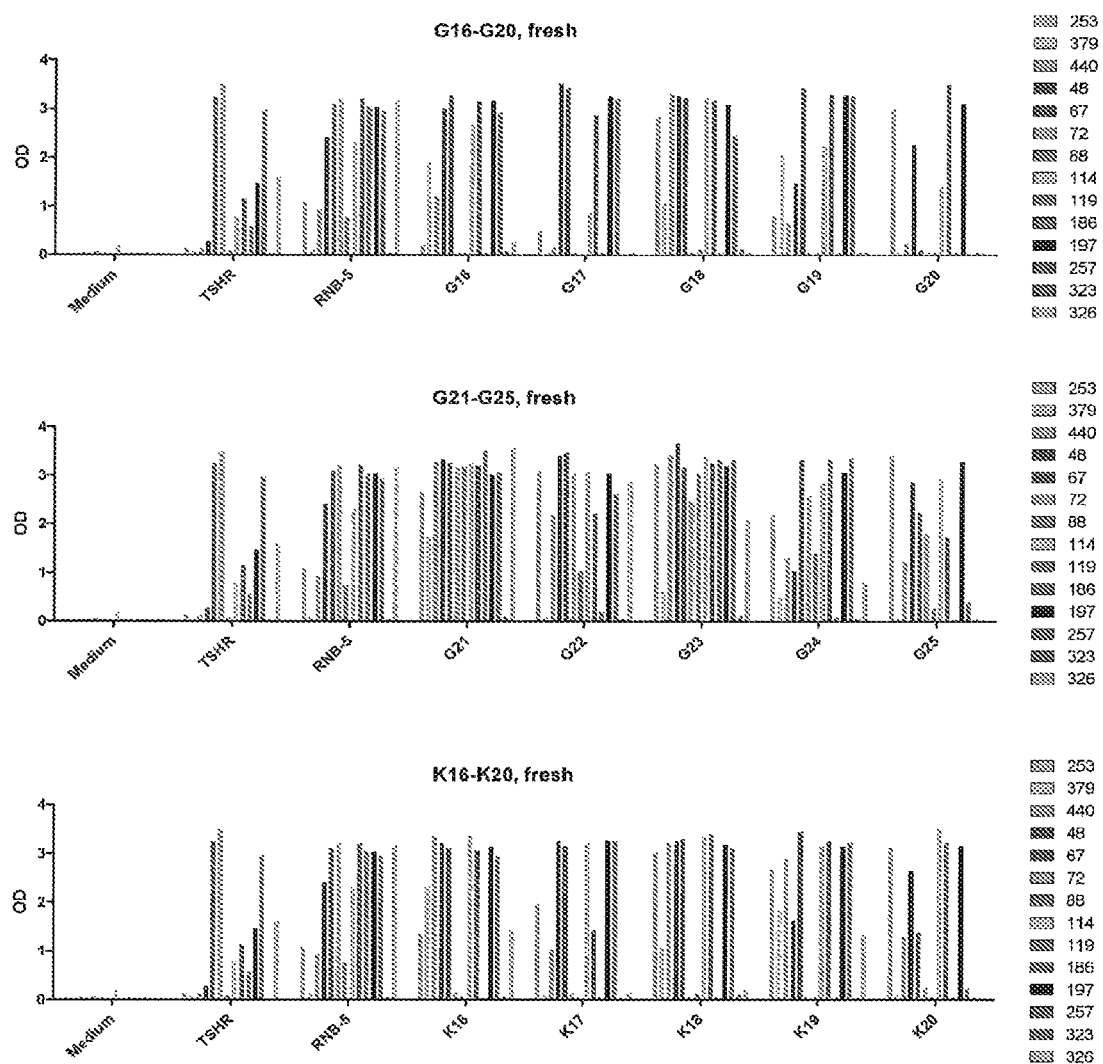
FIG. 13: Response of TSHR- and RNB-5-specific hybridoma clones, isolated from HLA-DR3 or HLA-DR4 mice immunized with TSHR/CFA, to RNB-5D modified peptides. Hybridoma clones (represented in different colours) were cultured with fresh APCs and 25 µg/mL antigen for 48 hours prior to determination of IL-2 production.
Figure 16:
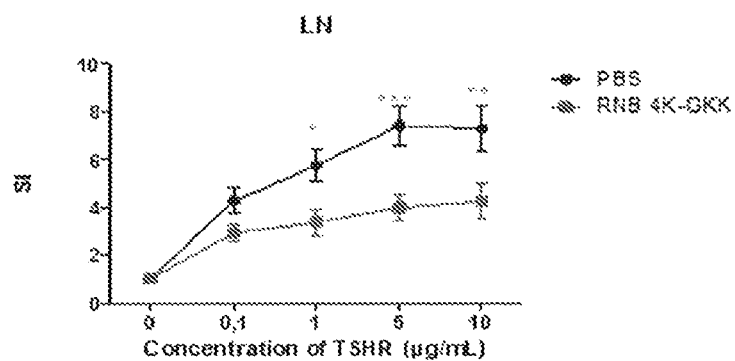
FIG. 16: Ex vivo tolerance induction by RNB 4K-GKK in DR4 mice according to the dose escalation schedule. 2-way ANOVA was used to measure overall treatment effects on T cell proliferation and p-values are written in the graphs. Bonferroni post-hoc testing was used and significant differences are indicated in the graphs (* p<0.05;  p<0.01; * p<0.001) Data represents mean±SEM for the PBS-treated (black lines) and peptide treated mice (red lines). SI stimulation index; LN lymph nodes
Figure 17:
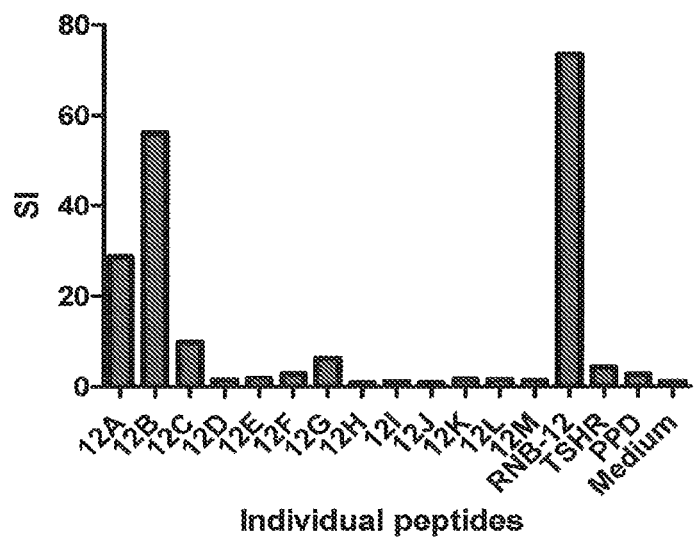
FIG. 17: Identification of the RNB12 region by reactivity of a T cell line generated from Graves' disease patients. A T cell line was generated by stimulating isolated PBMCs from a Graves' disease patient with RNB12 for 12 days. After an additional re-stimulation cycle of 12 days, the RNB12 specific T cells was tested for recognition of individual nested peptides in the RNB12 region. SI, stimulation index
Figure 18:
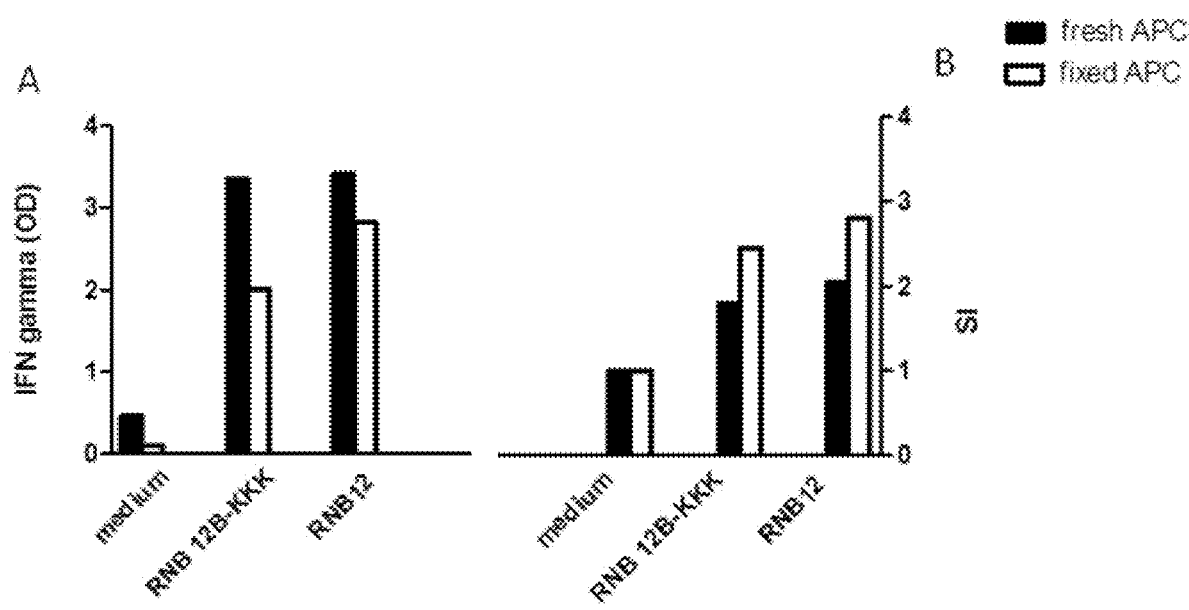
FIGS. 18A-18B: Identification of apitopes within the RNB12 region using a RNB12 specific TCL generated from a healthy donor. The RNB12 specific T cells were cultured with BM14, a human cell line expressing human MHC class II molecules in presence of peptide. Black bars represent the stimulation in presence of fresh, but irradiated BM14 cells and white bars presence of fixed APCs. (See materials and methods). Before adding 3H-thymidine to the cultures, culture supernatant was collected and frozen. The supernatant was analysed for IFN gamma (FIG. 18A) to confirm the proliferative T cell response (FIG. 18B). TCL, T cell line; APC, antigen presenting cell; MHC class II, major histocompatibility complex class II; SI, stimulation index; OD, optical density.
Figure 19:
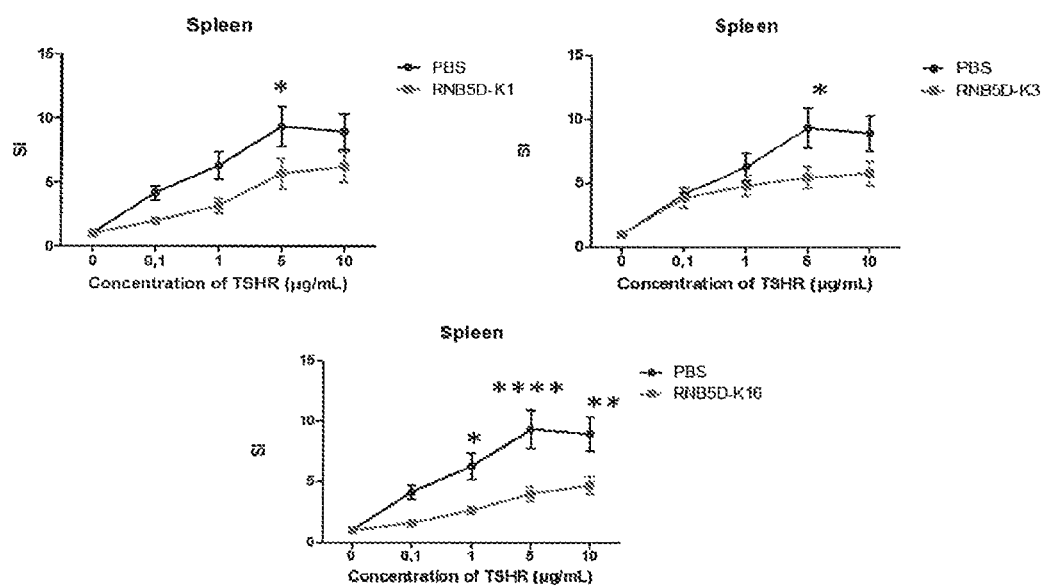
FIG. 19: Examples of Ex vivo tolerance induction by modified RNB5D modified peptides in DR3 mice according to the dose escalation schedule. 2-way ANOVA was used to measure overall treatment effects on T cell proliferation and p-values are written in the graphs. (* p<0.05;  p<0.01; * p<0.001; **** p<0.0001) Data represents mean±SEM for the PBS-treated (black lines) and peptide treated mice (red lines). SI stimulation index. A: RNB5D-K1; B: RNB5D-K3; C: RNB5D-K16

DR3 mice were injected subcutaneously in the back of the neck with RNB-5 15-mer peptides (100 µg/injection) or PBS at day −8, −6, −4 (high dose schedule) (FIG. 5). Alternatively, mice were injected with 0.1 µg, 1 µg and 10 µg peptides on days −15, −13 and −11 respectively, followed by 3 injections of 100 µg peptide on days −8, −6 and −4 (dose escalation schedule). On day 0, the mice were injected subcutaneously in the base of the tail with 100 µg antigen/CFA (RNB-5 peptide or TSHR-289 protein). Ten days after immunization, the draining LNs and spleens were harvested. Proliferation assay and cytokine measurement were performed as described above.

Animal Models for GD

Immunization of Mice with TSHR A-Subunit Adenovirus

Adenovirus expressing the human TSHR A-subunit (amino acid residues 1-289, A-subunit Ad) and control adenovirus (LacZ-Ad) expressing β-galactosidase were purchased from Viraquest (North Liberty, Iowa, USA). Six-week old female Balb/cJOlaHsd mice (Harlan Laboratories, Venray, The Netherlands) were injected intramuscularly in the thigh muscle with TSHR-Ad ($10^{10}$ or $10^{11}$ particles) or LacZ-Ad ($10^{10}$ particles). All mice were immunized simultaneously using the same batch of adenovirus. Mice were injected on three occasions at three weekly intervals (day 0, 21 and 42) and blood was drawn before the first immunization and one week after the second immunization. All mice were euthanized 4 weeks after the third injection (week 10) to obtain blood and thyroid glands.

Immunization of Mice with TSHR/CFA

Female six-week old C57/Bl6JOlaHsd mice (Harlan Laboratories) (8 mice per group) were subcutaneously challenged at the base of the tail with 50 µg TSHR-289 protein emulsified in CFA with 4 mg/ml MTb (50 µl). Mice were tail bled on days 0 (preimmune), 7, 21, 35, 49, 63 (Group A), days 0, 14, 28, 42, 56 (Group B) or days 0, 21, 28, 42, 56 (Group C). Mice of group C received a boost immunization at week 4 with 50 µg TSHR-289 protein emulsified in incomplete Freunds' adjuvant (IFA). Ten weeks after the first immunization, all mice were euthanized and blood was collected by cardiac puncture.

TSHR Antibodies

Anti-TSHR antibodies (IgG class) against purified TSHR-289 protein (Chesapeake-Perl) were measured using ELISA. 96-wells plates (half area 96-well, Fisher Scientific) were coated overnight at RT with 50 µl/well of TSHR-289 protein in PBS (0.5 µg/ml). After washing with PBS-0.05% Tween, wells were blocked with 1% BSA (w/v) in PBS for 1 h at RT and incubated with test sera (duplicate aliquots, 1:50 dilution). Mouse anti-TSHR antibody (A9, Abcam, Cambridge, UK) was used as a positive control. Antibody binding was then detected with horseradish peroxidase-conjugated goat anti-mouse IgG (Abcam) and the signal was developed with TMB. Optical density (OD) was measured in a plate reader at 450 nm (Tecan Benelux).

Serum Thyroxine and Thyroid Histology

Total thyroxine (T4) was measured in undiluted mouse serum (10 µl) using the CBI mouse/rat thyroxine ELISA kit (Calbiotech, Spring Valley, Calif., USA) according to the manufacturer's instructions. T4 values were computed from standards in the kit and expressed as µg/dl. Thyroid glands were fixed in 10% neutral buffered formalin (pH 7.5), processed to sections and stained with hematoxylin and eosin. Sections were observed for pathological changes (hypertrophy, hypercellularity of epithelial cells and infiltration of lymphocytes) and scored (KWS Biotest, Bristol, UK).

TABLE 1

| Peptide | | Sequence | Solubility | Induce response of hybridomas | Apitope |
|---|---|---|---|---|---|
| RNB-SD-GKK | G0 | KKGIYVSIDVTLQQLESHGKK | + | +++ | + |
| | G1 | KKGKYVSIDVTLQQLESHGKK | ++ | ++ | + |

TABLE 1-continued

| | Peptide | Sequence | Solubility | Induce response of hybridomas | Apitope |
|---|---|---|---|---|---|
| | G2 | KKGIKVSIDVTLQQLESHGKK | + | + | + |
| | G3 | KKGIYKSIDVTLQQLESHGKK | ++++ | + | + |
| | G4 | KKGIYVKIDVTLQQLESHGKK | + | − | − |
| | G5 | KKGIYVSKDVTLQQLESHGKK | ND | − | − |
| | G6 | KKGIYVSIKVTLQQLESHGKK | ND | − | − |
| | G7 | KKGIYVSIDKTLQQLESHGKK | ND | − | − |
| | G8 | KKGIYVSIDVKLQQLESHGKK | + | +++ | + |
| | G9 | KKGIYVSIDVTKQQLESHGKK | ND | − | − |
| | G10 | KKGIYVSIDVTLKQLESHGKK | ND | −+ | − |
| | G11 | KKGIYVSIDVTLQKLESHGKK | + | +++ | + |
| | G12 | KKGIYVSIDVTLQQKESHGKK | + | +++ | + |
| | G13 | KKGIYVSIDVTLQQLKSHGKK | + | +++ | + |
| | G14 | KKGIYVSIDVTLQQLEKHGKK | + | +++ | + |
| | G15 | KKGIYVSIDVTLQQLESKGKK | + | +++ | + |
| | G16 | KKGYVSIDVTLQOLEGKK | ++ | ++ | + |
| | G17 | KKGYVSIDVKLQQLEGKK | ++++ | ++ | + |
| | G18 | KKGYVSIDVTLQKLEGKK | ++++ | +++ | + |
| | G19 | KKGYVSIDVTLQQKEGKK | ++++ | ++ | + |
| | G20 | KKGYVSIDVKLQKKEGKK | ++++ | + | + |
| | G21 | KKGIYVSIDVTLQQLEGKK | + | +++ | + |
| | G22 | KKGIYVSIDVKLQQLEGKK | + | +++ | + |
| | G23 | KKGIYVSIDVTLQKLEGKK | + | +++ | + |
| | G24 | KKGIYVSIDVTLQQKEGKK | + | +++ | + |
| | G25 | KKGIYVSIDVKLQKKEGKK | +++ | ++ | + |
| | G26 | KKGTYVSIDVTLQQLEGKK | + | +++ | + |
| | G27 | KKGTYVSIDVKLQQLEGKK | ++++ | ++ | + |
| | G28 | KKGTYVSIDVTLQKLEGKK | + | +++ | + |
| | G29 | KKGTYVSIDVTLQQKEGKK | + | ++ | + |
| | G30 | KKGTYVSIDVKLQKKEGKK | ++++ | ++ | + |
| | M1 | KKGIYLSIDATLQRLEPHGKK | + | − | − |
| RNB-5D-KKK | K0 | KKKIYVSIDVTLQQLESHKKK | + | +++ | + |
| | K1 | KKKKYVSIDVTLQQLESHKKK | ++++ | ++ | + |
| | K2 | KKKIKVSIDVTLQQLESHKKK | + | −+ | + |
| | K3 | KKKIYKSIDVTLQQLESHKKK | ++++ | + | + |
| | K4 | KKKIYVKIDVTLQQLESHKKK | +++ | −+ | + |
| | K5 | KKKIYVSKDVTLQQLESHKKK | ND | − | − |
| | K6 | KKKIYVSIKVTLQQLESHKKK | ND | − | − |
| | K7 | KKKIYVSIDKTLQQLESHKKK | ND | − | − |

TABLE 1-continued

| Peptide | Sequence | Solubility | Induce response of hybridomas | Apitope |
|---|---|---|---|---|
| K8  | KKKIYVSIDVKLQQLESHKKK | +    | +++ | + |
| K9  | KKKIYVSIDVTKQQLESHKKK | ND   | -   | - |
| K10 | KKKIYVSIDVTLKQLESHKKK | ND   | +   | + |
| K11 | KKKIYVSIDVTLQKLESHKKK | +    | +++ | + |
| K12 | KKKIYVSIDVTLQQKESHKKK | +    | +++ | + |
| K13 | KKKIYVSIDVTLQQLKSHKKK | +    | +++ | + |
| K14 | KKKIYVSIDVTLQQLEKHKKK | +    | +++ | + |
| K15 | KKKIYVSIDVTLQQLESKKKK | +    | +++ | + |
| K16 | KKKYVSIDVTLQQLEKKK    | ++++ | ++  | + |
| K17 | KKKYVSIDVKLQQLEKKK    | ++   | ++  | + |
| K18 | KKKYVSIDVTLQKLEKKK    | +    | ++  | + |
| K19 | KKKYVSIDVTLQQKEKKK    | ++++ | ++  | + |
| K20 | KKKYVSIDVKLQKKEKKK    | +++  | +   | + |

T Cell Lines from Human PBMCs (Example 5)

Peripheral blood monocytes (PBMC) from healthy donors or Graves' disease patients were isolated (Histopaque-1077, Sigma-Aldrich), and frozen in aliquots. At day 0, cells were thawed and 106 PBMCs/ml cultured with 20 ug/ml peptide in supplemented (10 mM HEPES, 50 U/ml Penicillin/Streptomycin and 4 mM L-Glutamine (Lonza)) RPMI 1640 (Lonza) with 5% AB serum (Sigma Aldrich) added in a 6 well plate (Greiner Bio-one) and incubated in 37 C and 5% CO2. After 7 days rhIL-2 (R&D Systems) is added to a final concentration of 20 U/ml. At day 12, the cells are harvested, washed and put back into culture at a concentration of 106+2×106 newly thawed irradiated autologous PBMCs/ml in a 6 well plate stimulated with 5-10 ug/ml peptide and 20 U/ml of rhIL-2. At days 15, 18 and 21 additional rhIL-2 was added to a final concentration of 20 u/ml.

At day 24 the cells were harvested, washed and 2×104 cultured in a 96 well round-bottom plate (Cellstar, Greiner Bio One) with 105 irradiated autologous PBMCs and VAVY/BM14/MGAR human cell lines expressing human MHC cl II molecules (International Histocompatibility Working group, Seattle, US) in supplemented RPMI+5% AB serum in presence of different antigens (peptides, protein) in concentration from 5-50 ug/ml. The cultures were incubated for 48 h with 0.5 uCI/well 3H-thymidine (Perkin Elmer) added the final 18 h. After the plates been frozen the cells were harvested and read with β counter (Wallac 1450 Microbeta Trilux) to assess proliferation. Before adding 3H-thymidine, 60 ul/well cell culture supernatant was removed for cytokine analysis.

IFN Gamma ELISA

The supernatants from TCL cultures were assessed for IFN gamma content by use of the Human IFN-gamma Duoset kit, R&D Systems following the manufacturer's instruction. Optical density was measured at 450 nm (Tecan Benelux)

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, immunology or related fields are intended to be within the scope of the following claims.

The invention claimed is:

1. A method for suppressing or preventing the production of TSHR autoantibodies in a subject which comprises the step of administration to the subject of a plurality of peptides capable of binding to an MHC molecule in vitro and being presented to a T cell without antigen processing, including one or more peptide(s) selected from the following Thyroid Stimulating Hormone Receptor (TSHR) peptides:

(SEQ ID No 1)
RNB_5: ISRIYVSIDV TLQQLESHSFYNLSKVTHI (SEQ ID No 2)
RNB_4: LRTIPSHAFSNLPNISRTYVSIDVTLQQL (SEQ ID No 3)
RNB_9: TGLKMFPDLTKVYSTDIFFILEITDNPYM (SEQ ID No 64)
RNB_12: LTLKLYNNGFTSVQGYAFNGTKLDAVYL.

2. A method for suppressing or preventing the production of TSHR autoantibodies in a subject, which comprises the step of administration to the subject of a plurality of peptides, including one or more peptide(s) selected from the following:

(SEQ ID No 12)
RNB_5D-GKK: KKGIYVSIDVTLQQLESHGKK

```
                                            (SEQ ID No. 21)
RNB_5D-KKK: KKKIYVSIDVILQQLESHKKK (SEQ ID No 13)
RNB_5E-GKK: KKGYVSIDVTLQQLESHSGKK (SEQ ID No 6)
RNB_5A:     ISRIYVSIDVTLQQL (SEQ ID No 7)
RNB_5B:     SRIYVSIDVTLQQLE (SEQ ID No 8)
RNB_5C:     RIYVSIDVTLQQLES (SEQ ID No 9)
RNB_5D:     IYVSIDVTLQQLESH (SEQ ID No 10)
RNB_5E:     YVSIDVTLQQLESHS (SEQ ID No 11)
RNB_5F:     VSIDVTLQQLESHSF (SEQ ID No 14)
RNB_5F-GKK: KKGVSIDVTLQQLESHSFGKK (SEQ ID No 16)
RNB_4J-GKK: KKGSNLPNISRIYVSIDVGKK (SEQ ID No 15)
RNB_4J:     SNLPNISRIYVSIDV (SEQ ID No. 62)
RNB_4K:     NLPNISRIYVSIDVT (SEQ ID No. 63)
RNB_4K-GKK: KKGNLPNISRIYVSIDVTGKK (SEQ ID) No 18)
RNB_9B:     GLKMFPDLTKVYSTD (SEQ ID No 17)
RNB_9A:     TGLKMFPDLTKVYST (SEQ ID No 19)
RNB_9C:     LKMFPDLTKVYSTDI (SEQ ID No 20)
RNB_9D:     KNIRDLTKVY STDIF (SEQ ID No. 65)
RNB_12A:    LTLKLYNNGFTSVQG (SEQ ID No. 66)
RNB_12B:    TLKLYNNGFTSVQGY (SEQ ID No. 67)
RNB_12B-KKK: KKK TLKLYNNGFTSVQGYKKK.
```

3. A method for suppressing or preventing the production of TSHR autoantibodies in a subject, which comprises the step of administration to the subject a plurality of peptides capable of binding to an MHC molecule in vitro and being presented to a T cell without antigen processing, including one or more peptide(s) comprising a sequence:
KK-(G/K)-aa1-(RNB-5D peptide)-aa2-aa3-(G/K)-KK
wherein aa1 is no amino acid, I, K or T;
RNB-5D peptide is YVSIDVTLQQLE (SEQ ID NO: 4), or a variant thereof in which one or more amino acids has been replaced by K;
aa2 is no amino acid, S or K; and
aa3 is no amino acid, H or K.

4. A method according to claim 3, wherein the RNB-5D peptide is YVSIDVTLQQLE (SEQ ID NO: 4), or a variant thereof in which one, two or three amino acids is/are replaced by K.

5. A method according to claim 3, wherein the one or more peptide(s) are selected from the following group: KKGIYVSIDVTLQQLESHGKK (SEQ ID No 12), KKGKYVSIDVTLQQLESHGKK (SEQ ID No 22), KKGIKVSIDVTLQQLESHGKK (SEQ ID No 23), KKGIYKSIDVTLQQLESHGKK (SEQ ID No 24), KKGIYVSIDVKLQQLESHGKK (SEQ ID No 25), KKGIYVSIDVTLQKLESHGKK (SEQ ID No 26), KKGIYVSIDVTLQQKESHGKK (SEQ ID No 27), KKGIYVSIDVTLQQLKSHGKK (SEQ ID No 28), KKGIYVSIDVTLQQLEKHGKK (SEQ ID No 29), KKGIYVSIDVTLQQLESKGKK (SEQ ID No 30), KKGYVSIDVTLQQLEGKK (SEQ ID No 31), KKGYVSIDVKLQQLEGKK (SEQ ID No 32), KKGYVSIDVTLQQLEGKK (SEQ ID No 33), KKGYVSIDVTLQQKEGKK (SEQ ID No 34), KKGYVSIDVKLQKKEGKK (SEQ ID No 35), KKGIYVSIDVTLQQLEGKK (SEQ ID No 36), KKGIYVSIDVKLQQLEGKK (SEQ ID No 37), KKGIYVSIDVTLQKLEGKK (SEQ ID No 38), KKGIYVSIDVTLQQKEGKK (SEQ ID No 39), KKGIYVSIDVKLQKKEGKK (SEQ ID No 40), KKGTYVSIDVTLQQLEGKK (SEQ ID No 41), KKGTYVSIDVKLQQLEGKK (SEQ ID No 42), KKGTYVSIDVTLQKLEGKK (SEQ ID No 43), KKGTYVSIDVTLQQKEGKK (SEQ ID No 44), KKGTYVSIDVKLQKKEGKK (SEQ ID No 45), KKKIYVSIDVTLQQLESHKKK (SEQ ID No 21), KKKKYVSIDVTLQQLESHKKK (SEQ ID No 46), KKKIKVSIDVTLQQLESHKKK (SEQ ID No 47), KKKIYVKSIDVTLQQLESJIKKK (SEQ ID No 48), KKKIYVKIDVTLQQLESHKKK (SEQ ID No 49), KKKIYVSIDVKLQQLESHKKK (SEQ ID No 50), KKKIYVSIDVTLKQLESHKKK (SEQ ID No 51), KKKIYVSIDVTLQKLESHKKK (SEQ ID No 52), KKKIYVSIDVTLQQKESHKKK (SEQ ID No 53), KKKIYVSIDVTLQQLKSHKKK (SEQ ID No 54), KKKIYVSIDVTLQQLEKHKKK (SEQ ID No 55), KKKIYVSIDVTLQQLESKKKK (SEQ ID No 56), KKKYVSIDVTLQQLEKKK (SEQ ID No 57), KKKYVSIDVKLQQLEKKK (SEQ ID No 58), KKKYVSIDVTLQKLEKKK (SEQ ID No 59), KKKYVSIDVTLQQKEKKK (SEQ ID No 60), KKKYVSIDVKLQKKEKKK (SEQ ID No. 61).

6. A method according to claim 5, wherein the one or more peptide(s) are selected from the group consisting of: KKGKYVSIDVTLQQLESHGKK (SEQ ID No. 22), KKGIYKSIDVTLQQLESHGKK (SEQ ID No. 24), KKGYVSIDVTLQQLEGKK (SEQ ID No. 31), KKGYVSIDVKLQQLEGKK (SEQ ID 32), KKGYVSIDVTQKLEGKK (SEQ ID No. 33), KKGYVSIDVTLQQKEGKK (SEQ ID No. 34), KKGYVSIDVKLQKKEGKK (SEQ ID No. 35), KKGIYVSIDVKLQKKEGKK (SEQ ID No. 40), KKGTYSIDVKLQQLEGKK (SEQ ID No. 42), KKGTYVSIDVKLQKKEGKK (SEQ ID No. 45), KKKKYVSIDVTLQQLESHKKK (SEQ ID No. 46), KKKIYKSIDVTLQQLESHKKK (SEQ ID No. 48), KKKIYVKIDVTLQQLESHKKK (SEQ ID No. 49), KKKYVSIDVTLQQLEKKK (SEQ ID No. 57), KKKYVSIDVKLQQLEKKK (SEQ ID No. 58), KKKYVSIDVTLQQKEKKK (SEQ ID No. 60), KKKYVSIDVKLQKKEKKK (SEQ ID No. 61).

7. A method according to claim 6, wherein the one or more peptide(s) are selected from the group consisting of: KKGIYKSIDVTLQQLESHGKK (SEQ ID No. 24), KKGYVSIDVKLQQLEGKK (SEQ ID No. 32), KKGYVSIDVTLQKLEGKK (SEQ ID No. 33), KKGYVSIDVTLQQKEGKK (SEQ ID No. 34), KKGYVSIDVKLQKKEGKK (SEQ ID No. 35), KKG- TYVSIDVKLQQLEGKK (SEQ Id No. 42), KKGTYVSID-VKLQKKEGKK (SEQ ID No. 45), KKKKYVSID-VTLQQLESHKKK (SEQ ID No. 46), KKKIYKSIDVTLQQLESHKKK (SEQ ID No. 48), KKKYVSIDVTLQQLEKKK (SEQ ID No. 57), KKKYVSIDVTLQQKEKK (SEQ ID No. 60).

8. A method according to claim 6, wherein the one or more peptide(s) are selected from the group consisting of: KKGYVSIDVTLQKLEGKK (SEQ ID No. 32), KKGYVSIDVKLQKKEGKK (SEQ ID No. 34), KKK-KYVSIDVTLQQLESHKKK (SEQ ID No. 46), KKKIYK-SIDVTLQQLESHKKK (SEQ ID No. 48), KKKYVSID-VTLQQLEKKK (SEQ ID No. 57), KKKYVSIDVTLQQKEKKK (SEQ ID No. 60).

9. The method of claim 1 wherein the subject has Graves' Disease.

10. The method of claim 2 wherein the subject has Graves' Disease.

11. The method of claim 3 wherein the subject has Graves' Disease.

12. The method of claim 4 wherein the subject has Graves' Disease.

13. The method of claim 5 wherein the subject has Graves' Disease.

14. The method of claim 6 wherein the subject has Graves' Disease.

15. The method of claim 7 wherein the subject has Graves' Disease.

16. The method of claim 8 wherein the subject has Graves' Disease.

17. The method according to claim 1, wherein the subject is HLA-DR3.

18. The method according to claim 9, wherein the subject is HLA-DR3.

19. The method according to claim 1, wherein the one or more peptide(s) is one peptide selected from the following Thyroid Stimulating Hormone Receptor (TSHR) peptides:

```
                                         (SEQ ID No 1)
RNB_5: ISRIYVSIDV TLQQLESHSFYNLSKVTHI (SEQ ID No 2)
RNB_4: LRTIPSHAFSNLPNISRTYVSIDVTLQQL (SEQ ID No 3)
RNB_9: TGLKMFPDLTKVYSTDIFFILEITDNPYM (SEQ ID No 64)
RNB_12: LTLKLYNNGFTSVQGYAFNGTKLDAVYL.
```

20. The method according to claim 2, wherein the one or more peptide(s) is one peptide selected from the following:

```
                                         (SEQ ID No 12)
RNB_5D-GKK: KKGIYVSIDVTLQQLESHGKK (SEQ ID No. 21)
RNB_5D-KKK: KKKIYVSIDVILQQLESHKKK
```

```
                                         (SEQ ID No 13)
RNB_5E-GKK: KKGYVSIDVTLQQLESHSGKK (SEQ ID No 6)
RNB_5A: ISRIYVSIDVTLQQL (SEQ ID No 7)
RNB_5B: SRIYVSIDVTLQQLE (SEQ ID No 8)
RNB_5C: RIYVSIDVTLQQLES (SEQ ID No 9)
RNB_5D: IYVSIDVTLQQLESH (SEQ ID No 10)
RNB_5E: YVSIDVTLQQLESHS (SEQ ID No 11)
RNB_5F: VSIDVTLQQLESHSF (SEQ ID No 14)
RNB_5F-GKK: KKGVSIDVTLQQLESHSFGKK (SEQ ID No 16)
RNB_4J-GKK: KKGSNLPNISRIYVSIDVGKK (SEQ ID No 15)
RNB_4J: SNLPNISRIYVSIDV (SEQ ID No. 62)
RNB_4K: NLPNISRIYVSIDVT (SEQ ID No. 63)
RNB_4K-GKK: KKGNLPNISRIYVSIDVTGKK (SEQ ID) No 18)
RNB_9B: GLKMFPDLTKVYSTD (SEQ ID No 17)
RNB_9A: TGLKMFPDLTKVYST (SEQ ID No 19)
RNB_9C: LKMFPDLTKVYSTDI (SEQ ID No 20)
RNB_9D: KNIRDLTKVY STDIF (SEQ ID No. 65)
RNB_12A: LTLKLYNNGFTSVQG (SEQ ID No. 66)
RNB_12B: TLKLYNNGFTSVQGY (SEQ ID No. 67)
RNB_12B-KKK: KKK TLKLYNNGFTSVQGYKKK.
```

21. The method according to claim 3, wherein the one or more peptide(s) is one peptide comprising a sequence:
KK-(G/K)-aa1-(RNB-5D peptide)-aa2-aa3-(G/K)-KK, wherein
aa1 is no amino acid, I, K or T;
RNB-5D peptide is YVSIDVTLQQLE (SEQ ID NO: 4), or a variant thereof in which one or more amino acids has been replaced by K;
aa2 is no amino acid, S or K; and
aa3 is no amino acid, H or K.

* * * * *

SEQUENCE LISTING

```
<160> NUMBER OF SEQ ID NOS: 134

<210> SEQ ID NO 1
<211> LENGTH: 29
<212> TYPE: PRT
<213> ORGANISM: Homo sapiens

<400> SEQUENCE: 1

Ile Ser Arg Ile Tyr Val Ser Ile Asp Val Thr Leu Gln Gln Leu Glu
1               5                   10                  15

Ser His Ser Phe Tyr Asn Leu Ser Lys Val Thr His Ile
```

```
                20                  25

<210> SEQ ID NO 2
<211> LENGTH: 29
<212> TYPE: PRT
<213> ORGANISM: Homo sapiens

<400> SEQUENCE: 2

Leu Arg Thr Ile Pro Ser His Ala Phe Ser Asn Leu Pro Asn Ile Ser
1               5                   10                  15

Arg Ile Tyr Val Ser Ile Asp Val Thr Leu Gln Gln Leu
            20                  25

<210> SEQ ID NO 3
<211> LENGTH: 29
<212> TYPE: PRT
<213> ORGANISM: Homo sapiens

<400> SEQUENCE: 3

Thr Gly Leu Lys Met Phe Pro Asp Leu Thr Lys Val Tyr Ser Thr Asp
1               5                   10                  15

Ile Phe Phe Ile Leu Glu Ile Thr Asp Asn Pro Tyr Met
            20                  25

<210> SEQ ID NO 4
<211> LENGTH: 12
<212> TYPE: PRT
<213> ORGANISM: Homo sapiens

<400> SEQUENCE: 4

Tyr Val Ser Ile Asp Val Thr Leu Gln Gln Leu Glu
1               5                   10

<210> SEQ ID NO 5
<211> LENGTH: 764
<212> TYPE: PRT
<213> ORGANISM: Homo sapiens

<400> SEQUENCE: 5

Met Arg Pro Ala Asp Leu Leu Gln Leu Val Leu Leu Leu Asp Leu Pro
1               5                   10                  15

Arg Asp Leu Gly Gly Met Gly Cys Ser Ser Pro Pro Cys Glu Cys His
            20                  25                  30

Gln Glu Glu Asp Phe Arg Val Thr Cys Lys Asp Ile Gln Arg Ile Pro
        35                  40                  45

Ser Leu Pro Pro Ser Thr Gln Thr Leu Lys Leu Ile Glu Thr His Leu
    50                  55                  60

Arg Thr Ile Pro Ser His Ala Phe Ser Asn Leu Pro Asn Ile Ser Arg
65                  70                  75                  80

Ile Tyr Val Ser Ile Asp Val Thr Leu Gln Gln Leu Glu Ser His Ser
                85                  90                  95

Phe Tyr Asn Leu Ser Lys Val Thr His Ile Glu Ile Arg Asn Thr Arg
            100                 105                 110

Asn Leu Thr Tyr Ile Asp Pro Asp Ala Leu Lys Glu Leu Pro Leu Leu
        115                 120                 125

Lys Phe Leu Gly Ile Phe Asn Thr Gly Leu Lys Met Phe Pro Asp Leu
    130                 135                 140

Thr Lys Val Tyr Ser Thr Asp Ile Phe Phe Ile Leu Glu Ile Thr Asp
145                 150                 155                 160
```

```
Asn Pro Tyr Met Thr Ser Ile Pro Val Asn Ala Phe Gln Gly Leu Cys
                165                 170                 175
Asn Glu Thr Leu Thr Leu Lys Leu Tyr Asn Asn Gly Phe Thr Ser Val
            180                 185                 190
Gln Gly Tyr Ala Phe Asn Gly Thr Lys Leu Asp Ala Val Tyr Leu Asn
        195                 200                 205
Lys Asn Lys Tyr Leu Thr Val Ile Asp Lys Asp Ala Phe Gly Gly Val
    210                 215                 220
Tyr Ser Gly Pro Ser Leu Leu Asp Val Ser Gln Thr Ser Val Thr Ala
225                 230                 235                 240
Leu Pro Ser Lys Gly Leu Glu His Leu Lys Glu Leu Ile Ala Arg Asn
                245                 250                 255
Thr Trp Thr Leu Lys Lys Leu Pro Leu Ser Leu Ser Phe Leu His Leu
            260                 265                 270
Thr Arg Ala Asp Leu Ser Tyr Pro Ser His Cys Cys Ala Phe Lys Asn
        275                 280                 285
Gln Lys Lys Ile Arg Gly Ile Leu Glu Ser Leu Met Cys Asn Glu Ser
    290                 295                 300
Ser Met Gln Ser Leu Arg Gln Arg Lys Ser Val Asn Ala Leu Asn Ser
305                 310                 315                 320
Pro Leu His Gln Glu Tyr Glu Glu Asn Leu Gly Asp Ser Ile Val Gly
                325                 330                 335
Tyr Lys Glu Lys Ser Lys Phe Gln Asp Thr His Asn Asn Ala His Tyr
            340                 345                 350
Tyr Val Phe Phe Glu Glu Gln Glu Asp Glu Ile Ile Gly Phe Gly Gln
        355                 360                 365
Glu Leu Lys Asn Pro Gln Glu Glu Thr Leu Gln Ala Phe Asp Ser His
    370                 375                 380
Tyr Asp Tyr Thr Ile Cys Gly Asp Ser Glu Asp Met Val Cys Thr Pro
385                 390                 395                 400
Lys Ser Asp Glu Phe Asn Pro Cys Glu Asp Ile Met Gly Tyr Lys Phe
                405                 410                 415
Leu Arg Ile Val Val Trp Phe Val Ser Leu Leu Ala Leu Leu Gly Asn
            420                 425                 430
Val Phe Val Leu Leu Ile Leu Leu Thr Ser His Tyr Lys Leu Asn Val
        435                 440                 445
Pro Arg Phe Leu Met Cys Asn Leu Ala Phe Ala Asp Phe Cys Met Gly
    450                 455                 460
Met Tyr Leu Leu Leu Ile Ala Ser Val Asp Leu Tyr Thr His Ser Glu
465                 470                 475                 480
Tyr Tyr Asn His Ala Ile Asp Trp Gln Thr Gly Pro Gly Cys Asn Thr
                485                 490                 495
Ala Gly Phe Phe Thr Val Phe Ala Ser Glu Leu Ser Val Tyr Thr Leu
            500                 505                 510
Thr Val Ile Thr Leu Glu Arg Trp Tyr Ala Ile Thr Phe Ala Met Arg
        515                 520                 525
Leu Asp Arg Lys Ile Arg Leu Arg His Ala Cys Ala Ile Met Val Gly
    530                 535                 540
Gly Trp Val Cys Cys Phe Leu Leu Ala Leu Leu Pro Leu Val Gly Ile
545                 550                 555                 560
Ser Ser Tyr Ala Lys Val Ser Ile Cys Leu Pro Met Asp Thr Glu Thr
                565                 570                 575
Pro Leu Ala Leu Ala Tyr Ile Val Phe Val Leu Thr Leu Asn Ile Val
```

```
                580                 585                 590
Ala Phe Val Ile Val Cys Cys Cys Tyr Val Lys Ile Tyr Ile Thr Val
            595                 600                 605

Arg Asn Pro Gln Tyr Asn Pro Gly Asp Lys Asp Thr Lys Ile Ala Lys
        610                 615                 620

Arg Met Ala Val Leu Ile Phe Thr Asp Phe Ile Cys Met Ala Pro Ile
625                 630                 635                 640

Ser Phe Tyr Ala Leu Ser Ala Ile Leu Asn Lys Pro Leu Ile Thr Val
                645                 650                 655

Ser Asn Ser Lys Ile Leu Leu Val Leu Phe Tyr Pro Leu Asn Ser Cys
            660                 665                 670

Ala Asn Pro Phe Leu Tyr Ala Ile Phe Thr Lys Ala Phe Gln Arg Asp
        675                 680                 685

Val Phe Ile Leu Leu Ser Lys Phe Gly Ile Cys Lys Arg Gln Ala Gln
    690                 695                 700

Ala Tyr Arg Gly Gln Arg Val Pro Pro Lys Asn Ser Thr Asp Ile Gln
705                 710                 715                 720

Val Gln Lys Val Thr His Asp Met Arg Gln Gly Leu His Asn Met Glu
                725                 730                 735

Asp Val Tyr Glu Leu Ile Glu Asn Ser His Leu Thr Pro Lys Lys Gln
            740                 745                 750

Gly Gln Ile Ser Glu Glu Tyr Met Gln Thr Val Leu
        755                 760

<210> SEQ ID NO 6
<211> LENGTH: 15
<212> TYPE: PRT
<213> ORGANISM: Homo sapiens

<400> SEQUENCE: 6

Ile Ser Arg Ile Tyr Val Ser Ile Asp Val Thr Leu Gln Gln Leu
1               5                   10                  15

<210> SEQ ID NO 7
<211> LENGTH: 15
<212> TYPE: PRT
<213> ORGANISM: Homo sapiens

<400> SEQUENCE: 7

Ser Arg Ile Tyr Val Ser Ile Asp Val Thr Leu Gln Gln Leu Glu
1               5                   10                  15

<210> SEQ ID NO 8
<211> LENGTH: 15
<212> TYPE: PRT
<213> ORGANISM: Homo sapiens

<400> SEQUENCE: 8

Arg Ile Tyr Val Ser Ile Asp Val Thr Leu Gln Gln Leu Glu Ser
1               5                   10                  15

<210> SEQ ID NO 9
<211> LENGTH: 15
<212> TYPE: PRT
<213> ORGANISM: Homo sapiens

<400> SEQUENCE: 9

Ile Tyr Val Ser Ile Asp Val Thr Leu Gln Gln Leu Glu Ser His
1               5                   10                  15
```

```
<210> SEQ ID NO 10
<211> LENGTH: 15
<212> TYPE: PRT
<213> ORGANISM: Homo sapiens

<400> SEQUENCE: 10

Tyr Val Ser Ile Asp Val Thr Leu Gln Gln Leu Glu Ser His Ser
1               5                   10                  15

<210> SEQ ID NO 11
<211> LENGTH: 15
<212> TYPE: PRT
<213> ORGANISM: Homo sapiens

<400> SEQUENCE: 11

Val Ser Ile Asp Val Thr Leu Gln Gln Leu Glu Ser His Ser Phe
1               5                   10                  15

<210> SEQ ID NO 12
<211> LENGTH: 21
<212> TYPE: PRT
<213> ORGANISM: Artificial Sequence
<220> FEATURE:
<223> OTHER INFORMATION: TSHR peptide variant

<400> SEQUENCE: 12

Lys Lys Gly Ile Tyr Val Ser Ile Asp Val Thr Leu Gln Gln Leu Glu
1               5                   10                  15

Ser His Gly Lys Lys
            20

<210> SEQ ID NO 13
<211> LENGTH: 21
<212> TYPE: PRT
<213> ORGANISM: Artificial Sequence
<220> FEATURE:
<223> OTHER INFORMATION: TSHR peptide variant

<400> SEQUENCE: 13

Lys Lys Gly Tyr Val Ser Ile Asp Val Thr Leu Gln Gln Leu Glu Ser
1               5                   10                  15

His Ser Gly Lys Lys
            20

<210> SEQ ID NO 14
<211> LENGTH: 21
<212> TYPE: PRT
<213> ORGANISM: Artificial Sequence
<220> FEATURE:
<223> OTHER INFORMATION: TSHR peptide variant

<400> SEQUENCE: 14

Lys Lys Gly Val Ser Ile Asp Val Thr Leu Gln Gln Leu Glu Ser His
1               5                   10                  15

Ser Phe Gly Lys Lys
            20

<210> SEQ ID NO 15
<211> LENGTH: 15
<212> TYPE: PRT
<213> ORGANISM: Homo sapiens

<400> SEQUENCE: 15

Ser Asn Leu Pro Asn Ile Ser Arg Ile Tyr Val Ser Ile Asp Val
```

<210> SEQ ID NO 16
<211> LENGTH: 21
<212> TYPE: PRT
<213> ORGANISM: Artificial Sequence
<220> FEATURE:
<223> OTHER INFORMATION: TSHR peptide variant

<400> SEQUENCE: 16

Lys Lys Gly Ser Asn Leu Pro Asn Ile Ser Arg Ile Tyr Val Ser Ile
1               5                   10                  15

Asp Val Gly Lys Lys
            20

<210> SEQ ID NO 17
<211> LENGTH: 15
<212> TYPE: PRT
<213> ORGANISM: Homo sapiens

<400> SEQUENCE: 17

Thr Gly Leu Lys Met Phe Pro Asp Leu Thr Lys Val Tyr Ser Thr
1               5                   10                  15

<210> SEQ ID NO 18
<211> LENGTH: 15
<212> TYPE: PRT
<213> ORGANISM: Homo sapiens

<400> SEQUENCE: 18

Gly Leu Lys Met Phe Pro Asp Leu Thr Lys Val Tyr Ser Thr Asp
1               5                   10                  15

<210> SEQ ID NO 19
<211> LENGTH: 15
<212> TYPE: PRT
<213> ORGANISM: Homo sapiens

<400> SEQUENCE: 19

Leu Lys Met Phe Pro Asp Leu Thr Lys Val Tyr Ser Thr Asp Ile
1               5                   10                  15

<210> SEQ ID NO 20
<211> LENGTH: 15
<212> TYPE: PRT
<213> ORGANISM: Homo sapiens

<400> SEQUENCE: 20

Lys Met Phe Pro Asp Leu Thr Lys Val Tyr Ser Thr Asp Ile Phe
1               5                   10                  15

<210> SEQ ID NO 21
<211> LENGTH: 21
<212> TYPE: PRT
<213> ORGANISM: Artificial Sequence
<220> FEATURE:
<223> OTHER INFORMATION: TSHR peptide variant

<400> SEQUENCE: 21

Lys Lys Lys Ile Tyr Val Ser Ile Asp Val Thr Leu Gln Gln Leu Glu
1               5                   10                  15

Ser His Lys Lys Lys
            20

```
<210> SEQ ID NO 22
<211> LENGTH: 21
<212> TYPE: PRT
<213> ORGANISM: Artificial Sequence
<220> FEATURE:
<223> OTHER INFORMATION: TSHR peptide variant

<400> SEQUENCE: 22

Lys Lys Gly Lys Tyr Val Ser Ile Asp Val Thr Leu Gln Gln Leu Glu
1               5                   10                  15

Ser His Gly Lys Lys
            20

<210> SEQ ID NO 23
<211> LENGTH: 21
<212> TYPE: PRT
<213> ORGANISM: Artificial Sequence
<220> FEATURE:
<223> OTHER INFORMATION: TSHR peptide variant

<400> SEQUENCE: 23

Lys Lys Gly Ile Lys Val Ser Ile Asp Val Thr Leu Gln Gln Leu Glu
1               5                   10                  15

Ser His Gly Lys Lys
            20

<210> SEQ ID NO 24
<211> LENGTH: 21
<212> TYPE: PRT
<213> ORGANISM: Artificial Sequence
<220> FEATURE:
<223> OTHER INFORMATION: TSHR peptide variant

<400> SEQUENCE: 24

Lys Lys Gly Ile Tyr Lys Ser Ile Asp Val Thr Leu Gln Gln Leu Glu
1               5                   10                  15

Ser His Gly Lys Lys
            20

<210> SEQ ID NO 25
<211> LENGTH: 21
<212> TYPE: PRT
<213> ORGANISM: Artificial Sequence
<220> FEATURE:
<223> OTHER INFORMATION: TSHR peptide variant

<400> SEQUENCE: 25

Lys Lys Gly Ile Tyr Val Ser Ile Asp Val Lys Leu Gln Gln Leu Glu
1               5                   10                  15

Ser His Gly Lys Lys
            20

<210> SEQ ID NO 26
<211> LENGTH: 21
<212> TYPE: PRT
<213> ORGANISM: Artificial Sequence
<220> FEATURE:
<223> OTHER INFORMATION: TSHR peptide variant

<400> SEQUENCE: 26

Lys Lys Gly Ile Tyr Val Ser Ile Asp Val Thr Leu Gln Lys Leu Glu
1               5                   10                  15

Ser His Gly Lys Lys
            20
```

<210> SEQ ID NO 27
<211> LENGTH: 21
<212> TYPE: PRT
<213> ORGANISM: Artificial Sequence
<220> FEATURE:
<223> OTHER INFORMATION: TSHR peptide variant

<400> SEQUENCE: 27

Lys Lys Gly Ile Tyr Val Ser Ile Asp Val Thr Leu Gln Gln Lys Glu
1               5                   10                  15

Ser His Gly Lys Lys
            20

<210> SEQ ID NO 28
<211> LENGTH: 21
<212> TYPE: PRT
<213> ORGANISM: Artificial Sequence
<220> FEATURE:
<223> OTHER INFORMATION: TSHR peptide variant

<400> SEQUENCE: 28

Lys Lys Gly Ile Tyr Val Ser Ile Asp Val Thr Leu Gln Gln Leu Lys
1               5                   10                  15

Ser His Gly Lys Lys
            20

<210> SEQ ID NO 29
<211> LENGTH: 21
<212> TYPE: PRT
<213> ORGANISM: Artificial Sequence
<220> FEATURE:
<223> OTHER INFORMATION: TSHR peptide variant

<400> SEQUENCE: 29

Lys Lys Gly Ile Tyr Val Ser Ile Asp Val Thr Leu Gln Gln Leu Glu
1               5                   10                  15

Lys His Gly Lys Lys
            20

<210> SEQ ID NO 30
<211> LENGTH: 21
<212> TYPE: PRT
<213> ORGANISM: Artificial Sequence
<220> FEATURE:
<223> OTHER INFORMATION: TSHR peptide variant

<400> SEQUENCE: 30

Lys Lys Gly Ile Tyr Val Ser Ile Asp Val Thr Leu Gln Gln Leu Glu
1               5                   10                  15

Ser Lys Gly Lys Lys
            20

<210> SEQ ID NO 31
<211> LENGTH: 18
<212> TYPE: PRT
<213> ORGANISM: Artificial Sequence
<220> FEATURE:
<223> OTHER INFORMATION: TSHR peptide variant

<400> SEQUENCE: 31

Lys Lys Gly Tyr Val Ser Ile Asp Val Thr Leu Gln Gln Leu Glu Gly
1               5                   10                  15

Lys Lys

```
<210> SEQ ID NO 32
<211> LENGTH: 18
<212> TYPE: PRT
<213> ORGANISM: Artificial Sequence
<220> FEATURE:
<223> OTHER INFORMATION: TSHR peptide variant

<400> SEQUENCE: 32

Lys Lys Gly Tyr Val Ser Ile Asp Val Lys Leu Gln Gln Leu Glu Gly
1               5                   10                  15

Lys Lys

<210> SEQ ID NO 33
<211> LENGTH: 18
<212> TYPE: PRT
<213> ORGANISM: Artificial Sequence
<220> FEATURE:
<223> OTHER INFORMATION: TSHR peptide variant

<400> SEQUENCE: 33

Lys Lys Gly Tyr Val Ser Ile Asp Val Thr Leu Gln Lys Leu Glu Gly
1               5                   10                  15

Lys Lys

<210> SEQ ID NO 34
<211> LENGTH: 18
<212> TYPE: PRT
<213> ORGANISM: Artificial Sequence
<220> FEATURE:
<223> OTHER INFORMATION: TSHR peptide variant

<400> SEQUENCE: 34

Lys Lys Gly Tyr Val Ser Ile Asp Val Thr Leu Gln Gln Lys Glu Gly
1               5                   10                  15

Lys Lys

<210> SEQ ID NO 35
<211> LENGTH: 18
<212> TYPE: PRT
<213> ORGANISM: Artificial Sequence
<220> FEATURE:
<223> OTHER INFORMATION: TSHR peptide variant

<400> SEQUENCE: 35

Lys Lys Gly Tyr Val Ser Ile Asp Val Lys Leu Gln Lys Lys Glu Gly
1               5                   10                  15

Lys Lys

<210> SEQ ID NO 36
<211> LENGTH: 19
<212> TYPE: PRT
<213> ORGANISM: Artificial Sequence
<220> FEATURE:
<223> OTHER INFORMATION: TSHR peptide variant

<400> SEQUENCE: 36

Lys Lys Gly Ile Tyr Val Ser Ile Asp Val Thr Leu Gln Gln Leu Glu
1               5                   10                  15

Gly Lys Lys

<210> SEQ ID NO 37
<211> LENGTH: 19
<212> TYPE: PRT
```

```
<213> ORGANISM: Artificial Sequence
<220> FEATURE:
<223> OTHER INFORMATION: TSHR peptide variant

<400> SEQUENCE: 37

Lys Lys Gly Ile Tyr Val Ser Ile Asp Val Lys Leu Gln Gln Leu Glu
1               5                   10                  15

Gly Lys Lys

<210> SEQ ID NO 38
<211> LENGTH: 19
<212> TYPE: PRT
<213> ORGANISM: Artificial Sequence
<220> FEATURE:
<223> OTHER INFORMATION: TSHR peptide variant

<400> SEQUENCE: 38

Lys Lys Gly Ile Tyr Val Ser Ile Asp Val Thr Leu Gln Lys Leu Glu
1               5                   10                  15

Gly Lys Lys

<210> SEQ ID NO 39
<211> LENGTH: 19
<212> TYPE: PRT
<213> ORGANISM: Artificial Sequence
<220> FEATURE:
<223> OTHER INFORMATION: TSHR peptide variant

<400> SEQUENCE: 39

Lys Lys Gly Ile Tyr Val Ser Ile Asp Val Thr Leu Gln Gln Lys Glu
1               5                   10                  15

Gly Lys Lys

<210> SEQ ID NO 40
<211> LENGTH: 19
<212> TYPE: PRT
<213> ORGANISM: Artificial Sequence
<220> FEATURE:
<223> OTHER INFORMATION: TSHR peptide variant

<400> SEQUENCE: 40

Lys Lys Gly Ile Tyr Val Ser Ile Asp Val Lys Leu Gln Lys Lys Glu
1               5                   10                  15

Gly Lys Lys

<210> SEQ ID NO 41
<211> LENGTH: 19
<212> TYPE: PRT
<213> ORGANISM: Artificial Sequence
<220> FEATURE:
<223> OTHER INFORMATION: TSHR peptide variant

<400> SEQUENCE: 41

Lys Lys Gly Thr Tyr Val Ser Ile Asp Val Thr Leu Gln Gln Leu Glu
1               5                   10                  15

Gly Lys Lys

<210> SEQ ID NO 42
<211> LENGTH: 19
<212> TYPE: PRT
<213> ORGANISM: Artificial Sequence
<220> FEATURE:
<223> OTHER INFORMATION: TSHR peptide variant
```

-continued

```
<400> SEQUENCE: 42

Lys Lys Gly Thr Tyr Val Ser Ile Asp Val Lys Leu Gln Gln Leu Glu
1               5                   10                  15

Gly Lys Lys

<210> SEQ ID NO 43
<211> LENGTH: 19
<212> TYPE: PRT
<213> ORGANISM: Artificial Sequence
<220> FEATURE:
<223> OTHER INFORMATION: TSHR peptide variant

<400> SEQUENCE: 43

Lys Lys Gly Thr Tyr Val Ser Ile Asp Val Thr Leu Gln Lys Leu Glu
1               5                   10                  15

Gly Lys Lys

<210> SEQ ID NO 44
<211> LENGTH: 19
<212> TYPE: PRT
<213> ORGANISM: Artificial Sequence
<220> FEATURE:
<223> OTHER INFORMATION: TSHR peptide variant

<400> SEQUENCE: 44

Lys Lys Gly Thr Tyr Val Ser Ile Asp Val Thr Leu Gln Gln Lys Glu
1               5                   10                  15

Gly Lys Lys

<210> SEQ ID NO 45
<211> LENGTH: 19
<212> TYPE: PRT
<213> ORGANISM: Artificial Sequence
<220> FEATURE:
<223> OTHER INFORMATION: TSHR peptide variant

<400> SEQUENCE: 45

Lys Lys Gly Thr Tyr Val Ser Ile Asp Val Lys Leu Gln Lys Lys Glu
1               5                   10                  15

Gly Lys Lys

<210> SEQ ID NO 46
<211> LENGTH: 21
<212> TYPE: PRT
<213> ORGANISM: Artificial Sequence
<220> FEATURE:
<223> OTHER INFORMATION: TSHR peptide variant

<400> SEQUENCE: 46

Lys Lys Lys Lys Tyr Val Ser Ile Asp Val Thr Leu Gln Gln Leu Glu
1               5                   10                  15

Ser His Lys Lys Lys
            20

<210> SEQ ID NO 47
<211> LENGTH: 21
<212> TYPE: PRT
<213> ORGANISM: Artificial Sequence
<220> FEATURE:
<223> OTHER INFORMATION: TSHR peptide variant

<400> SEQUENCE: 47

Lys Lys Lys Ile Lys Val Ser Ile Asp Val Thr Leu Gln Gln Leu Glu
```

```
                    1               5                   10                  15

Ser His Lys Lys Lys
            20

<210> SEQ ID NO 48
<211> LENGTH: 21
<212> TYPE: PRT
<213> ORGANISM: Artificial Sequence
<220> FEATURE:
<223> OTHER INFORMATION: TSHR peptide variant

<400> SEQUENCE: 48

Lys Lys Lys Ile Tyr Lys Ser Ile Asp Val Thr Leu Gln Gln Leu Glu
1               5                   10                  15

Ser His Lys Lys Lys
            20

<210> SEQ ID NO 49
<211> LENGTH: 21
<212> TYPE: PRT
<213> ORGANISM: Artificial Sequence
<220> FEATURE:
<223> OTHER INFORMATION: TSHR peptide variant

<400> SEQUENCE: 49

Lys Lys Lys Ile Tyr Val Lys Ile Asp Val Thr Leu Gln Gln Leu Glu
1               5                   10                  15

Ser His Lys Lys Lys
            20

<210> SEQ ID NO 50
<211> LENGTH: 21
<212> TYPE: PRT
<213> ORGANISM: Artificial Sequence
<220> FEATURE:
<223> OTHER INFORMATION: TSHR peptide variant

<400> SEQUENCE: 50

Lys Lys Lys Ile Tyr Val Ser Ile Asp Val Lys Leu Gln Gln Leu Glu
1               5                   10                  15

Ser His Lys Lys Lys
            20

<210> SEQ ID NO 51
<211> LENGTH: 21
<212> TYPE: PRT
<213> ORGANISM: Artificial Sequence
<220> FEATURE:
<223> OTHER INFORMATION: TSHR peptide variant

<400> SEQUENCE: 51

Lys Lys Lys Ile Tyr Val Ser Ile Asp Val Thr Leu Lys Gln Leu Glu
1               5                   10                  15

Ser His Lys Lys Lys
            20

<210> SEQ ID NO 52
<211> LENGTH: 21
<212> TYPE: PRT
<213> ORGANISM: Artificial Sequence
<220> FEATURE:
<223> OTHER INFORMATION: TSHR peptide variant

<400> SEQUENCE: 52
```

```
Lys Lys Lys Ile Tyr Val Ser Ile Asp Val Thr Leu Gln Lys Leu Glu
1               5                   10                  15

Ser His Lys Lys Lys
            20

<210> SEQ ID NO 53
<211> LENGTH: 21
<212> TYPE: PRT
<213> ORGANISM: Artificial Sequence
<220> FEATURE:
<223> OTHER INFORMATION: TSHR peptide variant

<400> SEQUENCE: 53

Lys Lys Lys Ile Tyr Val Ser Ile Asp Val Thr Leu Gln Gln Lys Glu
1               5                   10                  15

Ser His Lys Lys Lys
            20

<210> SEQ ID NO 54
<211> LENGTH: 21
<212> TYPE: PRT
<213> ORGANISM: Artificial Sequence
<220> FEATURE:
<223> OTHER INFORMATION: TSHR peptide variant

<400> SEQUENCE: 54

Lys Lys Lys Ile Tyr Val Ser Ile Asp Val Thr Leu Gln Gln Leu Lys
1               5                   10                  15

Ser His Lys Lys Lys
            20

<210> SEQ ID NO 55
<211> LENGTH: 21
<212> TYPE: PRT
<213> ORGANISM: Artificial Sequence
<220> FEATURE:
<223> OTHER INFORMATION: TSHR peptide variant

<400> SEQUENCE: 55

Lys Lys Lys Ile Tyr Val Ser Ile Asp Val Thr Leu Gln Gln Leu Glu
1               5                   10                  15

Lys His Lys Lys Lys
            20

<210> SEQ ID NO 56
<211> LENGTH: 21
<212> TYPE: PRT
<213> ORGANISM: Artificial Sequence
<220> FEATURE:
<223> OTHER INFORMATION: TSHR peptide variant

<400> SEQUENCE: 56

Lys Lys Lys Ile Tyr Val Ser Ile Asp Val Thr Leu Gln Gln Leu Glu
1               5                   10                  15

Ser Lys Lys Lys Lys
            20

<210> SEQ ID NO 57
<211> LENGTH: 18
<212> TYPE: PRT
<213> ORGANISM: Artificial Sequence
<220> FEATURE:
<223> OTHER INFORMATION: TSHR peptide variant

<400> SEQUENCE: 57
```

```
Lys Lys Lys Tyr Val Ser Ile Asp Val Thr Leu Gln Gln Leu Glu Lys
1               5                   10                  15

Lys Lys

<210> SEQ ID NO 58
<211> LENGTH: 18
<212> TYPE: PRT
<213> ORGANISM: Artificial Sequence
<220> FEATURE:
<223> OTHER INFORMATION: TSHR peptide variant

<400> SEQUENCE: 58

Lys Lys Lys Tyr Val Ser Ile Asp Val Lys Leu Gln Gln Leu Glu Lys
1               5                   10                  15

Lys Lys

<210> SEQ ID NO 59
<211> LENGTH: 18
<212> TYPE: PRT
<213> ORGANISM: Artificial Sequence
<220> FEATURE:
<223> OTHER INFORMATION: TSHR peptide variant

<400> SEQUENCE: 59

Lys Lys Lys Tyr Val Ser Ile Asp Val Thr Leu Gln Lys Leu Glu Lys
1               5                   10                  15

Lys Lys

<210> SEQ ID NO 60
<211> LENGTH: 18
<212> TYPE: PRT
<213> ORGANISM: Artificial Sequence
<220> FEATURE:
<223> OTHER INFORMATION: TSHR peptide variant

<400> SEQUENCE: 60

Lys Lys Lys Tyr Val Ser Ile Asp Val Thr Leu Gln Gln Lys Glu Lys
1               5                   10                  15

Lys Lys

<210> SEQ ID NO 61
<211> LENGTH: 18
<212> TYPE: PRT
<213> ORGANISM: Artificial Sequence
<220> FEATURE:
<223> OTHER INFORMATION: TSHR peptide variant

<400> SEQUENCE: 61

Lys Lys Lys Tyr Val Ser Ile Asp Val Lys Leu Gln Lys Lys Glu Lys
1               5                   10                  15

Lys Lys

<210> SEQ ID NO 62
<211> LENGTH: 15
<212> TYPE: PRT
<213> ORGANISM: Homo sapiens

<400> SEQUENCE: 62

Asn Leu Pro Asn Ile Ser Arg Ile Tyr Val Ser Ile Asp Val Thr
1               5                   10                  15

<210> SEQ ID NO 63
```

```
<211> LENGTH: 21
<212> TYPE: PRT
<213> ORGANISM: Artificial Sequence
<220> FEATURE:
<223> OTHER INFORMATION: TSHR peptide variant

<400> SEQUENCE: 63

Lys Lys Gly Asn Leu Pro Asn Ile Ser Arg Ile Tyr Val Ser Ile Asp
1               5                   10                  15

Val Thr Gly Lys Lys
            20

<210> SEQ ID NO 64
<211> LENGTH: 28
<212> TYPE: PRT
<213> ORGANISM: Homo sapiens

<400> SEQUENCE: 64

Leu Thr Leu Lys Leu Tyr Asn Asn Gly Phe Thr Ser Val Gln Gly Tyr
1               5                   10                  15

Ala Phe Asn Gly Thr Lys Leu Asp Ala Val Tyr Leu
            20                  25

<210> SEQ ID NO 65
<211> LENGTH: 15
<212> TYPE: PRT
<213> ORGANISM: Homo sapiens

<400> SEQUENCE: 65

Leu Thr Leu Lys Leu Tyr Asn Asn Gly Phe Thr Ser Val Gln Gly
1               5                   10                  15

<210> SEQ ID NO 66
<211> LENGTH: 15
<212> TYPE: PRT
<213> ORGANISM: Homo sapiens

<400> SEQUENCE: 66

Thr Leu Lys Leu Tyr Asn Asn Gly Phe Thr Ser Val Gln Gly Tyr
1               5                   10                  15

<210> SEQ ID NO 67
<211> LENGTH: 21
<212> TYPE: PRT
<213> ORGANISM: Homo sapiens

<400> SEQUENCE: 67

Lys Lys Lys Thr Leu Lys Leu Tyr Asn Asn Gly Phe Thr Ser Val Gln
1               5                   10                  15

Gly Tyr Lys Lys Lys
            20

<210> SEQ ID NO 68
<211> LENGTH: 15
<212> TYPE: PRT
<213> ORGANISM: Homo sapiens

<400> SEQUENCE: 68

Leu Lys Leu Tyr Asn Asn Gly Phe Thr Ser Val Gln Gly Tyr Ala
1               5                   10                  15

<210> SEQ ID NO 69
<211> LENGTH: 15
<212> TYPE: PRT
```

```
<213> ORGANISM: Homo sapiens

<400> SEQUENCE: 69

Lys Leu Tyr Asn Asn Gly Phe Thr Ser Val Gln Gly Tyr Ala Phe
1               5                   10                  15

<210> SEQ ID NO 70
<211> LENGTH: 15
<212> TYPE: PRT
<213> ORGANISM: Homo sapiens

<400> SEQUENCE: 70

Leu Tyr Asn Asn Gly Phe Thr Ser Val Gln Gly Tyr Ala Phe Asn
1               5                   10                  15

<210> SEQ ID NO 71
<211> LENGTH: 15
<212> TYPE: PRT
<213> ORGANISM: Homo sapiens

<400> SEQUENCE: 71

Tyr Asn Asn Gly Phe Thr Ser Val Gln Gly Tyr Ala Phe Asn Gly
1               5                   10                  15

<210> SEQ ID NO 72
<211> LENGTH: 15
<212> TYPE: PRT
<213> ORGANISM: Homo sapiens

<400> SEQUENCE: 72

Asn Asn Gly Phe Thr Ser Val Gln Gly Tyr Ala Phe Asn Gly Thr
1               5                   10                  15

<210> SEQ ID NO 73
<211> LENGTH: 15
<212> TYPE: PRT
<213> ORGANISM: Homo sapiens

<400> SEQUENCE: 73

Asn Gly Phe Thr Ser Val Gln Gly Tyr Ala Phe Asn Gly Thr Lys
1               5                   10                  15

<210> SEQ ID NO 74
<211> LENGTH: 15
<212> TYPE: PRT
<213> ORGANISM: Homo sapiens

<400> SEQUENCE: 74

Gly Phe Thr Ser Val Gln Gly Tyr Ala Phe Asn Gly Thr Lys Leu
1               5                   10                  15

<210> SEQ ID NO 75
<211> LENGTH: 15
<212> TYPE: PRT
<213> ORGANISM: Homo sapiens

<400> SEQUENCE: 75

Phe Thr Ser Val Gln Gly Tyr Ala Phe Asn Gly Thr Lys Leu Asp
1               5                   10                  15

<210> SEQ ID NO 76
<211> LENGTH: 15
<212> TYPE: PRT
<213> ORGANISM: Homo sapiens
```

-continued

```
<400> SEQUENCE: 76

Thr Ser Val Gln Gly Tyr Ala Phe Asn Gly Thr Lys Leu Asp Ala
1               5                   10                  15

<210> SEQ ID NO 77
<211> LENGTH: 15
<212> TYPE: PRT
<213> ORGANISM: Homo sapiens

<400> SEQUENCE: 77

Ser Val Gln Gly Tyr Ala Phe Asn Gly Thr Lys Leu Asp Ala Val
1               5                   10                  15

<210> SEQ ID NO 78
<211> LENGTH: 15
<212> TYPE: PRT
<213> ORGANISM: Homo sapiens

<400> SEQUENCE: 78

Val Gln Gly Tyr Ala Phe Asn Gly Thr Lys Leu Asp Ala Val Tyr
1               5                   10                  15

<210> SEQ ID NO 79
<211> LENGTH: 29
<212> TYPE: PRT
<213> ORGANISM: Homo sapiens

<400> SEQUENCE: 79

Gly Gly Met Gly Cys Ser Ser Pro Cys Glu Cys His Gln Glu Glu
1               5                   10                  15

Asp Phe Arg Val Thr Cys Lys Asp Ile Gln Arg Ile Pro
            20                  25

<210> SEQ ID NO 80
<211> LENGTH: 30
<212> TYPE: PRT
<213> ORGANISM: Homo sapiens

<400> SEQUENCE: 80

Glu Glu Asp Phe Arg Val Thr Cys Lys Asp Ile Gln Arg Ile Pro Ser
1               5                   10                  15

Leu Pro Pro Ser Thr Gln Thr Leu Lys Leu Ile Glu Thr His
            20                  25                  30

<210> SEQ ID NO 81
<211> LENGTH: 30
<212> TYPE: PRT
<213> ORGANISM: Homo sapiens

<400> SEQUENCE: 81

Ser Leu Pro Pro Ser Thr Gln Thr Leu Lys Leu Ile Glu Thr His Leu
1               5                   10                  15

Arg Thr Ile Pro Ser His Ala Phe Ser Asn Leu Pro Asn Ile
            20                  25                  30

<210> SEQ ID NO 82
<211> LENGTH: 29
<212> TYPE: PRT
<213> ORGANISM: Homo sapiens

<400> SEQUENCE: 82

Glu Ser His Ser Phe Tyr Asn Leu Ser Lys Val Thr His Ile Glu Ile
1               5                   10                  15
```

Arg Asn Thr Arg Asn Leu Thr Tyr Ile Asp Pro Asp Ala
            20                  25

<210> SEQ ID NO 83
<211> LENGTH: 29
<212> TYPE: PRT
<213> ORGANISM: Homo sapiens

<400> SEQUENCE: 83

Glu Ile Arg Asn Thr Arg Asn Leu Thr Tyr Ile Asp Pro Asp Ala Leu
1               5                   10                  15

Lys Glu Leu Pro Leu Leu Lys Phe Leu Gly Ile Phe Asn
            20                  25

<210> SEQ ID NO 84
<211> LENGTH: 29
<212> TYPE: PRT
<213> ORGANISM: Homo sapiens

<400> SEQUENCE: 84

Leu Lys Glu Leu Pro Leu Leu Lys Phe Leu Gly Ile Phe Asn Thr Gly
1               5                   10                  15

Leu Lys Met Phe Pro Asp Leu Thr Lys Val Tyr Ser Thr
            20                  25

<210> SEQ ID NO 85
<211> LENGTH: 30
<212> TYPE: PRT
<213> ORGANISM: Homo sapiens

<400> SEQUENCE: 85

Thr Asp Ile Phe Phe Ile Leu Glu Ile Thr Asp Asn Pro Tyr Met Thr
1               5                   10                  15

Ser Ile Pro Val Asn Ala Phe Gln Gly Leu Cys Asn Glu Thr
            20                  25                  30

<210> SEQ ID NO 86
<211> LENGTH: 28
<212> TYPE: PRT
<213> ORGANISM: Homo sapiens

<400> SEQUENCE: 86

Thr Ser Ile Pro Val Asn Ala Phe Gln Gly Leu Cys Asn Glu Thr Leu
1               5                   10                  15

Thr Leu Lys Leu Tyr Asn Asn Gly Phe Thr Ser Val
            20                  25

<210> SEQ ID NO 87
<211> LENGTH: 28
<212> TYPE: PRT
<213> ORGANISM: Homo sapiens

<400> SEQUENCE: 87

Gln Gly Tyr Ala Phe Asn Gly Thr Lys Leu Asp Ala Val Tyr Leu Asn
1               5                   10                  15

Lys Asn Lys Tyr Leu Thr Val Ile Asp Lys Asp Ala
            20                  25

<210> SEQ ID NO 88
<211> LENGTH: 28
<212> TYPE: PRT
<213> ORGANISM: Homo sapiens

<400> SEQUENCE: 88

Asn Lys Asn Lys Tyr Leu Thr Val Ile Asp Lys Asp Ala Phe Gly Gly
1               5                   10                  15

Val Tyr Ser Gly Pro Ser Leu Leu Asp Val Ser Gln
            20                  25

<210> SEQ ID NO 89
<211> LENGTH: 28
<212> TYPE: PRT
<213> ORGANISM: Homo sapiens

<400> SEQUENCE: 89

Phe Gly Gly Val Tyr Ser Gly Pro Ser Leu Leu Asp Val Ser Gln Thr
1               5                   10                  15

Ser Val Thr Ala Leu Pro Ser Lys Gly Leu Glu His
            20                  25

<210> SEQ ID NO 90
<211> LENGTH: 28
<212> TYPE: PRT
<213> ORGANISM: Homo sapiens

<400> SEQUENCE: 90

Thr Ser Val Thr Ala Leu Pro Ser Lys Gly Leu Glu His Leu Lys Glu
1               5                   10                  15

Leu Ile Ala Arg Asn Thr Trp Thr Leu Lys Lys Leu
            20                  25

<210> SEQ ID NO 91
<211> LENGTH: 28
<212> TYPE: PRT
<213> ORGANISM: Homo sapiens

<400> SEQUENCE: 91

Leu Lys Glu Leu Ile Ala Arg Asn Thr Trp Thr Leu Lys Lys Leu Pro
1               5                   10                  15

Leu Ser Leu Ser Phe Leu His Leu Thr Arg Ala Asp
            20                  25

<210> SEQ ID NO 92
<211> LENGTH: 28
<212> TYPE: PRT
<213> ORGANISM: Homo sapiens

<400> SEQUENCE: 92

Pro Leu Ser Leu Ser Phe Leu His Leu Thr Arg Ala Asp Leu Ser Tyr
1               5                   10                  15

Pro Ser His Cys Cys Ala Phe Lys Asn Gln Lys Lys
            20                  25

<210> SEQ ID NO 93
<211> LENGTH: 28
<212> TYPE: PRT
<213> ORGANISM: Homo sapiens

<400> SEQUENCE: 93

Leu Ser Tyr Pro Ser His Cys Cys Ala Phe Lys Asn Gln Lys Lys Ile
1               5                   10                  15

Arg Gly Ile Leu Glu Ser Leu Met Cys Asn Glu Ser
            20                  25

<210> SEQ ID NO 94
<211> LENGTH: 28
<212> TYPE: PRT
<213> ORGANISM: Homo sapiens

<400> SEQUENCE: 94

Ile Arg Gly Ile Leu Glu Ser Leu Met Cys Asn Glu Ser Ser Met Gln
1               5                   10                  15

Ser Leu Arg Gln Arg Lys Ser Val Asn Ala Leu Asn
            20                  25

<210> SEQ ID NO 95
<211> LENGTH: 29
<212> TYPE: PRT
<213> ORGANISM: Homo sapiens

<400> SEQUENCE: 95

Ser Met Gln Ser Leu Arg Gln Arg Lys Ser Val Asn Ala Leu Asn Ser
1               5                   10                  15

Pro Leu His Gln Glu Tyr Glu Glu Asn Leu Gly Asp Ser
            20                  25

<210> SEQ ID NO 96
<211> LENGTH: 29
<212> TYPE: PRT
<213> ORGANISM: Homo sapiens

<400> SEQUENCE: 96

Ser Pro Leu His Gln Glu Tyr Glu Glu Asn Leu Gly Asp Ser Ile Val
1               5                   10                  15

Gly Tyr Lys Glu Lys Ser Lys Phe Gln Asp Thr His Asn
            20                  25

<210> SEQ ID NO 97
<211> LENGTH: 29
<212> TYPE: PRT
<213> ORGANISM: Homo sapiens

<400> SEQUENCE: 97

Ile Val Gly Tyr Lys Glu Lys Ser Lys Phe Gln Asp Thr His Asn Asn
1               5                   10                  15

Ala His Tyr Tyr Val Phe Phe Glu Glu Gln Glu Asp Glu
            20                  25

<210> SEQ ID NO 98
<211> LENGTH: 29
<212> TYPE: PRT
<213> ORGANISM: Homo sapiens

<400> SEQUENCE: 98

Asn Ala His Tyr Tyr Val Phe Phe Glu Glu Gln Glu Asp Glu Ile Ile
1               5                   10                  15

Gly Phe Gly Gln Glu Leu Lys Asn Pro Gln Glu Glu Thr
            20                  25

<210> SEQ ID NO 99
<211> LENGTH: 29
<212> TYPE: PRT
<213> ORGANISM: Homo sapiens

<400> SEQUENCE: 99

Ile Ile Gly Phe Gly Gln Glu Leu Lys Asn Pro Gln Glu Glu Thr Leu

-continued

```
                1               5                  10                  15
        Gln Ala Phe Asp Ser His Tyr Asp Tyr Thr Ile Cys Gly
                        20                  25

<210> SEQ ID NO 100
<211> LENGTH: 29
<212> TYPE: PRT
<213> ORGANISM: Homo sapiens

<400> SEQUENCE: 100

Leu Gln Ala Phe Asp Ser His Tyr Asp Tyr Thr Ile Cys Gly Asp Ser
1               5                   10                  15

Glu Asp Met Val Cys Thr Pro Lys Ser Asp Glu Phe Asn
                20                  25

<210> SEQ ID NO 101
<211> LENGTH: 27
<212> TYPE: PRT
<213> ORGANISM: Homo sapiens

<400> SEQUENCE: 101

Asp Ser Glu Asp Met Val Cys Thr Pro Lys Ser Asp Glu Phe Asn Pro
1               5                   10                  15

Cys Glu Asp Ile Met Gly Tyr Lys Phe Leu Arg
                20                  25

<210> SEQ ID NO 102
<211> LENGTH: 29
<212> TYPE: PRT
<213> ORGANISM: Homo sapiens

<400> SEQUENCE: 102

Lys Leu Asp Ala Val Tyr Leu Asn Lys Asn Lys Tyr Leu Thr Val Ile
1               5                   10                  15

Asp Lys Asp Ala Phe Gly Gly Val Tyr Ser Gly Pro Ser
                20                  25

<210> SEQ ID NO 103
<211> LENGTH: 15
<212> TYPE: PRT
<213> ORGANISM: Homo sapiens

<400> SEQUENCE: 103

Ser Ile Asp Val Thr Leu Gln Gln Leu Glu Ser His Ser Phe Tyr
1               5                   10                  15

<210> SEQ ID NO 104
<211> LENGTH: 15
<212> TYPE: PRT
<213> ORGANISM: Homo sapiens

<400> SEQUENCE: 104

Ile Asp Val Thr Leu Gln Gln Leu Glu Ser His Ser Phe Tyr Asn
1               5                   10                  15

<210> SEQ ID NO 105
<211> LENGTH: 15
<212> TYPE: PRT
<213> ORGANISM: Homo sapiens

<400> SEQUENCE: 105

Asp Val Thr Leu Gln Gln Leu Glu Ser His Ser Phe Tyr Asn Leu
1               5                   10                  15
```

```
<210> SEQ ID NO 106
<211> LENGTH: 15
<212> TYPE: PRT
<213> ORGANISM: Homo sapiens

<400> SEQUENCE: 106

Val Thr Leu Gln Gln Leu Glu Ser His Ser Phe Tyr Asn Leu Ser
1               5                   10                  15

<210> SEQ ID NO 107
<211> LENGTH: 15
<212> TYPE: PRT
<213> ORGANISM: Homo sapiens

<400> SEQUENCE: 107

Thr Leu Gln Gln Leu Glu Ser His Ser Phe Tyr Asn Leu Ser Lys
1               5                   10                  15

<210> SEQ ID NO 108
<211> LENGTH: 15
<212> TYPE: PRT
<213> ORGANISM: Homo sapiens

<400> SEQUENCE: 108

Leu Gln Gln Leu Glu Ser His Ser Phe Tyr Asn Leu Ser Lys Val
1               5                   10                  15

<210> SEQ ID NO 109
<211> LENGTH: 15
<212> TYPE: PRT
<213> ORGANISM: Homo sapiens

<400> SEQUENCE: 109

Gln Gln Leu Glu Ser His Ser Phe Tyr Asn Leu Ser Lys Val Thr
1               5                   10                  15

<210> SEQ ID NO 110
<211> LENGTH: 15
<212> TYPE: PRT
<213> ORGANISM: Homo sapiens

<400> SEQUENCE: 110

Gln Leu Glu Ser His Ser Phe Tyr Asn Leu Ser Lys Val Thr His
1               5                   10                  15

<210> SEQ ID NO 111
<211> LENGTH: 15
<212> TYPE: PRT
<213> ORGANISM: Homo sapiens

<400> SEQUENCE: 111

Leu Glu Ser His Ser Phe Tyr Asn Leu Ser Lys Val Thr His Ile
1               5                   10                  15

<210> SEQ ID NO 112
<211> LENGTH: 21
<212> TYPE: PRT
<213> ORGANISM: Artificial Sequence
<220> FEATURE:
<223> OTHER INFORMATION: TSHR peptide variant

<400> SEQUENCE: 112

Lys Lys Gly Ile Tyr Val Lys Ile Asp Val Thr Leu Gln Gln Leu Glu
1               5                   10                  15
```

Ser His Gly Lys Lys
            20

<210> SEQ ID NO 113
<211> LENGTH: 21
<212> TYPE: PRT
<213> ORGANISM: Artificial Sequence
<220> FEATURE:
<223> OTHER INFORMATION: TSHR peptide variant

<400> SEQUENCE: 113

Lys Lys Gly Ile Tyr Val Ser Lys Asp Val Thr Leu Gln Gln Leu Glu
1               5                   10                  15

Ser His Gly Lys Lys
            20

<210> SEQ ID NO 114
<211> LENGTH: 21
<212> TYPE: PRT
<213> ORGANISM: Artificial Sequence
<220> FEATURE:
<223> OTHER INFORMATION: TSHR peptide variant

<400> SEQUENCE: 114

Lys Lys Gly Ile Tyr Val Ser Ile Lys Val Thr Leu Gln Gln Leu Glu
1               5                   10                  15

Ser His Gly Lys Lys
            20

<210> SEQ ID NO 115
<211> LENGTH: 21
<212> TYPE: PRT
<213> ORGANISM: Artificial Sequence
<220> FEATURE:
<223> OTHER INFORMATION: TSHR peptide variant

<400> SEQUENCE: 115

Lys Lys Gly Ile Tyr Val Ser Ile Asp Lys Thr Leu Gln Gln Leu Glu
1               5                   10                  15

Ser His Gly Lys Lys
            20

<210> SEQ ID NO 116
<211> LENGTH: 21
<212> TYPE: PRT
<213> ORGANISM: Artificial Sequence
<220> FEATURE:
<223> OTHER INFORMATION: TSHR peptide variant

<400> SEQUENCE: 116

Lys Lys Gly Ile Tyr Val Ser Ile Asp Val Thr Lys Gln Gln Leu Glu
1               5                   10                  15

Ser His Gly Lys Lys
            20

<210> SEQ ID NO 117
<211> LENGTH: 21
<212> TYPE: PRT
<213> ORGANISM: Artificial Sequence
<220> FEATURE:
<223> OTHER INFORMATION: TSHR peptide variant

<400> SEQUENCE: 117

Lys Lys Gly Ile Tyr Val Ser Ile Asp Val Thr Leu Lys Gln Leu Glu

```
                1               5                   10                  15

Ser His Gly Lys Lys
            20

<210> SEQ ID NO 118
<211> LENGTH: 21
<212> TYPE: PRT
<213> ORGANISM: Artificial Sequence
<220> FEATURE:
<223> OTHER INFORMATION: TSHR peptide variant

<400> SEQUENCE: 118

Lys Lys Lys Ile Tyr Val Ser Lys Asp Val Thr Leu Gln Gln Leu Glu
1               5                   10                  15

Ser His Lys Lys Lys
            20

<210> SEQ ID NO 119
<211> LENGTH: 21
<212> TYPE: PRT
<213> ORGANISM: Artificial Sequence
<220> FEATURE:
<223> OTHER INFORMATION: TSHR peptide variant

<400> SEQUENCE: 119

Lys Lys Lys Ile Tyr Val Ser Ile Lys Val Thr Leu Gln Gln Leu Glu
1               5                   10                  15

Ser His Lys Lys Lys
            20

<210> SEQ ID NO 120
<211> LENGTH: 21
<212> TYPE: PRT
<213> ORGANISM: Artificial Sequence
<220> FEATURE:
<223> OTHER INFORMATION: TSHR peptide variant

<400> SEQUENCE: 120

Lys Lys Lys Ile Tyr Val Ser Ile Asp Lys Thr Leu Gln Gln Leu Glu
1               5                   10                  15

Ser His Lys Lys Lys
            20

<210> SEQ ID NO 121
<211> LENGTH: 21
<212> TYPE: PRT
<213> ORGANISM: Artificial Sequence
<220> FEATURE:
<223> OTHER INFORMATION: TSHR peptide variant

<400> SEQUENCE: 121

Lys Lys Lys Ile Tyr Val Ser Ile Asp Val Thr Lys Gln Gln Leu Glu
1               5                   10                  15

Ser His Lys Lys Lys
            20

<210> SEQ ID NO 122
<211> LENGTH: 15
<212> TYPE: PRT
<213> ORGANISM: Homo sapiens

<400> SEQUENCE: 122

Leu Arg Thr Ile Pro Ser His Ala Phe Ser Asn Leu Pro Asn Ile
1               5                   10                  15
```

<210> SEQ ID NO 123
<211> LENGTH: 15
<212> TYPE: PRT
<213> ORGANISM: Homo sapiens

<400> SEQUENCE: 123

Arg Thr Ile Pro Ser His Ala Phe Ser Asn Leu Pro Asn Ile Ser
1               5                   10                  15

<210> SEQ ID NO 124
<211> LENGTH: 15
<212> TYPE: PRT
<213> ORGANISM: Homo sapiens

<400> SEQUENCE: 124

Thr Ile Pro Ser His Ala Phe Ser Asn Leu Pro Asn Ile Ser Arg
1               5                   10                  15

<210> SEQ ID NO 125
<211> LENGTH: 15
<212> TYPE: PRT
<213> ORGANISM: Homo sapiens

<400> SEQUENCE: 125

Ile Pro Ser His Ala Phe Ser Asn Leu Pro Asn Ile Ser Arg Ile
1               5                   10                  15

<210> SEQ ID NO 126
<211> LENGTH: 15
<212> TYPE: PRT
<213> ORGANISM: Homo sapiens

<400> SEQUENCE: 126

Pro Ser His Ala Phe Ser Asn Leu Pro Asn Ile Ser Arg Ile Tyr
1               5                   10                  15

<210> SEQ ID NO 127
<211> LENGTH: 15
<212> TYPE: PRT
<213> ORGANISM: Homo sapiens

<400> SEQUENCE: 127

Ser His Ala Phe Ser Asn Leu Pro Asn Ile Ser Arg Ile Tyr Val
1               5                   10                  15

<210> SEQ ID NO 128
<211> LENGTH: 15
<212> TYPE: PRT
<213> ORGANISM: Homo sapiens

<400> SEQUENCE: 128

His Ala Phe Ser Asn Leu Pro Asn Ile Ser Arg Ile Tyr Val Ser
1               5                   10                  15

<210> SEQ ID NO 129
<211> LENGTH: 15
<212> TYPE: PRT
<213> ORGANISM: Homo sapiens

<400> SEQUENCE: 129

Ala Phe Ser Asn Leu Pro Asn Ile Ser Arg Ile Tyr Val Ser Ile
1               5                   10                  15

```
<210> SEQ ID NO 130
<211> LENGTH: 15
<212> TYPE: PRT
<213> ORGANISM: Homo sapiens

<400> SEQUENCE: 130

Phe Ser Asn Leu Pro Asn Ile Ser Arg Ile Tyr Val Ser Ile Asp
1               5                   10                  15

<210> SEQ ID NO 131
<211> LENGTH: 15
<212> TYPE: PRT
<213> ORGANISM: Homo sapiens

<400> SEQUENCE: 131

Leu Pro Asn Ile Ser Arg Ile Tyr Val Ser Ile Asp Val Thr Leu
1               5                   10                  15

<210> SEQ ID NO 132
<211> LENGTH: 15
<212> TYPE: PRT
<213> ORGANISM: Homo sapiens

<400> SEQUENCE: 132

Pro Asn Ile Ser Arg Ile Tyr Val Ser Ile Asp Val Thr Leu Gln
1               5                   10                  15

<210> SEQ ID NO 133
<211> LENGTH: 15
<212> TYPE: PRT
<213> ORGANISM: Homo sapiens

<400> SEQUENCE: 133

Asn Ile Ser Arg Ile Tyr Val Ser Ile Asp Val Thr Leu Gln Gln
1               5                   10                  15

<210> SEQ ID NO 134
<211> LENGTH: 21
<212> TYPE: PRT
<213> ORGANISM: Artificial Sequence
<220> FEATURE:
<223> OTHER INFORMATION: TSHR peptide variant

<400> SEQUENCE: 134

Lys Lys Gly Ile Tyr Leu Ser Ile Asp Ala Thr Leu Gln Arg Leu Glu
1               5                   10                  15

Pro His Gly Lys Lys
            20
```